United States Patent [19]
Yamada et al.

[11] Patent Number: 6,046,348
[45] Date of Patent: Apr. 4, 2000

[54] SILANE COMPOUND, METHOD FOR MAKING THE SAME, AND ELECTROPHOTOGRAPHIC PHOTORECEPTOR

[75] Inventors: Wataru Yamada; Katsumi Nukada; Masahiro Iwasaki, all of Minami-Ashigara, Japan

[73] Assignee: Fuji Xerox Co., Ltd., Tokyo, Japan

[21] Appl. No.: 08/892,912

[22] Filed: Jul. 15, 1997

[30] Foreign Application Priority Data

| | | | |
|---|---|---|---|
| Jul. 17, 1996 | [JP] | Japan | 8-187931 |
| Jul. 17, 1996 | [JP] | Japan | 8-187932 |
| Jul. 17, 1996 | [JP] | Japan | 8-187933 |
| Jan. 7, 1997 | [JP] | Japan | 9-000861 |
| May 12, 1997 | [JP] | Japan | 9-121256 |
| May 19, 1997 | [JP] | Japan | 9-129039 |
| Jul. 4, 1997 | [JP] | Japan | 9-180147 |

[51] Int. Cl.[7] .................................................. C02F 2/10
[52] U.S. Cl. ..................... 556/413; 556/410; 556/418; 556/424
[58] Field of Search .................... 556/413, 410, 556/424, 418

[56] References Cited

U.S. PATENT DOCUMENTS

| | | | |
|---|---|---|---|
| 5,688,961 | 11/1997 | Kushibiki et al. | 556/413 X |
| 5,733,999 | 3/1998 | Bomal et al. | 556/413 X |

FOREIGN PATENT DOCUMENTS

| | | |
|---|---|---|
| 7-72640 | 3/1995 | Japan . |
| B2-7-120051 | 12/1995 | Japan . |
| 8-15886 | 1/1996 | Japan . |

OTHER PUBLICATIONS

"The Chemistry of Organic Silicone Compounds", (Ed. S. Patai, 1989), pp. 655.

"Proceedings of IS&T's Eleventh International Congress On Advances in Non–Impact Printing Technologies,", pp. 57–59.

"Experimental Chemistry 19" (Organic Synthesis), pp. 57.

*Primary Examiner*—Paul F. Shaver
*Attorney, Agent, or Firm*—Oliff & Berridge, PLC

[57] ABSTRACT

The present invention provides a silane compound represented by general formula, I, below, a method for preparing the silane compound and a photoreceptor for use in electrostatic photography utilizing the silane compound. Accordingly, the present invention provides an electrophotographic photoreceptor having an enhanced mechanical strength, a high sensitivity and superior stability to environmental conditions.

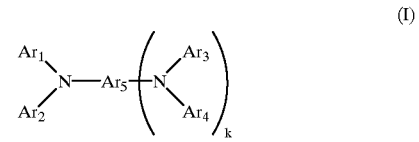

(I)

6 Claims, 23 Drawing Sheets

SILANE COMPOUND, METHOD FOR MAKING THE SAME, AND ELECTROPHOTOGRAPHIC PHOTORECEPTOR

BACKGROUND OF THE INVENTION

1. Field of the Invention

The present invention relates to a novel silane compound, a method for making it, and an electrophotographic photoreceptor.

2. Description of the Related Art

The charge-transport layer of an electrophotographic photoreceptor generally comprises a binder polymer, such as polyester, and a charge-transport material, which has a low molecular weight, such as a triaryl amine and a tetraaryl benzidine. In order to obtain a film-forming capability, the charge-transport material, which has a low molecular weight, is dispersed in the binder polymer.

However, since the charge-transport material, which has a low molecular weight, is dispersed in the binder polymer, the mechanical strength inherent to the binder polymer decreases, thus presenting a problem that the above-described electrophotographic photoreceptor has an inferior durability.

In order to overcome the problem, there has been proposed a charge-transport polymer which is represented by a polyvinyl carbazole and contains a charge-transport component in the main molecular chain, but such a charge-transport polymer cannot completely solve the problem of electric characteristics and mechanical strength.

Recently, the use of a charge-transport material, which has a low molecular weight, as an organic EL element is drawing attention. In this case, the problem is that it is difficult to obtain a durable and stable element because the material, which has a low molecular weight, is fused by Joule heat generated during use.

The following methods are known as methods for synthesizing conventionally available silane compounds:

(1) A method based on the hydrosilylation of an alkene or alkyne

Various silane compounds having a Si—C bond are synthesized by hydrosilylation of an alkene or alkyne, using a Speier reagent {$H_2PtCl_6$/IPA (isopropyl alcohol)} as described in "Chemistry of Organometallics," Shokabo Publishing Co., Ltd., 1982, pp. 322. This method makes it possible to carry out the synthesis by use of a catalyst in an amount as small as $1 \times 10^{-7}$ mol, and therefore it is a very useful method. However, since this method provides by-products, which are caused by isomers or reductive reactions and which need to be strictly removed by a purification treatment such as distillation, this method is not suitable for the synthesis of the present invention using a silane compound having a high boiling point.

(2) A method using a Grignard reaction

As described in "The Chemistry of Organic Silicone Compounds" (Ed. S. Patai, 1989), pp. 655, a silane compound can be synthesized by use of a Grignard reagent. However, since the Grignard reaction is very sensitive to oxygen and moisture and produces a large amount of inorganic salts, whose posttreatment is difficult, the industrialization of this method is very costly.

(3) Synthesis of amine-based silane compound by use of a dehydrochlorination

As described in "The Chemistry of Organic Silicone Compounds" (Ed. S. Patai, 1989), pp. 655, a silane compound can be synthesized by a dehydrochlorination reaction between a silane having a halogen substituent and an amine. The problems relating to this method are that the obtained compounds are limited to compounds of a special type and that the obtained compounds, which necessarily contain an amino group, tend to trap charges and adversely affect the electrical characteristics when these compounds are used as a charge-transport material.

(4) A method using a urethane linkage-forming reaction

Japanese Patent Application Laid-Open (JP-A) No. 3-191,358 proposes to incorporate a silane compound, which has a charge-transport moiety, into an electrophotographic photoreceptor by a urethane linkage. The problem of the compound prepared according to this method is that, since the compound has a hydrogen atom directly linked to a heteroatom, the compound tends to adsorb the moisture in the atmosphere and the organoelectronic device, such as an electrophotographic photoreceptor, which uses this compound, is susceptible to moisture and therefore unstable under environmental conditions.

As to a material, which forms the charge-transport layer of an electrophotographic photoreceptor, two types are widely known: namely, a charge-transport polymer such as polyvinyl carbazole which contains a charge-transport component in the main molecular chain, and a charge-transport dispersion comprising a charge-transport compound of a low molecular weight which is produced by dispersing the charge-transport compound having a low molecular weight such as a triaryl amine, in a binder polymer. Of the foregoing two types, a dispersion comprising a substance having a low molecular weight is now becoming mainstream in the field of electrophotographic photoreceptors, because a variety of substances can be used and because a highly functional charge-transport material can be obtained.

With the advent of highly functional organic photoreceptors, such an organic photoreceptor is now being used in high-speed copiers and printers. However, the level of the function of organic photoreceptors now in use in high-speed copiers and printers is not always satisfactory and there is a strong need for a photoreceptor having a longer service life. One of the important factors which determine the life of the organic photoreceptor is the degree of wear of the surface layer. Since the main stream of the current organic photoreceptors is a so-called laminated photoreceptor, which is produced by laminating a charge-transport layer onto a charge-generation layer, the surface layer is often the charge-transport layer. Even though satisfactory electric characteristics are now being attained, a charge-transport layer based on a dispersion of a substance having a low molecular weight, which is now mainstream in the field of electrophotographic photoreceptor, suffers from weakness in wear due to loss of the mechanical strength inherent in the binder polymer, because a compound having a low molecular weight is dispersed in the binder polymer.

Many attempts have been made to solve the above-mentioned problems, and one of the active studies is the use of a polymeric material as the charge-transport material. For example, U.S. Pat. No. 4,806,443 discloses a polycarbonate obtained by the polymerization of a specific dihydroxyaryl amine with bischloroformate, while U.S. Pat. No. 4,806,444 discloses a polycarbonate obtained by the polymerization of a specific dihydroxyaryl amine with phosgene. U.S. Pat. No. 4,801,517 discloses a polycarbonate obtained by the polymerization of a bishydroxyalkylaryl amine with bischloroformate or phosgene, while U.S. Pat. Nos. 4,937,165 and 4,959,288 disclose a polycarbonate obtained by the polymerization of a specific dihydroxyaryl amine or bishydroxyalkylaryl amine with bischloroformate and a polyester obtained by polymerization of a specific dihydroxyaryl amine or bishydroxyalkylaryl amine with a bisacyl halide. U.S. Pat. No. 5,034,296 discloses a polycarbonate and a polyester obtained from an aryl amine having a specific fluorene skeleton. U.S. Pat. No. 4,983,482 discloses a polyurethane. Japanese Patent Application Publication (JP-B) No. 59-28,903 discloses a polyester comprising a specific bisstyrylbisaryl amine as a main chain. Japanese Patent Application Laid-Open (JP-A) Nos. 61-20,953, 1-134,456, 1-134,457, 1-134,462, 4-133,065, 4-133,066, and others disclose polymers having a charge transporting group, such as hydrazone or a triaryl amine, as a pendant and an electrophotographic photoreceptor which utilizes such a polymer. However, none of the above-described polymeric charge-transport materials is satisfactory in terms of sensitivity, residual potential, and durability as an electrophotographic photoreceptor.

On the other hand, a method has been proposed which comprises dispersing a charge-transport material having a low molecular weight in a binder polymer or in a polymer precursor and thereafter hardening the binder polymer or polymer precursor by means of a curing reaction. For example, JP-A No. 56-48,637 and JP-B No. 56-42,863 disclose an example using an acrylic polymer, while JP-B Nos. 5-47,104, 60-22,347, and 7-120,051 each disclose an example using a silicone polymer or polymer precursor. None of these methods, however, solves the problem because the concentration of the charge-transport material having a low molecular weight needs to be set to such a high value, e.g., 30 to 50%, that the progress of the curing reaction of the binder is inhibited and therefore the charge-transport material having a low molecular weight is separated from between the binder polymers to be worn out.

Further, aiming at the enhancement in the lubricating property of the surface of an electrophotographic photoreceptor, JP-A Nos. 57-5,050, 61-219,049, and 62-205,357 disclose an example wherein a silicon-containing polymer is added, while JP-A Nos. 50-23,231, 61-116,362, 61-204,633, and 61-270,768 disclose an example wherein a fluorine-containing polymer is added. As an attempt to attain the same objective, JP-A No. 63-65,449 discloses an example wherein particles of a silicon-containing polymer are added, while JP-A No. 2-144,550 discloses an example wherein particles of a fluorine-containing polymer are added. None of these methods, however, solves the problem because these polymers or polymer particles have such poor compatibility with charge-transport material or binder polymer that layer separation takes place within the photosensitive layer and the transparency of the layer is lost, thereby deteriorating the electric characteristics of the photoreceptor.

Further, a method has been proposed which comprises adding particles of a tough resin to the photosensitive layer. For example, JP-A No. 60-177,349 disclose an example wherein particles of a melamine resin are added. This method, however, does not solve the problem because the melamine resin particles have such a poor compatibility with the charge-transport material or with the binder polymer that layer separation takes place within the photosensitive layer and the transparency of the layer is lost, thereby deteriorating the electric characteristics of the photoreceptor.

Further, as a method for protecting the surface of an electrophotographic photoreceptor, JP-A Nos. 56-38,055 and 60-55,355 disclose an example wherein an imide-based polymer is used as the surface protecting layer, JP-A Nos. 59-185,347 and 61-217,052 disclose an example wherein a melamine-based polymer is used as the surface protecting layer, JP-A No. 59-46,652 discloses an example wherein an acrylic polymer and a melamine-based polymer are used as the surface protecting layer, "Proc. IS&T 11th Internat. Cong. on Advances in Nonimpact Printing Technol.", pp. 57–59, and JP-A No. 8-15,886 disclose an example wherein a siloxane-based polymer produced by a sol/gel process is used as the surface protecting layer, and JP-A No. 7-333,881 discloses an example wherein an inorganic thin film produced by a plasma CVD process is used as the surface protecting layer. However, many of these surface protective layers have drawbacks, an example of which is that the residual potential increases. Although the method disclosed in "Proc. IS&T 11th Internat. Cong. on Advances in Nonimpact Printing Technol.", pp. 57–59, which uses a sol/gel process, is described as a method advantageous in residual potential and mechanical strength, the concrete structure of the compound is not disclosed at all.

JP-A No. 3-191,358 discloses a method as a type of sol/gel process, wherein one of the materials involved in the sol/gel process is provided with a charge-transport function. Since all compounds disclosed in this case use a urethanelinkage and since the compounds have a hydrogen atom, which is directly linked to a heteroatom and which tends to form a hydrogen bond and therefore is inclined to adsorb moisture in the atmosphere, these compounds are susceptible to the influence of discharge products or humidity in spite of the apparent effect of increasing the mechanical strength of the charge-transport layer. Therefore, it is difficult to obtain a stable image for a long time by use of these compounds because image drift tends to occur when these compounds are used repeatedly or when these compounds are used under conditions of high temperature and high humidity. In addition, JP-A No. 7-72,640 proposes using a monomeric charge-transport compound, which has a carbon-carbon-polymerizable double bond in a triphenyl amine skeleton, singly or in a combination with a polymer so that a polymerization will be effected by means of light or heat to form a tough film. However, since the polymerizable site is only one in the monomer and therefore the density of cross-linkage is remains low after polymerization, a sufficient durability level as an electrophotographic photoreceptor has not been attained.

SUMMARY OF THE INVENTION

One object of the present invention is to provide a novel compound, which has an excellent solubility and film forming capability, forms a tough film and is applicable to a variety of organoelectronic devices including an organic EL element and an electrophotographic photoreceptor, and also to provide a method for making the novel compound.

The present inventors have found that a specific silane compound can be cured three-dimensionally and that the cured film is superior in charge transportability, resistance to mechanical wear, stability in various environmental conditions, and durability.

The silane compound of the present invention is represented by general formula I:

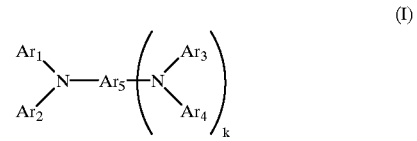

where
  $Ar_1$–$Ar_4$ are independently substituted or unsubstituted aryl groups;

Ar$_5$ is a substituted or unsubstituted aryl or arylene group, provided that one to four of Ar$_1$–Ar$_5$ have a substituent represented by —Q—SiR$_{1(3-a)}$(OR$_2$)$_a$ where R$_1$ is selected from the group consisting of hydrogen, alkyl, and substituted and unsubstituted aryl groups;

R$_2$ is selected from the group consisting of hydrogen, alkyl, and trialkylsilyl groups;

a is an integer of 1–3, Q is a divalent group; and k is 0 or 1.

Further, the present inventors have found that a Wittig's reaction has high selectivity and causes hardly any side reaction and that purification by such means as column chromatography or distillation is not necessary. In this case, since washing with water is sufficient for removal of impurities, such as excess starting materials, this reaction is favorable to the industrialization.

That is, the present invention is characterized in that the silane compound represented by general formula I is synthesized by any one of Method A and Method B, which are described below.

Method A:

Method A is a method for making the silane compound of claim 3 by reacting a compound represented by general formula A with a compound represented by general formula B in the presence of a base:

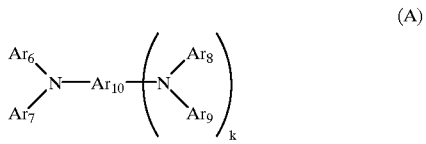

(A)

where

Ar$_6$–Ar$_9$ are independently substituted or unsubstituted aryl groups;

Ar$_{10}$ is a substituted or unsubstituted aryl or arylene group, provided that one to four of Ar$_6$–Ar$_{10}$ have a substituent represented by —CHO or —CH$_2$L where L stands for PM(R$_3$)$_2$ or Hal$^-$ P(R$_3$)$_3^+$ where Hal stands for a halogen atom, M stands for O or S, R$_3$ is selected from the group consisting of alkyl, phenyl, alkoxy and amino groups, and k is 0 or 1

T—Y$^1$—SiR$_{1(3-a)}$(OR$_2$)$_a$ (B)

where

R$_1$ is selected from the group consisting of hydrogen, alkyl, substituted and unsubstituted aryl groups;

R$_2$ is selected from the group consisting of hydrogen, alkyl, and trialkylsilyl groups;

a is an integer of 1–3;

Y$^1$ is a divalent group containing at least one group selected from the group consisting of —C$_x$H$_{2x}$— (where x is an integer of 1–15), —C$_{x'}$H$_{2x'-2}$— (where x' is an integer of 2–15), —C$_{x''}$H$_{2x''-4}$— (wherein x" is an integer of 2–15) a substituted or unsubstituted arylene group, —CH=N—, —O—, and —COO—;

T is —CH$_2$L in the case where general formula A has —CHO but —CHO in the case where general formula A has —CH$_2$L where L stands for PM(R$_3$)$_2$ or Hal$^-$ P(R$_3$)$_3^+$ where Hal stands for a halogen atom, M stands for O or S and R$_3$ is selected from the group consisting of alkyl, phenyl, alkoxy and amino groups.

Method B:

Method B is a method for making the silane compound of claim 4 by reacting a compound represented by general formula A' with a compound represented by general formula B' in the presence of an acid,

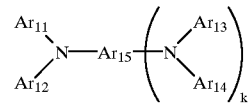

(A')

where

Ar$_{11}$–Ar$_{15}$ are independently substituted or unsubstituted aryl groups;

Ar$_{15}$ is a substituted or unsubstituted aryl or arylene group, provided that one to four of Ar$_{11}$–Ar$_{15}$ have a substituent represented by —CHO or —Y$^2$—NH$_2$ where Y$^2$ is a divalent group containing at least one group selected from the group consisting of —C$_x$H$_{2x}$— (where x is an integer of 1–15), —C$_{x'}$H$_{2x'-2}$— (where x' is an integer of 2–15), —C$_{x''}$H$_{2x''-4}$— (where x" is an integer of 2–15), a substituted or unsubstituted arylene group, —CH=N— —O— and —COO—; and k is 0 or 1.

T—Y$^2$—SiR$_{1(3-a)}$(OR$_2$)$_a$ (B')

where

R$_1$ is selected from the group consisting of hydrogen, alkyl, substituted and unsubstituted aryl groups;

R$_2$ is selected from the group consisting of hydrogen, alkyl, and trialkylsilyl groups;

a is an integer of 1–3;

Y$^2$ is the divalent group;

T is —Y$^2$—NH$_2$ in general formula A' has —CHO but —CHO in the case where general formula A has —Y$^2$—NH$_2$.

Another object of the present invention is to provide an electrophotographic photoreceptor, which photoreceptor has superior mechanical strength, sensitivity, and stability to environmental conditions, by forming a tough film utilizing a compound which has superior solubility, film formability and compatibility.

After studies aiming at the above-mentioned objectives, the present inventors have found that an electrophotographic photoreceptor has superior solubility and film-forming capability if the photoreceptor comprises a plurality of layers wherein at least one of the plural layers contains a specific silane compound. Particularly, they have found that the use of a silane compound, which has no hydrogen atom directly linked to a heteroatom so that the tendency to adsorb moisture in the atmosphere is reduced and therefore the susceptivity to the influence of the discharge products or humidity is reduced, makes it possible to provide an electrophotographic photoreceptor having a superior stability to the environmental conditions.

That is, the electrophotographic photoreceptor according to the present invention comprises a plurality of layers wherein at least one of the plural layers contains at least one silane compound represented by general formula I,

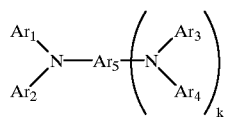

(I)

where

Ar$_1$–Ar$_4$ are independently substituted or unsubstituted aryl groups;

Ar$_5$ is a substituted or unsubstituted aryl or arylene group, provided that one to four of Ar$_1$–Ar$_5$ have a substituent represented by —Q—SiR$_{1(3-a)}$(OR$_2$)$_a$ where R$_1$ is selected from the group consisting of hydrogen, alkyl, and substituted and unsubstituted aryl groups;

R$_2$ is selected from the group consisting of hydrogen, alkyl, and trialkylsilyl groups;

a is an integer of 1–3, Q is a divalent group; and k is 0 or 1.

Another electrophotographic photoreceptor according to the present invention comprises the layer, which contains at least one silane compound represented by general formula I, further incorporated with a fluorine-containing compound such as a fluorine-containing silane coupling agent.

DESCRIPTION OF THE PREFERRED EMBODIMENT(S)

Figure 1:
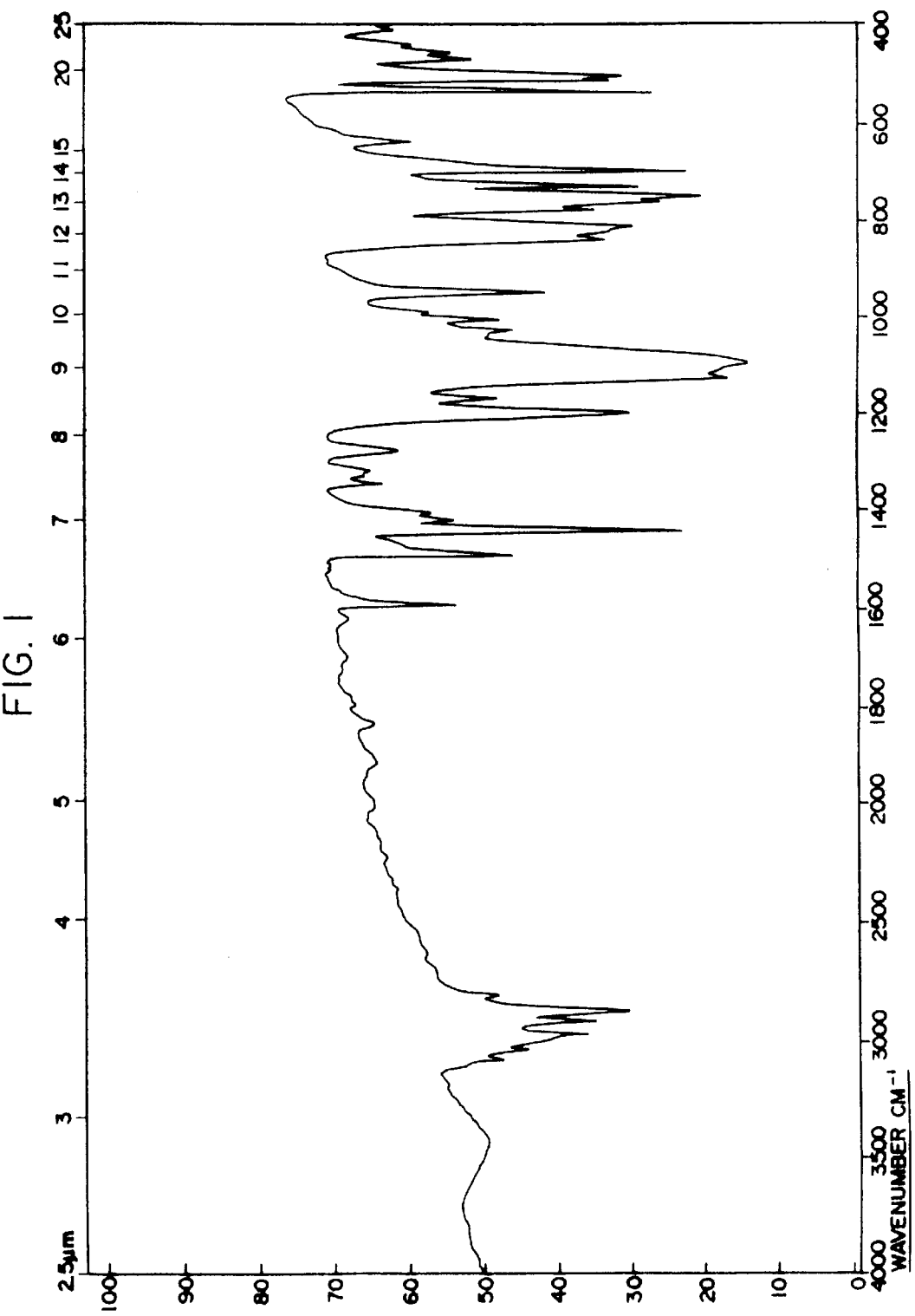
FIG. 1 shows the IR absorption spectrum of the phosphonium salt prepared in Synthesis 1.

Details of the present invention are given below.

Silane compounds are represented by general formula I.

In general formula I, Ar$_1$–Ar$_4$ are independently substituted or unsubstituted aryl groups; Ar$_5$ is a substituted or unsubstituted aryl or arylene group, provided that one to four of Ar$_1$–Ar$_5$ have a substituent represented by —Q—SiR$_{1(3-a)}$(OR$_2$)$_a$ where R$_1$ is selected from the group consisting of hydrogen, alkyl, substituted, and unsubstituted aryl groups, R$_2$ is selected from the group consisting of hydrogen, alkyl and trialkylsilyl groups, a is an integer of 1–3; Q is a divalent group, provided that the divalent group, Q, does not include a divalent group containing a hydrogen atom attached directly to a hetero atom, i.e., —CONH—, —NH— and the like; and k is 0 or 1.

Particularly, it is preferable that Q be a divalent group containing at least one group selected from the group consisting of —C$_x$H$_{2x}$— (where x is an integer of 1–17), —C$_{x'}$H$_{2x'-2}$— (where x' is an integer of 2–17), —C$_{x''}$H$_{2x''-4}$— (where x'' is an integer of 2–17), a substituted or unsubstituted arylene group, —CH=N—, and —O—.

More preferably, Q is —CH=CH—Y$^1$— where Y$^1$ is a divalent group containing at least one group selected from the group consisting of —C$_x$H$_{2x}$— (where x is an integer of 1–15); —C$_{x'}$H$_{2x'-2}$— (where x' is an integer of 2–15); —C$_{x''}$H$_{2x''-4}$— (where x'' is an integer of 2–15); a substituted or unsubstituted arylene group; —CH=N—; and —O—.

Further, Q is preferably —CH=N—Y$^2$— where Y$^2$ is a divalent group containing at least one group selected from the group consisting of —C$_x$H$_{2x}$— (where x is an integer of 1–15), —C$_{x'}$H$_{2x'-2}$— (where x' is an integer of 2–15), —C$_{x''}$H$_{2x''-4}$— (where x'' is an integer of 2–15), a substituted or unsubstituted arylene group, —CH=N— and —O—.

More preferably, Q is —CH$_2$CH$_2$—Y$^3$— where Y$^3$ is a divalent group containing at least one group selected from the group consisting of —C$_x$H$_{2x}$— (where x is an integer of 1–15), —C$_{x'}$—H$_{2x'-2}$— (where x' is an integer of 2–15), —C$_{x''}$H$_{2x''-4}$— (where x'' is an integer of 2–15), a substituted or unsubstituted arylene group, —CH=N— and —O—.

In general formula I, Ar$_1$–Ar$_4$ are independently substituted or unsubstituted aryl groups, examples of which include the following:

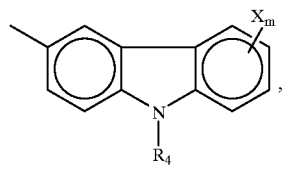

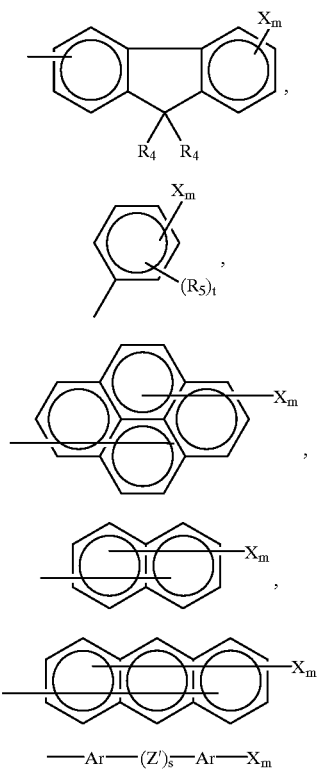

In general formula I, k is 0 or 1 and Ar$_5$ stands for a substituted or unsubstituted aryl or arylene group, examples of which include the following:

where k = 0

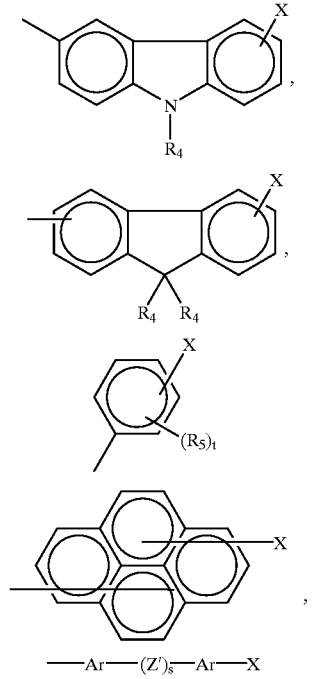

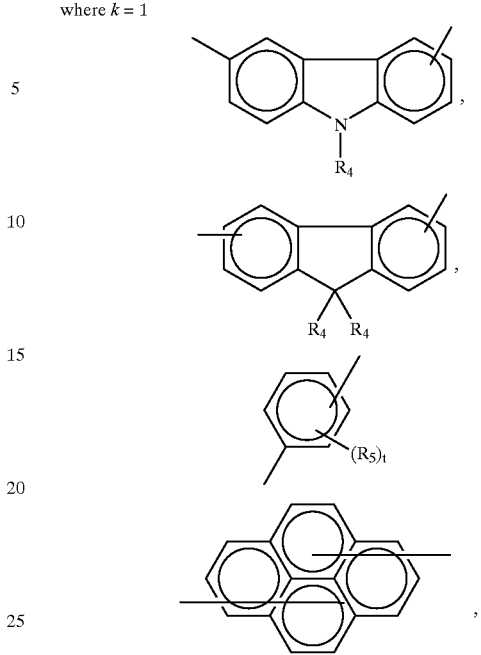

—Ar—(Z')$_s$—Ar—

In the above-described formulas, X is selected from the group consisting of —CH=CH—Y$^1$—SiR$_{1(3-a)}$(OR$_2$)$_a$, —CH=N—Y$^2$—SiR$_{1(3-a)}$(OR$_2$)$_a$, and —CH$_2$CH$_2$—Y$^3$—SiR$_{1(3-a)}$(OR$_2$)$_a$, where Y$^1$–Y$^3$ are independently selected from divalent groups, examples of which include the following:

—(CH$_2$)$_x$—, —(C$_{x'}$H$_{2x'-2}$)—, —(C$_{x''}$H$_{2x''-4}$)—,
—COO—, —N=CH—, —O—

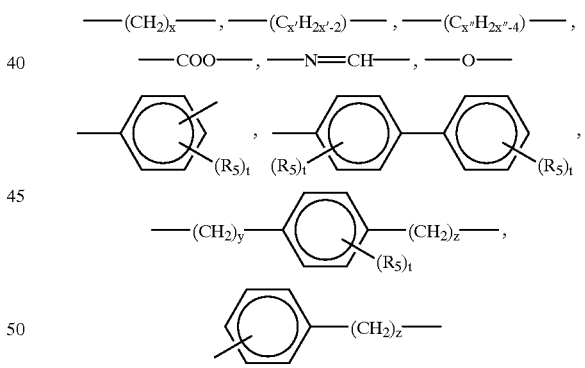

Among these groups, the following groups are particularly preferable:

—(CH$_2$)$_x$—, —(C$_{x'}$H$_{2x'-2}$)—, —(C$_{x''}$H$_{2x''-4}$)—,

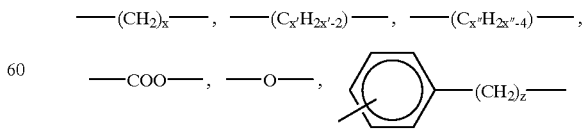

It is necessary that one to four of the above-mentioned Ar$_1$–Ar$_5$ have a substituent represented by a formula selected from the group consisting of —CH=CH—Y$^1$—SiR$_{1(3-a)}$(OR$_2$)$_a$, —CH=N—Y$^2$—SiR$_{1(3-a)}$(OR$_2$)$_a$, and —CH$_2$CH$_2$—Y$^3$—SiR$_{1(3-a)}$(OR$_2$)$_a$.

Ar may be selected from the following groups:

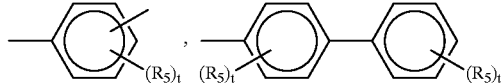

Z' may be selected from the following groups:

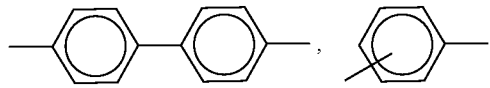

Z may be selected from the following groups:

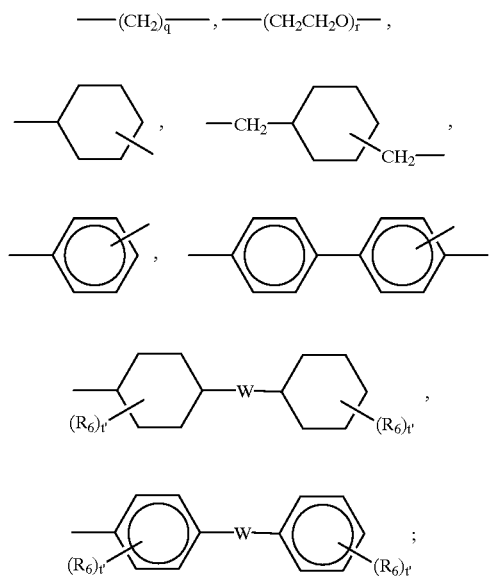

W may be selected from the following groups:

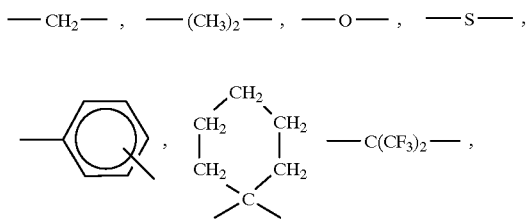

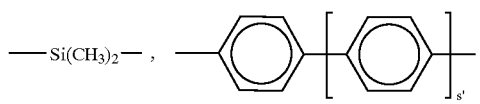

R$^4$ is selected from the group consisting of hydrogen, an alkyl group having 1 to 4 carbon atoms, an unsubstituted phenyl group, a phenyl group substituted with an alkyl group having 1 to 4 carbon atoms or with an alkoxy group having 1 to 4 carbon atoms, and an aralkyl group having 7 to 10 carbon atoms. R$^5$ is selected from the group consisting of hydrogen, an alkyl group having 1 to 4 carbon atoms, an alkoxy group having 1 to 4 carbon atoms, and a halogen atom. R$^1$ is selected from the group consisting of hydrogen, an alkyl group having 1 to 10 carbon atoms, an unsubstituted aryl group, and an aryl group substituted with an alkyl group having 1 to 4 carbon atoms or with an alkoxy group having 1 to 4 carbon atoms. R$^2$ is selected from the group consisting of hydrogen, an alkyl group having 1 to 4 carbon atoms and a trialkylsilyl group substituted with an alkyl group having 1 to 4 carbon atoms. R$^6$ is selected from the group consisting of hydrogen and an alkyl group having 1 to 4 carbon atoms. m and s are each 0 or 1, t and a are each an integer of 1–3, and y and z are each an integer of 1–5. x is an integer of 1–15, and x' and x" are each an integer of 2–15. t is an integer of 1 or 2, s' is an integer of 0–3, and q and r are each an integer of 1–10.

Preferably, at least one of Ar$_1$–Ar$_5$ has at least two conjugated aromatic groups to enhance the stability against the influence of photooxidation.

More preferably, Ar$_5$ is selected from the following groups:

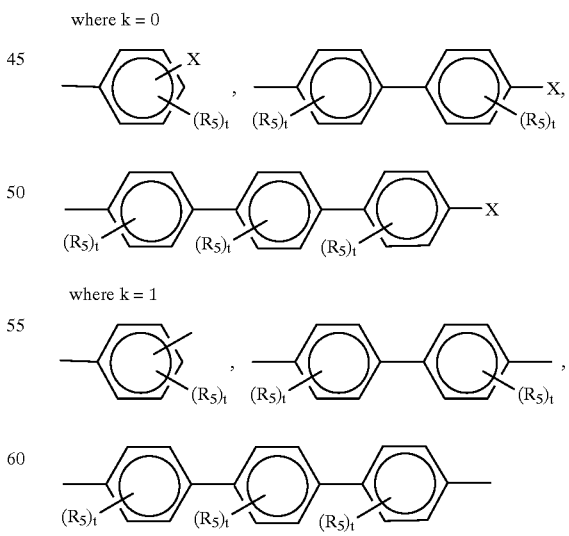

Concrete examples of the silane compounds of general formula I are shown in Tables 1–4.

TABLE 1
| Compound | k | Ar$_1$ | Ar$_2$ | Ar$_3$ | Ar$_4$ | Ar$_5$ | X |
|---|---|---|---|---|---|---|---|
| 1 | 0 | 2,4-diMe-phenyl | biphenyl | — | — | 4-X-phenyl | —CH=CH—(CH$_2$)$_2$—Si(OMe)$_3$ |
| 2 | 0 | 2,6-diMe-4-OMe-phenyl | biphenyl | — | — | 4-X-phenyl | —CH=CH—(CH$_2$)$_2$—Si(OMe)$_3$ |
| 3 | 0 | 2,4-diMe-phenyl | biphenyl | — | — | 4-X-phenyl | —CH=CH—(CH$_2$)$_2$—Si(OEt)$_3$ |
| 4 | 0 | 2,4-diMe-phenyl | biphenyl | — | — | 4-X-phenyl | —CH=CH—CH$_2$—Si(OMe)$_2$Me |
| 5 | 0 | 2,4-diMe-phenyl | biphenyl | — | — | 4-X-phenyl | —CH=CH—C$_6$H$_4$—(CH$_2$)$_2$—Si(OMe)$_2$ |

TABLE 1-continued

| Compound | k | Ar₁ | Ar₂ | Ar₃ | Ar₄ | Ar₅ | X |
|---|---|---|---|---|---|---|---|
| 6 | 0 | 2,4-dimethylphenyl | biphenyl | — | — | phenyl | —CH=CH—Si(OEt)₂— |
| 7 | 0 | 2,4-dimethylphenyl | biphenyl | — | — | phenyl | —CH=CH—C₆H₄—Si(OMe)₂ |
| 8 | 0 | 2,4-dimethylphenyl | biphenyl | — | — | phenyl | —CH=CH—CH₃—Si(OEt)₃ |
| 9 | 1 | 2,4-dimethylphenyl | phenyl | phenyl-X | 2,4-dimethylphenyl | 3,5-dimethylbiphenyl | —CH=CH—(CH₂)₂—Si(OMe)₃ |
| 10 | 1 | 2,4-dimethylphenyl | phenyl | phenyl-X | 2,4-dimethylphenyl | biphenyl | —CH=CH—(CH₂)₂—Si(OMe)₃ |

TABLE 1-continued structure: Ar1\N(Ar2)-Ar5-(N(Ar3)Ar4)k

| Compound | k | Ar1 | Ar2 | Ar3 | Ar4 | Ar5 | X |
|---|---|---|---|---|---|---|---|
| 11 | 1 | 2,6-Me₂-4-OMe-phenyl | phenyl | 4-X-phenyl | 2,6-Me₂-4-OMe-phenyl | 3,3'-Me₂-biphenyl-4,4'-diyl | —CH=CH—(CH₂)₂—Si(OMe)₃ |
| 12 | 1 | 2,6-Me₂-4-OMe-phenyl | phenyl | 4-X-phenyl | 2,6-Me₂-4-OMe-phenyl | biphenyl-4,4'-diyl | —CH=CH—(CH₂)₂—Si(OMe)₃ |
| 13 | 1 | 4-Me-phenyl | phenyl | 4-X-phenyl | 4-Me-phenyl | 3,3'-Me₂-biphenyl-4,4'-diyl | —CH=CH—(CH₂)₂—Si(OMe)₃ |
| 14 | 0 | 2,4-Me₂-phenyl | 4-X-phenyl | — | — | 4-X-phenyl | —CH=CH—(CH₂)₂—Si(OMe)₃ |
| 15 | 0 | biphenyl-4-yl | 4-X-phenyl | — | — | 4-X-phenyl | —CH=CH—(CH₂)₂—Si(OMe)₃ |

TABLE 1-continued

| Compound | k | Ar₁ | Ar₂ | Ar₃ | Ar₄ | Ar₅ | X |
|---|---|---|---|---|---|---|---|
| 16 | 0 | 2,4-diMe-phenyl | 4-X-phenyl | — | — | 4-X-phenyl | —CH=CH—(CH₂)₂—Si(OEt)₃ |
| 17 | 0 | 2,4-diMe-phenyl | 4-X-phenyl | — | — | 4-X-phenyl | —CH=CH—CH₂—Si(OMe)₂Me |
| 18 | 0 | 2,4-diMe-phenyl | 4-X-phenyl | — | — | 4-X-phenyl | —CH=CH—C₆H₄—(CH₃)₂—Si(OMe)₃ |
| 19 | 0 | 2,4-diMe-phenyl | 4-X-phenyl | — | — | 4-X-phenyl | —CH=CH—Si(OEt)₃ |
| 20 | 0 | 2,4-diMe-phenyl | 4-X-phenyl | — | — | 4-X-phenyl | —CH=CH—C₆H₄—Si(OMe)₃ |
| 21 | 1 | 2,4-diMe-phenyl | 4-X-phenyl | 4-X-phenyl | 2,4-diMe-phenyl | 3,4-diMe-biphenyl | —CH=CH—(CH₂)₂—Si(OMe)₃ |

TABLE 1-continued

| Compound | k | Ar₁ | Ar₂ | Ar₃ | Ar₄ | Ar₅ | X |
|---|---|---|---|---|---|---|---|
| 22 | 1 | 3,4-Me₂-C₆H₃ | 4-X-C₆H₄ | 4-X-C₆H₄ | 3,4-Me₂-C₆H₃ | 4,4'-biphenyl | —CH=CH—(CH₂)₂—Si(OMe)₃ |
| 23 | 1 | 3,4-Me₂-C₆H₃ | 4-X-C₆H₄ | 4-X-C₆H₄ | 3,4-Me₂-C₆H₃ | 3,3'-Me₂-4,4'-biphenyl | —CH=CH—(CH₂)₂—Si(OEt)₃ |
| 24 | 1 | 3,4-Me₂-C₆H₃ | 4-X-C₆H₄ | 4-X-C₆H₄ | 3,4-Me₂-C₆H₃ | 4,4'-biphenyl | —CH=CH—CH₂—Si(OMe)₂Me |
| 25 | 1 | 3,4-Me₂-C₆H₃ | 4-X-C₆H₄ | 4-X-C₆H₄ | 3,4-Me₂-C₆H₃ | 3,3'-Me₂-4,4'-biphenyl | —CH=CH—C₆H₄—(CH₂)₂—Si(OMe)₃ |
| 26 | 1 | 3,4-Me₂-C₆H₃ | 4-X-C₆H₄ | 4-X-C₆H₄ | 3,4-Me₂-C₆H₃ | 3,3'-Me₂-4,4'-biphenyl | —CH=CH—Si(OEt)₃ |
| 27 | 1 | 3,4-Me₂-C₆H₃ | 4-X-C₆H₄ | 4-X-C₆H₄ | 3,4-Me₂-C₆H₃ | 3,3'-Me₂-4,4'-biphenyl | —CH=CH—C₆H₄—Si(OMe)₃ |

TABLE 1-continued

| Compound | k | Ar₁ | Ar₂ | Ar₃ | Ar₄ | Ar₅ | X |
|---|---|---|---|---|---|---|---|
| 28 | 1 | 3-Me-C₆H₄- | C₆H₄ | C₆H₄ | 3-Me-C₆H₄ | 3,3'-diMe-biphenyl | —CH=CH—CH₂—Si(OEt)₃ |
| 29 | 1 | C₆H₄-X | C₆H₄-X | C₆H₄-X | C₆H₄-X | 3,3'-diMe-biphenyl | —CH=CH—(CH₂)₂—Si(OMe)₃ |
| 30 | 1 | C₆H₄-X | C₆H₄-X | C₆H₄-X | C₆H₄-X | biphenyl | —CH=CH—(CH₂)₂—Si(OMe)₃ |
| 31 | 1 | C₆H₄-X | C₆H₄-X | C₆H₄-X | C₆H₄-X | terphenyl | —CH=CH—(CH₂)₂—Si(OMe)₃ |
| 32 | 1 | C₆H₄-X | C₆H₄-X | C₆H₄-X | C₆H₄-X | biphenyl | —CH=CH—CH₂—Si(OMe)₂Me |
| 33 | 1 | C₆H₄-X | C₆H₄-X | C₆H₄-X | C₆H₄-X | biphenyl | —CH=CH—C₆H₄—(CH₂)₂—Si(OMe)₃ |

TABLE 2

| Compound | k | Ar₁ | Ar₂ | Ar₃ | Ar₄ | Ar₅ | X |
|---|---|---|---|---|---|---|---|
| 34 | 0 | 2,4-dimethylphenyl | biphenyl | — | — | phenyl | —CH₂CH₂—(CH₃)₂—Si(OMe)₃ |
| 35 | 0 | 2,4-dimethylphenyl | biphenyl | — | — | phenyl | —CH₂CH₂—(CH₃)₂—Si(OEt)₃ |
| 36 | 0 | 2,4-dimethylphenyl | biphenyl | — | — | phenyl | —CH₂CH₂—Si(OEt)₃ |
| 37 | 0 | 2,4-dimethylphenyl | biphenyl | — | — | phenyl | —CH₂CH₂—(CH₃)₄—Si(OEt)₂Me |
| 38 | 0 | 2,4-dimethylphenyl | biphenyl | — | — | phenyl | —CH₂—CH₂—C₆H₄—Si(OMe)₃ |
| 39 | 0 | 2,4-dimethylphenyl | biphenyl | — | — | phenyl | —(CH₃)₂—C₆H₄—(CH₂)₂—Si(OMe)₃ |

TABLE 2-continued
| Compound | k | Ar₁ | Ar₂ | Ar₃ | Ar₄ | Ar₅ | X |
|---|---|---|---|---|---|---|---|
| 40 | 0 | 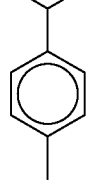 | 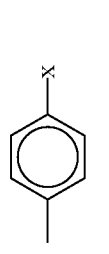 | — | — | 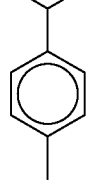 | —(CH₂)₃—Si(OEt)₃ |
| 41 | 1 | 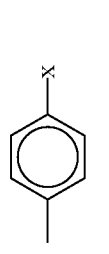 | 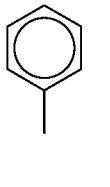 |  |  | 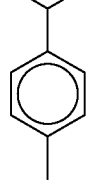 | —CH₂CH₂—(CH₂)₂—Si(OMe)₃ |
| 42 | 1 | 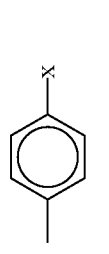 | 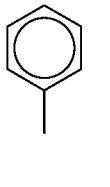 |  |  | 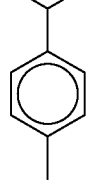 | —CH₂CH₂—(CH₂)₂—Si(OMe)₃ |
| 43 | 1 | 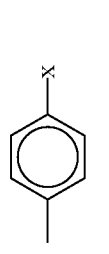 | 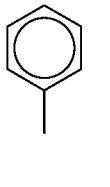 |  |  | 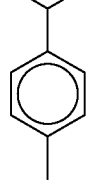 | —CH₂CH₂—(CH₂)₂—Si(OMe)₃ |
| 44 | 1 | 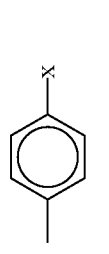 | 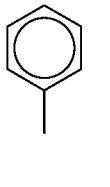 |  |  | 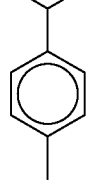 | —CH₂CH₂—(CH₂)₂—Si(OMe)₃ |
| 45 | 1 | 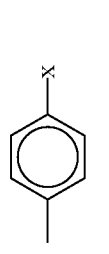 | 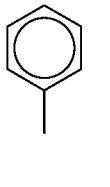 |  |  | | —CH₂CH₂—C₂H₄—Si(OMe)₃ |

TABLE 2-continued

| Compound | k | Ar₁ | Ar₂ | Ar₃ | Ar₄ | Ar₅ | X |
|---|---|---|---|---|---|---|---|
| 46 | 0 | 2,4-Me substituted phenyl | p-phenylene | — | — | p-phenylene | —CHCH₂—(CH₂)₂—Si(OMe)₃ |
| 47 | 0 | biphenyl | p-phenylene | — | — | p-phenylene | —CH₂CH₂—(CH₂)₂—Si(OMe)₃ |
| 48 | 0 | 2,4-Me substituted phenyl | p-phenylene | — | — | p-phenylene | —CH₂CH₂—(CH₂)₂—Si(OEt)₃ |
| 49 | 0 | 2,4-Me substituted phenyl | p-phenylene | — | — | p-phenylene | —CH₂CH₂—CH₂—Si(OMe)₂Me |
| 50 | 0 | 2,4-Me substituted phenyl | p-phenylene | — | — | p-phenylene | —CH₂CH₂—C₆H₄—Si(OMe)₃ |
| 51 | 1 | 2,4-Me substituted phenyl | p-phenylene | p-phenylene | 2,4-Me substituted phenyl | 3,5-Me substituted phenyl | —CH₂CH₂—(CH₂)₂—Si(OMe)₃ |
| 52 | 1 | 2,4-Me substituted phenyl | p-phenylene | p-phenylene | 2,4-Me substituted phenyl | p-phenylene (biphenyl) | —CH₂CH₂—(CH₂)₂—Si(OMe)₃ |

TABLE 2-continued

| Compound | k | Ar₁ | Ar₂ | Ar₃ | Ar₄ | Ar₅ | X |
|---|---|---|---|---|---|---|---|
| 53 | 1 | 3,4-dimethylphenyl | phenyl | phenyl | 2,4-dimethylphenyl | 3,3'-dimethyl-biphenyl | —CH₂CH₂—(CH₂)₂—Si(OEt)₃ |
| 54 | 1 | 3,4-dimethylphenyl | phenyl | phenyl | 2,4-dimethylphenyl | biphenyl | —CH₂CH₂—CH₂—Si(OMe)₂Me |
| 55 | 1 | 3,4-dimethylphenyl | phenyl | phenyl | 2,4-dimethylphenyl | 3,3'-dimethyl-biphenyl | —CH₂CH₂—C₆H₄—Si(OMe)₃ |
| 56 | 1 | 3,4-dimethylphenyl | phenyl | phenyl | 2,4-dimethylphenyl | 3,3'-dimethyl-biphenyl | —(CH₂)₂—Si(OEt)₃ |
| 57 | 1 | 3,4-dimethylphenyl | phenyl | phenyl | 2,4-dimethylphenyl | 3,3'-dimethyl-biphenyl | —(CH₃)₂—C₆H₄—(CH₂)₂—Si(OMe)₃ |
| 58 | 1 | 3,4-dimethylphenyl | phenyl | phenyl | 2,4-dimethylphenyl | 3,3'-dimethyl-biphenyl | —(CH₂)₃—Si(OEt)₃ |
| 59 | 0 | phenyl-X | phenyl | — | — | phenyl-X | —CH₂CH₂—(CH₃)₂—Si(OMe)₃ |

TABLE 2-continued
| Compound | k | Ar₁ | Ar₂ | Ar₃ | Ar₄ | Ar₅ | X |
|---|---|---|---|---|---|---|---|
| 60 | 0 | 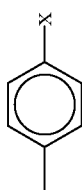 |  | — | — | 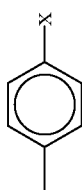 | —CH₂CH₂—(CH₂)₂—Si(OMe)₃ |
| 61 | 0 |  | 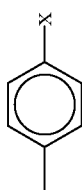 | — | — |  | —CH₂CH₂—(CH₂)₂—Si(OEt)₃ |
| 62 | 0 | 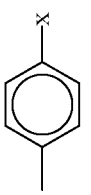 | 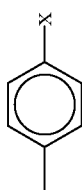 | — | — |  | —CH₂CH₂—CH₂—Si(OMe)₂Me |
| 63 | 0 | 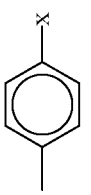 | 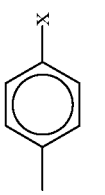 | — | — |  | —CH₂CH₂—C₆H₄—Si(OMe)₃ |
| 64 | 1 | 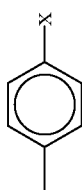 |  | 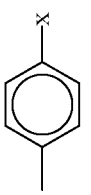 | 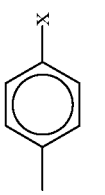 |  | —CH₂CH₂—(CH₂)₂—Si(OMe)₃ |
| 65 | 1 | 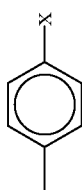 |  | 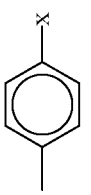 | 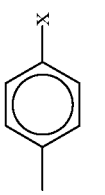 |  | —CH₂CH₂—(CH₂)₂—Si(OMe)₃ |
| 66 | 1 | 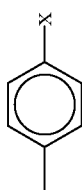 |  | 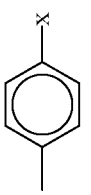 | 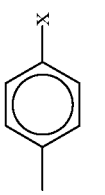 |  | —CH₂CH₂—(CH₂)₂—Si(OMe)₃ |

TABLE 2-continued

| Compound | k | Ar₁ | Ar₂ | Ar₃ | Ar₄ | Ar₅ | X |
|---|---|---|---|---|---|---|---|
| 67 | 1 | phenyl-X | phenyl-X | phenyl-X | phenyl-X | biphenyl | —CH₂CH₂—CH₂—Si(OMe)₂Me |
| 68 | 1 | phenyl-X | phenyl-X | phenyl-X | phenyl-X | biphenyl | —CH₂CH₂—C₆H₄—Si(OMe)₃ |

TABLE 3

| Compound | k | Ar₁ | Ar₂ | Ar₃ | Ar₄ | Ar₅ | X |
|---|---|---|---|---|---|---|---|
| 71 | 0 | 2,4-dimethylphenyl | biphenyl | — | — | 4-phenyl | —CH=N—(CH₂)₃—Si(OMe)₂ |
| 72 | 0 | 2,4-dimethylphenyl | biphenyl | — | — | 4-phenyl | —CH=N—(CH₂)₃—Si(OEt)₂ |
| 73 | 0 | 2,4-dimethylphenyl | biphenyl | — | — | 4-phenyl | —CH=N—CH₂—Si(OMe)₂Me |
| 74 | 0 | 2,4-dimethylphenyl | biphenyl | — | — | 4-phenyl | —CH=N—C₆H₄—(CH₂)₂—Si(OMe)₃ |
| 75 | 1 | 2,4-dimethylphenyl | phenyl | 4-phenyl | 2,4-dimethylphenyl | 3,5-dimethylphenyl | —CH=N—(CH₂)₃—Si(OMe)₃ |
| 76 | 1 | 2,4-dimethylphenyl | phenyl | 4-phenyl | 2,4-dimethylphenyl | 4-phenyl | —CH=N—(CH₂)₃—Si(OMe)₃ |

TABLE 3-continued
| Compound | k | Ar₁ | Ar₂ | Ar₃ | Ar₄ | Ar₅ | X |
|---|---|---|---|---|---|---|---|
| 77 | 1 |  | 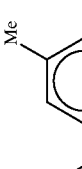 |  |  |  | —CH=N—(CH₂)₃<br>—Si(OMe)₃ |
| 78 | 1 |  | 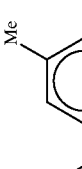 |  |  |  | —CH=N—(CH₂)₃<br>—Si(OMe)₃ |
| 79 | 1 |  | 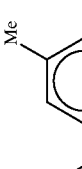 |  |  |  | —CH=N—(CH₂)₃<br>—Si(OMe)₃ |
| 80 | 0 |  | 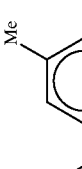 | — | — |  | —CH=N—(CH₂)₃<br>—Si(OMe)₃ |
| 81 | 0 |  |  | — | — |  | —CH=N—(CH₂)₃<br>—Si(OMe)₃ |
| 82 | 0 | 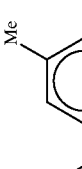 |  | — | — |  | —CH=N—(CH₂)₃<br>—Si(OEt)₃ |

TABLE 3-continued

| Compound | k | Ar₁ | Ar₂ | Ar₃ | Ar₄ | Ar₅ | X |
|---|---|---|---|---|---|---|---|
| 83 | 0 | 2,4-dimethylphenyl | p-phenylene | — | — | p-phenylene | —CH=N—CH₂—Si(OMe)₂Me |
| 84 | 0 | 2,4-dimethylphenyl | p-phenylene | — | — | p-phenylene | —CH=N—C₆H₄—(CH₂)₂—Si(OMe)₃ |
| 85 | 1 | 2,4-dimethylphenyl | p-phenylene | p-phenylene | 2,4-dimethylphenyl | 3,3'-dimethylbiphenyl | —(CH₂)₃—Si(OMe)₃ |
| 86 | 1 | 2,4-dimethylphenyl | p-phenylene | p-phenylene | 2,4-dimethylphenyl | 3,3'-dimethylbiphenyl | —CH=N—(CH₂)₃—Si(OEt)₃ |
| 87 | 1 | 2,4-dimethylphenyl | p-phenylene | p-phenylene | 2,4-dimethylphenyl | biphenyl | —CH=N—CH₂—Si(OMe)₂Me |
| 88 | 1 | 2,4-dimethylphenyl | p-phenylene | p-phenylene | 2,4-dimethylphenyl | 3,3'-dimethylbiphenyl | —CH=N—C₆H₄—(CH₂)₂—Si(OMe)₃ |
| 89 | 0 | p-phenylene | p-phenylene | — | — | p-phenylene | —(CH₂)₃—Si(OMe)₃ |

TABLE 3-continued
| Compound | k | Ar₁ | Ar₂ | Ar₃ | Ar₄ | Ar₅ | X |
|---|---|---|---|---|---|---|---|
| 90 | 0 | 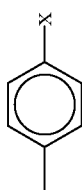 |  | — | — |  | —CH=N—(CH₂)₃<br>—Si(OMe)₃ |
| 91 | 0 |  | 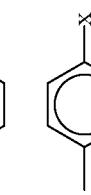 | — | — |  | —CH=N—(CH₂)₃<br>—Si(OEt)₃ |
| 92 | 0 | 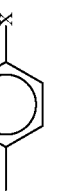 |  | — | — | 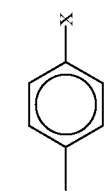 | —CH=N—CH₂<br>—Si(OMe)₂Me |
| 93 | 0 |  | 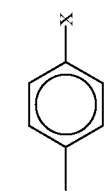 | — | — |  | —CH=N—C₆H₄—<br>(CH₂)₂—Si(OMe)₃ |
| 94 | 1 | 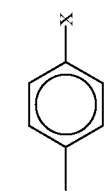 |  |  |  |  | —CH=N—(CH₂)₃<br>—Si(OMe)₃ |
| 95 | 1 |  |  |  |  |  | —CH=N—(CH₂)₃<br>—Si(OMe)₃ |
| 96 | 1 |  | | | | | —CH=N—(CH₂)₃<br>—Si(OMe)₃ |

TABLE 3-continued
| Compound | k | Ar₁ | Ar₂ | Ar₃ | Ar₄ | Ar₅ | X |
|---|---|---|---|---|---|---|---|
| 97 | 1 | 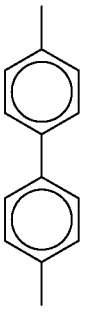 |  |  |  |  | —CH=N—CH₂—Si(OMe)₂Me |
| 98 | 1 |  |  |  |  |  | —CH=N—C₆H₄—(CH₂)₂—Si(OMe)₃ |

TABLE 4

| Compound | k | Ar₁ | Ar₂ | Ar₃ | Ar₄ | Ar₅ | X |
|---|---|---|---|---|---|---|---|
| 101 | 0 | 2,4-dimethylphenyl | 4-biphenyl | — | — | 4-phenyl | —O—(CH₂)₃—Si(OEt)₃ |
| 102 | 1 | 2,4-dimethylphenyl | 4-biphenyl | 4-phenyl | 2,4-dimethylphenyl | 3,4-dimethyl-4'-biphenyl | —CH=CH—(CH₃)₂—Si(OMe)₃ |
| 103 | 1 | 2,4-dimethylphenyl | 4-biphenyl | 4-phenyl | 2,4-dimethylphenyl | 3,4-dimethyl-4'-biphenyl | —CH=N—(CH₃)₂—Si(OMe)₃ |
| 104 | 1 | 2,4-dimethylphenyl | 4-phenyl | 4-phenyl | 2,4-dimethylphenyl | 3,4-dimethyl-4'-biphenyl | —CH=CH—CH₂—Si(OMe)₂Me |
| 105 | 1 | 2,4-dimethylphenyl | 4-phenyl | 4-phenyl | 2,4-dimethylphenyl | 3,4-dimethyl-4'-biphenyl | —O—(CH₂)₃—Si(OEt)₃ |
| 106 | 0 | 4-phenyl | 4-phenyl | — | — | 4-phenyl | —CH=CH—(CH₃)₂—Si(OMe)₃ |
| 107 | 0 | 4-phenyl | 4-phenyl | — | — | 4-phenyl | —CH=N—(CH₃)₂—Si(OMe)₃ |

TABLE 4-continued

| Compound | k | Ar$_1$ | Ar$_2$ | Ar$_3$ | Ar$_4$ | Ar$_5$ | X |
|---|---|---|---|---|---|---|---|
| 108 | 0 | 4-X-C$_6$H$_4$– | 4-X-C$_6$H$_4$– | — | — | 4-X-C$_6$H$_4$– | —(CH$_2$)$_2$—Si(OEt)$_2$ |
| 109 | 0 | 4-X-C$_6$H$_4$– | 4-X-C$_6$H$_4$– | — | — | 4-X-C$_6$H$_4$– | —O—(CH$_2$)$_2$—Si(OMe)$_2$Me |
| 110 | 1 | 4-X-C$_6$H$_4$– | 4-X-C$_6$H$_4$– | 4-X-C$_6$H$_4$– | 4-X-C$_6$H$_4$– | 3,3'-Me$_2$-biphenyl-4-yl | —(CH$_2$)$_2$—Si(OEt)$_3$ |
| 111 | 1 | 4-X-C$_6$H$_4$– | 4-X-C$_6$H$_4$– | 4-X-C$_6$H$_4$– | 4-X-C$_6$H$_4$– | 3,3'-Me$_2$-biphenyl-4-yl | —O—(CH$_2$)$_2$—Si(OMe)$_2$Me |
| 201 | 0 | 3,4-Me$_2$-C$_6$H$_3$– | 3,4-Me$_2$-C$_6$H$_3$– | — | — | 4-X-C$_6$H$_4$– | —COO—(CH$_3$)$_3$—Si(OMe)$_3$ |
| 202 | 0 | 3,4-Me$_2$-C$_6$H$_3$– | 3,4-Me$_2$-C$_6$H$_3$– | — | — | 4-X-C$_6$H$_4$– | —COO—CH$_2$C$_6$H$_4$—(CH$_3$)$_2$—Si(OMe)$_3$ |
| 203 | 0 | 3,4-Me$_2$-C$_6$H$_3$– | 3,4-Me$_2$-C$_6$H$_3$– | — | — | 4-X-C$_6$H$_4$– | —CH$_2$—COO—(CH$_2$)$_3$—Si(OMe)$_3$ |

TABLE 4-continued

| Compound | k | Ar₁ | Ar₂ | Ar₃ | Ar₄ | Ar₅ | X |
|---|---|---|---|---|---|---|---|
| 204 | 0 | 2,4-Me₂-C₆H₃ | 2,4-Me₂-C₆H₃ | — | — | p-C₆H₄ | —CH₂—COO—CH₂C₆H₄—(CH₂)₂—Si(OMe)₃ |
| 205 | 0 | 2,4-Me₂-C₆H₃ | 2,4-Me₂-C₆H₃ | — | — | p-C₆H₄ | —(CH₃)₂—COO—(CH₃)₂—Si(OMe)₃ |
| 206 | 0 | 2,4-Me₂-C₆H₃ | 2,4-Me₂-C₆H₃ | — | — | p-C₆H₄ | —(CH₂)₂—COO—CH₂C₆H₄—(CH₃)₂—Si(OMe)₃ |
| 207 | 0 | 2,4-Me₂-C₆H₃ | 4-biphenyl | — | — | p-C₆H₄ | —COO—(CH₂)₃—Si(OMe)₃ |
| 208 | 0 | 2,4-Me₂-C₆H₃ | 4-biphenyl | — | — | p-C₆H₄ | —COO—CH₂C₆H₄—(CH₂)₂—Si(OMe)₃ |
| 209 | 0 | 2,4-Me₂-C₆H₃ | 4-biphenyl | — | — | p-C₆H₄ | —CH₂—COO—(CH₂)₃—Si(OMe)₃ |
| 210 | 0 | 2,4-Me₂-C₆H₃ | 4-biphenyl | — | — | p-C₆H₄ | —CH₂—COO—CH₂C₆H₄—(CH₂)₂—Si(OMe)₃ |

TABLE 4-continued
| Compound | k | Ar$_1$ | Ar$_2$ | Ar$_3$ | Ar$_4$ | Ar$_5$ | X |
|---|---|---|---|---|---|---|---|
| 211 | 0 |  |  | — | — |  | —(CH$_2$)$_2$—COO—(CH$_2$)$_3$—Si(OMe)$_3$ |
| 212 | 0 |  |  | — | — |  | —(CH$_2$)$_2$—COO—CH$_2$C$_6$H$_4$—(CH$_2$)$_2$—Si(OMe)$_3$ |
| 213 | 0 |  |  | — | — |  | —COO—(CH$_2$)$_3$—Si(OMe)$_3$ |
| 214 | 0 |  |  | — | — |  | —COO—CH$_2$C$_6$H$_4$—(CH$_2$)$_2$—Si(OMe)$_3$ |
| 215 | 0 |  |  | — | — |  | —(CH$_2$)$_2$—COO—(CH$_2$)$_3$—Si(OMe)$_3$ |
| 216 | 0 |  |  | — | — |  | —(CH$_2$)$_2$—COO—CH$_2$C$_6$H$_4$—(CH$_2$)$_2$—Si(OMe)$_3$ |

TABLE 4-continued

| Compound | k | Ar₁ | Ar₂ | Ar₃ | Ar₄ | Ar₅ | X |
|---|---|---|---|---|---|---|---|
| 217 | 0 | 2,4-diMe-phenyl | 2,4-diMe-phenyl | — | — | biphenyl | —COO—(CH₂)₃—Si(OMe)₃ |
| 218 | 0 | 2,4-diMe-phenyl | 2,4-diMe-phenyl | — | — | biphenyl | —COO—CH₂—C₆H₄Si(OMe)₃ |
| 219 | 0 | 2,4-diMe-phenyl | phenyl | — | — | biphenyl | —COO—(CH₂)₃—Si(OMe)₃ |
| 220 | 0 | 2,4-diMe-phenyl | phenyl | — | — | biphenyl | —COO—(CH₂)₃—Si(OMe)₃ |
| 221 | 0 | phenyl | X-phenyl | — | — | phenyl | —CH₂—COO—(CH₂)₃—Si(OMe)₃ |
| 222 | 0 | phenyl | X-phenyl | — | — | phenyl | —(CH₂)₂—COO—(CH₂)₃—Si(OMe)₃ |
| 223 | 0 | phenyl | X-phenyl | — | — | phenyl | —(CH₂)₂—COO—CH₂C₆H₄—(CH₂)₂—Si(OMe)₃ |
| 224 | 0 | 4-Me-phenyl | X-phenyl | — | — | phenyl | —CH₂—COO—CH₂C₆H₄—(CH₂)₂—Si(OMe)₃ |

TABLE 4-continued

| Compound | k | Ar₁ | Ar₂ | Ar₃ | Ar₄ | Ar₅ | X |
|---|---|---|---|---|---|---|---|
| 225 | 0 | 4-Me-C₆H₄- | -C₆H₄-X (para) | — | — | -C₆H₄-X (para) | —(CH₂)₂—COO—(CH₂)₃—Si(OMe)₃ |
| 226 | 0 | 4-Me-C₆H₄- | -C₆H₄-X (para) | — | — | -C₆H₄-X (para) | —(CH₂)₂—COO—CH₂C₆H₄—(CH₂)₂—Si(OMe)₃ |
| 227 | 0 | 2-Me-4-C₆H₃- | -C₆H₄-X (para) | — | — | -C₆H₄-X (para) | —CH₂—COO—CH₂C₆H₄—(CH₂)₂—Si(OMe)₃ |
| 228 | 0 | 2-Me-4-C₆H₃- | -C₆H₄-X (para) | — | — | -C₆H₄-X (para) | —(CH₂)₂—COO—(CH₂)₃—Si(OMe)₃ |
| 229 | 0 | 2-Me-4-C₆H₃- | -C₆H₄-X (para) | — | — | -C₆H₄-X (para) | —(CH₂)₂—COO—Si(OMe)₃ |
| 230 | 0 | 2-Me-4-C₆H₃- | -C₆H₄-X (para) | — | — | -C₆H₄-X (para) | —(CH₂)₂—COO—CH₂C₆H₄—(CH₂)₂—Si(OMe)₃ |
| 231 | 0 | 4,4'-biphenylyl | -C₆H₄-X (para) | — | — | -C₆H₄-X (para) | —CH₂—COO—(CH₂)₂—Si(OMe)₃ |

TABLE 4-continued
| Compound | k | Ar₁ | Ar₂ | Ar₃ | Ar₄ | Ar₅ | X |
|---|---|---|---|---|---|---|---|
| 232 | 0 |  |  | — | — |  | —(CH₂)₂—COO—(CH₂)₃—Si(OMe)₃ |
| 233 | 0 |  |  | — | — |  | —(CH₂)₂—COO—CH₂C₆H₄—Si(OMe)₃ |
| 234 | 0 |  |  | — | — |  | —COO—(CH₂)₃—Si(OMe)₃ |
| 235 | 0 |  |  | — | — |  | —COO—CH₂C₆H₄—(CH₂)₃—Si(OMe)₃ |
| 236 | 0 |  |  | — | — |  | —CH₂—COO—CH₂C₆H₄—Si(OMe)₃ |
| 237 | 0 |  | | — | — | | —(CH₂)₂—COO—(CH₂)₃—Si(OMe)₃ |
| 238 | 0 | | | — | — | | —(CH₂)₂—COO—CH₂C₆H₄—Si(OMe)₃ |
| 239 | 0 | | | — | — | | —(CH₂)₂—COO—(CH₂)₃—Si(OMe)₃ |

TABLE 4-continued

| Compound | k | Ar₁ | Ar₂ | Ar₃ | Ar₄ | Ar₅ | X |
|---|---|---|---|---|---|---|---|
| 240 | 0 | 2,4-dimethylphenyl | 3-substituted phenyl | — | — | 3-substituted phenyl | —(CH₂)₂—COO—CH₂C₆H₄—Si(OMe)₃ |
| 241 | 0 | 2,4-dimethylphenyl | 3-substituted phenyl | — | — | 3-substituted phenyl | —(CH₂)₂—COO—(CH₂)₂—Si(OMe)₃ |
| 242 | 0 | biphenyl | 3-substituted phenyl | — | — | 3-substituted phenyl | —CH₂—COO—(CH₂)₃—Si(OMe)₃ |
| 243 | 0 | biphenyl | 3-substituted phenyl | — | — | 3-substituted phenyl | —(CH₂)₂—COO—(CH₂)₃—Si(OMe)₃ |
| 244 | 0 | biphenyl | 3-substituted phenyl | — | — | 3-substituted phenyl | —(CH₂)₂—C₆H₄—(CH₂)₂—Si(OMe)₃ |
| 245 | 1 | 2,4-dimethylphenyl | 4-substituted phenyl | 4-substituted phenyl | 2,4-dimethylphenyl | 3,3'-dimethylbiphenyl | —COO—(CH₂)₃—Si(OMe)₃ |
| 246 | 1 | 2,4-dimethylphenyl | 4-substituted phenyl | 4-substituted phenyl | 2,4-dimethylphenyl | 3,3'-dimethylbiphenyl | —COO—CH₂C₆H₄—(CH₂)₂—Si(OMe)₃ |

TABLE 4-continued

| Compound | k | Ar₁ | Ar₂ | Ar₃ | Ar₄ | Ar₅ | X |
|---|---|---|---|---|---|---|---|
| 247 | 1 | 3,4-diMe-C₆H₃ | 1,4-C₆H₄ | 1,4-C₆H₄ | 3,4-diMe-C₆H₃ | 3,3',4,4'-tetraMe-biphenyl | —CH₂—COO—(CH₂)₃—Si(OMe)₃ |
| 248 | 1 | 3,4-diMe-C₆H₃ | 1,4-C₆H₄ | 1,4-C₆H₄ | 3,4-diMe-C₆H₃ | 3,3',4,4'-tetraMe-biphenyl | —CH₂—COO—CH₂C₆H₄—(CH₂)₂—Si(OMe)₃ |
| 249 | 1 | 3,4-diMe-C₆H₃ | 1,4-C₆H₄ | 1,4-C₆H₄ | 3,4-diMe-C₆H₃ | 3,3',4,4'-tetraMe-biphenyl | —(CH₂)₂—COO—(CH₂)₃—Si(OMe)₃ |
| 250 | 1 | 3,4-diMe-C₆H₃ | 1,4-C₆H₄ | 1,4-C₆H₄ | 3,4-diMe-C₆H₃ | 3,3',4,4'-tetraMe-biphenyl | —(CH₂)₂—COO—CH₂C₆H₄—(CH₂)₂—Si(OMe)₃ |
| 251 | 1 | C₆H₄ | 1,4-C₆H₄ | 1,4-C₆H₄ | C₆H₄ | 3,3',4,4'-tetraMe-biphenyl | —COO—CH₂C₆H₄—(CH₂)₂—Si(OMe)₃ |
| 252 | 1 | C₆H₄ | 1,4-C₆H₄ | 1,4-C₆H₄ | C₆H₄ | 3,3',4,4'-tetraMe-biphenyl | —CH₂—COO—(CH₂)₃—Si(OMe)₃ |
| 253 | 1 | C₆H₄ | 1,4-C₆H₄ | 1,4-C₆H₄ | C₆H₄ | 3,3',4,4'-tetraMe-biphenyl | —CH₂—COO—CH₂—C₆H₄—Si(OMe)₃ |

TABLE 4-continued

| Compound | k | Ar$_1$ | Ar$_2$ | Ar$_3$ | Ar$_4$ | Ar$_5$ | X |
|---|---|---|---|---|---|---|---|
| 254 | 1 | phenyl | phenyl-X | phenyl-X | phenyl | 3,4-dimethylbiphenyl | —CH$_2$—COO—CH$_2$C$_6$H$_4$—(CH$_2$)$_2$—Si(OMe)$_3$ |
| 255 | 1 | phenyl | phenyl-X | phenyl-X | phenyl | 3,4-dimethylbiphenyl | —(CH$_2$)$_2$—COO—(CH$_2$)$_3$—Si(OMe)$_3$ |
| 256 | 1 | phenyl | phenyl-X | phenyl-X | phenyl | 3,4-dimethylbiphenyl | —(CH$_2$)$_2$—COO—CH$_2$C$_6$H$_4$—Si(OMe)$_3$ |
| 257 | 1 | phenyl | biphenyl-X | biphenyl-X | phenyl | biphenyl | —COO—(CH$_2$)$_3$—Si(OMe)$_3$ |
| 258 | 1 | phenyl | biphenyl-X | biphenyl-X | phenyl | biphenyl | —COO—CH$_2$—C$_6$H$_4$—Si(OMe)$_3$ |
| 259 | 1 | phenyl | biphenyl-X | biphenyl-X | phenyl | biphenyl | —COO—CH$_2$C$_6$H$_4$—(CH$_2$)$_2$—Si(OMe)$_3$ |
| 260 | 1 | 2,4-dimethylphenyl | phenyl-X | phenyl-X | 2,4-dimethylphenyl | terphenyl | —COO—(CH$_2$)$_3$—Si(OMe)$_3$ |
| 261 | 1 | 2,4-dimethylphenyl | phenyl-X | phenyl-X | 2,4-dimethylphenyl | terphenyl | —COO—CH$_2$C$_6$H$_4$—Si(OMe)$_3$ |

TABLE 4-continued
| Compound | k | Ar₁ | Ar₂ | Ar₃ | Ar₄ | Ar₅ | X |
|---|---|---|---|---|---|---|---|
| 262 | 1 | 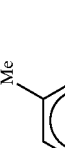 | 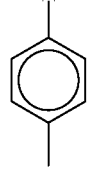 | 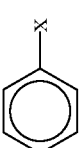 |  | 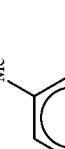 | —COO—CH₂C₆H₄—(CH₂)₂—Si(OMe)₃ |
| 263 | 1 | 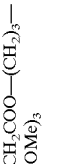 | 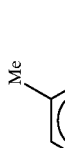 |  | 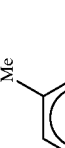 |  | —CH₂COO—(CH₂)₃—Si(OMe)₃ |
| 264 | 1 | 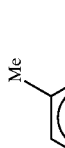 |  | 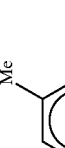 | 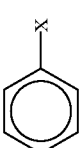 |  | —(CH₂)₂—COO—(CH₂)₃—Si(OMe)₃ |
| 265 | 1 | 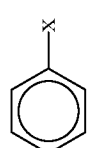 | 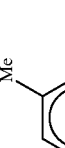 | 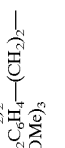 |  | 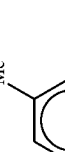 | —(CH₂)₂—COO—CH₂C₆H₄—(CH₂)₂—Si(OMe)₃ |

Where the silane compound of the present invention is used in the surface protective layer of an electrophotographic photoreceptor so that the surface protective layer is hardened, it is preferable that the silane compound comprise two or more of a silicon-containing substituent to obtain a film having a higher hardness.

The silane compound of general formula I, in which one to four of $Ar_1$–$Ar_5$ have a substituent represented by —CH=CH—$Y^1$—$SiR_{1(3-a)}(OR_2)_a$, can be synthesized by reacting a compound represented by general formula A with a compound represented by general formula B in the presence of a base in an inert gas atmosphere.

The silane compound of general formula I, in which one to four of $Ar_1$–$Ar_5$ have a substituent represented by —CH=N—$Y^2$—$SiR_{1(3-a)}(OR_2)_a$, can be synthesized by reacting a compound represented by general formula A' with a compound represented by general formula B' in the presence of an acid catalyst.

The substituents and numerals, which pertain to general formulas A, B, A', and B' and which are the same as those pertaining to general formula I, are each given the same symbols and an explanation is omitted.

$Ar_6$–$Ar_9$ of general formula A and $Ar_{11}$–$Ar_{14}$ of general formula A' are each independently a substituted or unsubstituted aryl group, examples of which include the following:

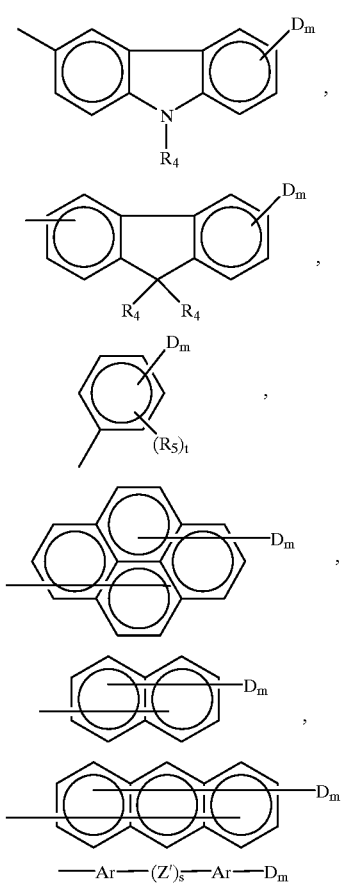

$Ar_{10}$ of general formula A and $Ar_{15}$ of general formula A' are each a substituted or unsubstituted aryl or arylene group, examples of which include the following:

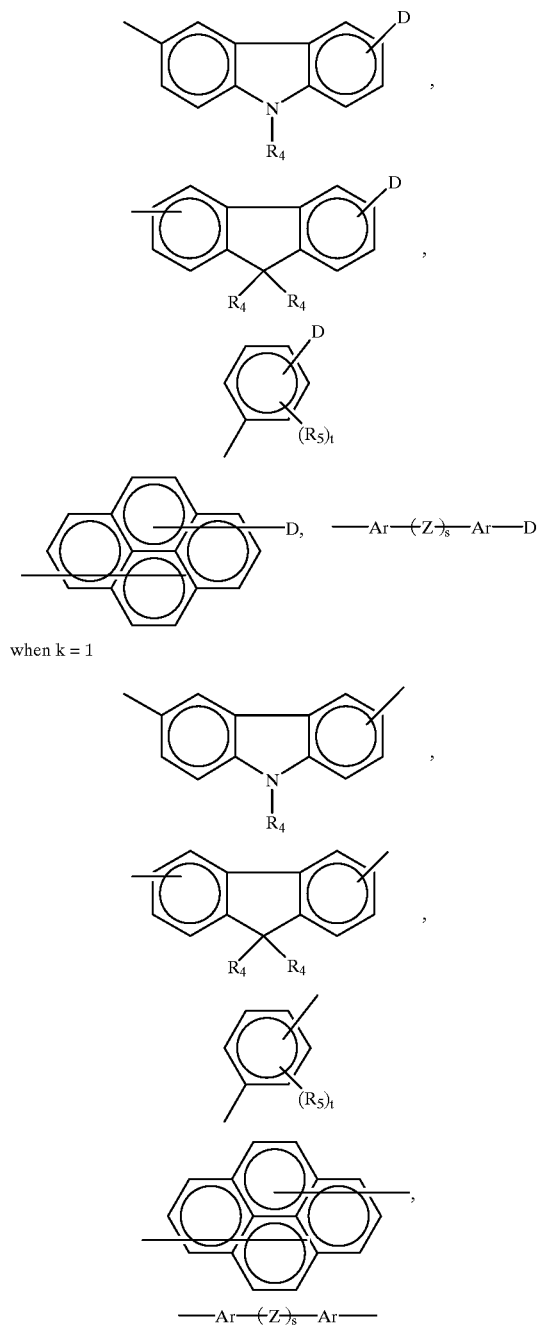

In the above-described formulas, D of $Ar_{10}$ in general formula A differs from D of $Ar_{15}$ in general formula A'. D of $Ar_{10}$ in general formula A is —CHO or —$CH_2L$ where L stands for $PM(R_3)_2$ or $Hal^-P(R_3)_3^+$ where Hal stands for a halogen atom, M stands for O or S, and $R_3$ is selected from the group consisting of $C_{(1-4)}$ alkyl, phenyl, $C_{(1-4)}$ alkoxy, and amino groups.

It is necessary that one to four of the above-mentioned $Ar_6$–$Ar_{10}$ have a substituent represented by —CHO or —$CH_2L$.

D of $Ar_{15}$ in general formula A' is —CHO or —$Y^2$—$NH_2$.

It is necessary that one to four of the above-mentioned $Ar_{11}$–$Ar_{15}$ have a substituent represented by —CHO or —$Y^2$—$NH_2$.

In general formula B, T stands for —$CH_2$ L in the case where general formula A has —CHO but stands for —CHO in the case where general formula A has —$CH_2$L.

In general formula B', T stands for —$Y^2$—$NH_2$ in the case where general formula A' has —CHO but stands for —CHO in the case where general formula A' has —$Y^2$—$NH_2$.

From the standpoint of ease in synthesis, the following conditions append to general formulas A, A', B, and B':

It is preferable that general formula A have a —CHO group (formyl group) {general formula $A_1$} and that general formula B have a —$CH_2$ L group (phosphorus compound group) {general formula $B_1$}.

It is also preferable that general formula A have a —CHO group (formyl group) {general formula $A'_1$} and that general formula B have a —$Y^2$—$NH_2$ group (amino group) {general formula $B'_1$}.

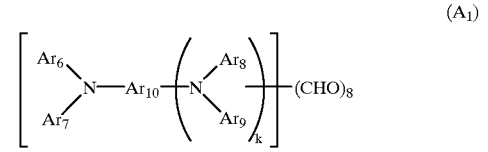
($A_1$)

($B_1$)

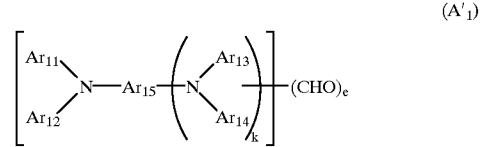
($A'_1$)

($B'_1$)

In general formulas $A_1$ and $A'_1$, e is an integer of 1–4.

The details of Method A, which utilizes the compounds represented by general formulas A and B, are given in detail below.

The basic substance to be used in the synthesis can be any substance selected from the group consisting of sodium hydroxide, sodium carbonate, sodium methoxide, sodium ethoxide, pyridine, triethyl amine, n-butyl lithium, phenyl lithium, sodium hydride and the like. Among these substances, sodium hydroxide is particularly preferable from the viewpoint of the stability of the silane compound of the present invention to the base. Although the amount of the basic substance to be used in the synthesis may be selected depending on the kinds of the phosphonium salt and the rate of the reaction, the use of a large amount of the basic substance makes the treatment or separation thereof difficult. Therefore the amount of the basic substance is in the range of 1 to 10 mol, preferably 1 to 1.5 mol, per 1 mol of the phosphonium salt.

In the synthesis reaction, a solvent can be used. The solvent may be any solvent selected from the group consisting of ethanol, chloroform, dichloromethane, nitromethane, dimethyl sulfoxide, diethyl ether, N,N-dimethyl formamide, tetrahydrofuran, pentane, benzene, xylene and the like. A mixture of these solvents may also be used. These solvents are preferably dehydrated prior to use. Among these solvents, non-aqueous, polar solvents, such as N,N-dimethyl formamide and dimethyl sulfoxide, are particularly preferable in view of such advantages as a high stereoselectivity and ease in separation after completion of the reaction.

The reaction temperature is preferably from −30 to 80° C., more preferably −30 to 25° C., and most preferably −10 to 5° C.

Example of the precursor for producing the phosphorus compound to be used in the above-described synthesis include triphenylphosphine, triethoxyphosphine, chlorodiphenylphosphine and chlorodiethoxyphosphine.

These precursors can be synthesized by use of Hal—$CH_2$—$Y^1$—$SiR_{1(3-a)}(OR_2)_a$ according to a Wittig's method described, for example, in "Comprehensive Experiments in Organic Reactions", S. Huenig et al., translated by Y. Nomura et al., pp. 532, Morikita Publishing Co., Ltd. and in "Experimental Chemistry 19" (Organic Synthesis I), pp. 57, Maruzen Publishing Co., Ltd.

Examples of the reaction for reducing the silane compound, which is represented by general formula I and in which one to four of $Ar_1$–$Ar_5$ have a substituent represented by —CH=CH—$Y^1$—$SiR_{1(3-a)}(OR_2)_a$, to the silane compound, which is represented by general formula I and in which one to four of $Ar_1$–$Ar_5$ have a substituent represented by —$CH_2CH_2$—$Y^3$—$SiR_{1(3-a)}(OR_2)_a$, include a catalytic reduction utilizing a solid hydrogenation catalyst, such as a Raney nickel catalyst, a reduced nickel catalyst, a nickel-kieselguhl catalyst, $PtO_2$ (Adams catalyst), platinum black, supported platinum (e.g., Pt/C, Pt/$Al_2O_3$), supported palladium (e.g., Pd/C, Pd/$BaSO_4$, and Pd/$CaCO_3$), palladium black or PdO, and a reduction utilizing a hydrogenating agent such as triethylsilane, trimethylsilane or the like. A catalytic reduction utilizing a solid hydrogenation catalyst, such as a Raney nickel catalyst, a supported Pt or a supported Pd catalyst, is preferable in view of ease in reaction and low costs.

Among the silane compounds represented by general formula I, a silane compound, which contains a smaller amount of a silicon-containing substituent, is chemically more stable, and therefore is more advantageous in production.

The details of Method B, which utilizes the compounds represented by general formulas A' and B', are given in detail below.

The acidic catalyst to be used in the synthesis can be any substance selected from the group consisting of hydrochloric acid, sulfuric acid, acetic acid, formic acid, trifluoroacetic acid, p-toluenesulfonic acid and the like. Among these substances, p-toluenesulfonic acid is particularly preferable from the viewpoint of the stability of the silane compound of the present invention to the acid. Although the amount of the acidic catalyst to be used in the synthesis may be selected depending on such a factor as the rate of the reaction, the use of a large amount of the basic substance makes the treatment or separation thereof difficult or diminishes the selectivity of the reaction. Therefore the amount of the acidic catalyst is from 0.01 to 10 mol, preferably 0.01 to 0.1 mol, per 1 mol of the compound having a formyl group or an amino group.

In the synthesis reaction, a solvent can be used. The solvent may be selected from common organic solvents, that is, from the group consisting of ethanol, chloroform, dichloromethane, nitromethane, dimethyl sulfoxide, diethyl ether, N,N-dimethyl formamide, tetrahydrofuran, pentane, hexane, benzene, xylene and the like. A mixture of these solvents may also be used. Among these solvents, toluene is particularly preferable.

The reaction temperature is preferably from 0 to 100° C.

The compounds represented by general formula I, can be used in such fields of application as a coating material for electrophotographic photoreceptors, organic EL elements, solar cells, organic electroconductors, carriers for use in electrostatic photography and the like, surface treatment of charge-generation materials and intermediate layer between a material, such as aluminum, nickel or Nesa glass, and an organic photosensitive layer. For example, the compound of the present invention can be used in the charge-transport layer of an electrophotographic photoreceptor comprising an electroconductive substrate, such as aluminum, and a charge-generation layer and a charge-transport layer formed on the substrate. Further, the compound of the present invention can be used in the surface protective layer in an electrophotographic photoreceptor comprising an electroconductive substrate, such as aluminum, and a charge-generation layer, a charge-transport layer and a surface protective layer formed on the substrate. More concretely, a charge-transport layer or a surface protective layer can be formed by the application of a coating solution containing the compound of the present invention. After the application, the produced layer may be converted into a hardened film by means of heating or by use of a catalyst such as phosphoric acid, sulfuric acid, ammonia gas, acetic acid, hydrochloric acid, a titanate catalyst, or an aluminum-based catalyst.

For example, the silane compound of the present invention can be applied to an electrophotographic photoreceptor comprising an electroconductive substrate, a charge-generation layer and a charge-transport layer formed on the substrate or to an electrophotographic photoreceptor comprising an electroconductive substrate, a charge-generation layer, a charge-transport layer and a surface protective layer as an outermost layer formed on the substrate. More concretely, an electrophotographic photoreceptor may contain the silane compound represented by aforesaid general formula I as a charge-transport material in a surface protective layer Further, as a preferred example, an electrophotographic photoreceptor contains the silane compound represented by aforesaid general formula I as a charge-transport material in at least one layer selected from a charge-transport layer and a surface protective layer and contains crystals of a phthalocyanine compound as a charge-generation material in the charge-generation layer. As a more preferred example, an electrophotographic photoreceptor contains a known charge-transport material, such as a hydrazone compound, a stilbene compound or the like, in a charge-transport layer and contains crystals of a phthalocyanine compound as a charge-generation material in a charge-generation layer and contains the silane compound represented by aforesaid general formula I in a surface protective layer.

As for the fluorine-containing polymer to be used in the present invention, various materials may be used which include a fluorine-containing polymer, a fluorine-containing silane compound, a fluorine-containing ether and a fluorine-containing ester. A fluorine-containing ester, in particular, is preferable, because this material enhances the lubrication on the surface and the storage stability of the coating solution. Materials, such as a fluorine-containing amine and a fluorine-containing carboxylic acid, are preferable, because these materials act as a catalyst in the case where a chemical bond is formed between the silane compounds represented by aforesaid general formula I or between a silane compound represented by aforesaid general formula I and other silane compound. Materials, such as a fluorine-containing alcohol and a fluorine-containing olefin, are more preferable, because these materials can form a chemical bond with a silane compound represented by aforesaid general formula I.

A fluorine-containing silane coupling agent is the most preferable, because this material can form a more solid chemical bond with a silane compound represented by aforesaid general formula I.

Concrete examples of these fluorine-containing compounds are given below.

Examples of the fluorine-containing polymer include PTFE (tetrafluoroethylene polymer), FEP (tetrafluoroethylene/hexafluoroethylene/copolymer), PCTFE (trifluorochloroethylene polymer), PVF (vinyl fluoride polymer), PFA (tetrafluoroethylene/perfluoroalkyl vinylether/copolymer), PVdF (vinylidene fluoride polymer), ETFE (tetrafluoroethylene/ethylene copolymer), and ECTFE (ethylene/trifluorochloroethylene copolymer).

Examples of the fluorine-containing silane compounds include bis(pentafluorophenyl)dimethylsilane, bis(tridecafluoro-1,1,2,2-tetrahydrooctyl)tetramethyldisiloxane, 1,3-bis(3,3,3-trifluoropropyl)tetramethyldisiloxane, dimethyldifluorosilane, diphenyldifluorosilane, methyltrifluorosilane, and N-methyl-N-trimethylsilyltrifluoroacetoamide.

Examples of the fluorine-containing ether include 2,2,2-trifluoroethylmethyl ether, 2,2,2-trifluoroethyldifluoromethyl ether, 1,1,2,2-tetrafluoroethylmethyl ether, 2,2,3,3,3-pentafluoropropylmethyl ether, 2,2,3,3,3-pentafluoropropyldifluoromethyl ether, 1,1,2,2-tetrafluoroethyl ether, 1,1,2,2-tetrafluoroethyl-2,2,2-trifluoroethyl ether, 2,2,3,3,-tetrafluoropropyldifluoromethyl ether, hexafluoroisopropylmethyl ether, hexafluoroisopropyldifluoromethyl ether, 1,1,2,3,3,3-hexafluoropropylmethyl ether, 2,2,3,3,3-pentafluoropropyl-1,1,2,2-tetrafluoroethyl ether, 1,1,3,3,3-pentafluoro-2-trifluoromethylpropylmethyl ether, 1,1,2,3,3,3-hexafluoroisopropylethyl ether, and 2,2,3,4,4-hexafluorobutyldifluoromethyl ether.

Examples of the fluorine-containing ester include methyl perfluoropropionate, ethyl perfluoropropionate, methyl perfluorobutylate, ethyl 5-hydroxyoctafluoroheptanoate, ethyl perfluorooctanoate, methyl perfluorooctanoate, and ethyl perfluorooctanoate.

Examples of the fluorine-containing amine include 1,1,-dihydro-heptafluorobutylamine and 1,1,-dihydro-pentadecafluorobutylamine.

Examples of the fluorine-containing carboxylic acid include trifluoroacetic acid, perfluoropanoic acid, perfluorobutanoic acid, perfluoropentanoic acid, perfluorohexanoic acid, perfluoroheptanoic acid, perfluorooctanoic acid, perfluorononanoic acid, perfluorodecanoic acid, and perfluoroundecanoic acid.

Examples of the fluorine-containing alcohol include 2,2,2-trifluoroethanol, 2-fluoroethanol, 2,2,3,3,3-pentafluoropropanol, 1,1,3-trihydrotetrafluoropentanol, 2-hydro-hexafluoro-2-propanol, 1,1,3-trihydrohexafluorobutanol, 1,1,5-trihydrotetrafluoropentanol, 2,2-bis(trifluoromethyl)propanol, 2-(perfluorobutyl)ethanol, 2-perfluoropropoxy-2,3,3,3-tetrafluoropropanol, 3-perfluorobutyl-2-iodopropanol, 2-(perfluoro-3-methylbutyl)ethanol, 1,1,7-trihydrododecafluoroheptanol, 6-(perfluoroethyl)hexanol, 1,1-dihydroheptafluorobutanol, 2-(perfluorohexyl)ethanol, 3-(perfluohexyl)propanol, 3-perfluorohexyl-2-iodopropanol, 6-(perfluoro-1-methylethyl)hexanol, 2-(perfluoro-5-methylhexyl)ethanol, 1,1,9-trihydrohexadecafluorononanol, 6-(perfluorobutyl)hexanol, 2-(perfluorooctyl)ethanol, 3-(perfluoro-5-methylhexyl-2-iodopropanol, 3-(perfluorooctyl)propanol, 3-perfluorooctyl- 2-iodopropanol, 6-(perfluoro-3-methylbutyl)hexanol, 2-(perfluoro-7-methyloctyl)ethanol, 6-(perfluorohexyl)hexanol, 2-(perfluodecyl)ethanol, 3-(perfluoro-7-methyloctyl)-2-iodopropanol, 6-(perfluoro-5-methylhexyl)hexanol, 2-(perfluoro-9-methyldecyl)ethanol, 6-(perfluooctyl)hexanol, and 6-(perfluoro-7-methyldecyl)ethanol.

Examples of the fluorine-containing olefin include 1-methoxy-(perfluoro-2-methyl-1-propane), perfluorobutylethylene, perfluorohexylethylene, 1,4-divinyloctafluorobutane, perfluooctylethylene, 1,6-divinyldodecaefluorohexane, perfluorodecylethylene, and 1,8-divinylhexadecaefluorooctane.

Examples of the fluorine-containing silane coupling agent include 3,3,4,4,5,5,6,6,6-nonafluorohexylmethyldichlorosilane, 3,3,4,4,5,5,6,6,6-nonafluorohexyltrichlorosilane, pentafluoropropyltrichlorosilane, pentafluoropropyltrimethoxysilane, (tridecafluoro-1,1,2,2-tetrahydrooctyl)dimethylchlorosilane, (tridecafluoro-1,1,2,2-tetrahydrooctyl)methyldichlorosilane, (tridecafluoro-1,1,2,2-tetrahydrooctyl)trichlorosilane, (tridecafluoro-1,1,2,2-tetrahydrooctyl)trimethoxylsilane, (tridecafluoro-1,1,2,2-tetrahydrooctyl)triethoxylsilane, (3,3,3-trifluoropropyl)dimethylchlorosilane, (3,3,3-trifluoropropyl)methyldichlorosilane, (3,3,3-trifluoropropyl)trichlorosilane, (3,3,3-trifluoropropyl)trimethoxysilane, (heptadecafluoro-1,1,2,2-tetrahydrodecyl)dimethylchlorosilane, (heptadecafluoro-1,1,2,2-tetrahydrodecyl)trichlorosilane, (peptadecafluoro-1,1,2,2-tetrahydrodecyl)triethoxysilane, (heptadecafluoro-1,1,2,2-tetrahydrodecyl)trimethoxylsilane, (3-heptafluoroisopropoxy)propyltrichlorosilane, (3-heptafluoroisopropoxy)propyltriethoxylsilane, triethoxyfluorosilane, and 3-trifluoroacetoxypropyltrimethoxysilane.

It is possible to produce an electrophotographic photoreceptor, which has a tough surface layer of a low surface energy and which has a superior durability, by use of the silane compound represented by aforesaid general formula I and the fluorine-containing compound of the present invention. As for a charge-generation material and a charge-transport material, any of materials known as such can be employed. As a preferred example because of superiority in sensitivity and stability, an electrophotographic photoreceptor contains crystals of a phthalocyanine compound as a charge-generation material and also contains the compound represented by aforesaid general formula I singly or in combination with a known charge-transport material, such as a hydrazone compound, a stilbene compound or the like, together with the fluorine-containing compound in the photosensitive layer. As another example, an electrophotographic photoreceptor has a charge-generation layer comprising crystals of a phthalocyanine compound as a charge-generation material, a charge-transport layer comprising a known charge-transport material, such as a hydrazone compound, a stilbene compound or the like, together with a known binder, such as polycarbonate or polyester, and a protective layer comprising the compound represented by general formula I together with a fluorine-containing compound on the charge-transport layer.

As for the phthalocyanine crystals to be used in combination with the compound represented by aforesaid general formula I and a fluorine-containing compound, examples of the suitable phthalocyanine crystals include the halogenated gallium phthalocyanine crystals disclosed in JP-A No. 5-98,181, the halogenated tin phthalocyanine crystals disclosed in JP-A Nos. 5-140,472 and 5-140,473, the hydroxy gallium phthalocyanine crystals disclosed in JP-A Nos. 5-263,007 and 5-279,591 and the crystals of hydrated oxytitanium phthalocyanine disclosed in JP-A Nos. 4-189,873 and 5-43,813. The use of such phthalocyanine crystals leads to electrophotographic photoreceptor having a particularly high sensitivity and superiority in stability over repeated use.

Electrophotographic Photoreceptor:

Details of the electrophotographic photoreceptor of the present invention are given below.

The electrophotographic photoreceptor may have a single-layer structure or it may have a laminated structure comprising a charge-generation layer and a charge-transport layer or it may have a surface protective layer as an outermost layer. Although the compound represented by aforesaid general formula I and the fluorine-containing compound may be incorporated in any of the layers, the case where the these compounds are present in the outermost layer is the most effective.

Examples of the electroconductive substrate, on which the charge-generation layer, the charge-transport layer and the like are formed, include a metal, such as aluminum, nickel, chromium or stainless steel, a plastic film coated with a thin layer of a material, such as aluminum, titanium, nickel, chromium, stainless steel, gold, vanadium, tin oxide, indium oxide or ITO, and a paper or plastic film coated with or impregnated with an electroconductivity imparting agent. The electroconductive substrate may be used in an appropriate shape such as a drum, a sheet, a plate or the like, but is not limited to such shapes. In addition, if necessary, the surface of the electroconductive substrate may receive a variety of treatments, in so far as these treatments do not impair the quality of image. For example, the treatments include the oxidizing treatment, chemical treatment, coloring treatment and irregular reflection creating treatment by means of the sanding of the surface. An underlayer may be formed between the electroconductive substrate and the charge-generation layer. At the time when the photosensitive layer of the laminated structure is electrostatically charged, the underlayer prevents the injection of charge into the photosensitive from the electroconductive substrate. Further, the underlayer functions as a bonding layer to bond the photosensitive layer and the electroconductive substrate into one piece and sometimes functions as a barrier to prevent reflection of light on the electroconductive substrate.

Examples of the binder polymers to be used for the underlayer include known materials such as polyethylene resins, polypropylene resins, acrylic resins, methacrylic resins, polyamide resins, vinyl chloride resins, vinyl acetate resins, phenol resins, polycarbonate resins, polyurethane resins, polyimide resins, vinylidene chloride resins, polyvinylacetal resins, vinylchloride/vinylacetate copolymers, polyvinyl alcohol resins, water-soluble polyester resins, nitrocellulose, casein, gelatin, polyglutamic acid, starch, starch acetate, amino starch, polyacrylic acid, polyacryl amide, zirconium chelate compounds, titanium chelate compounds, titanium alkoxide compounds, organotitanium compounds and the silane coupling agents. An appropriate thickness for the underlayer is in the range of 0.01–10 $\mu$m, preferably 0.05–2 $\mu$m. The coating methods for producing the underlayer include conventional methods such as blade coating, wire bar coating, spraying, immersion coating, bead coating, air knife coating and curtain coating.

In the case of a laminated structure, a charge-generation layer and a charge-transport layer are formed on the underlayer.

The explanation starts with the charge-generation layer. A charge-generation material is dispersed in a suitable binder polymer (binder resin) to produce a charge-generation layer. As for the charge-generation material to be incorporated in the charge-generation layer, any known charge-generation materials, which include phthalocyanine crystals, bisazo pigments, phthalocyanine pigments, squalene pigments, perylene pigments and dibromoanthoanthrone, can be used. Among these materials, phthalocyanine crystals are most preferable.

Examples of the phthalocyanine crystals suitable as the charge-generation material include the halogenated gallium phthalocyanine crystals disclosed in JP-A No. 5-98,181, the halogenated tin phthalocyanine crystals disclosed in JP-A Nos. 5-140,472 and 5-140,473, the hydroxy gallium phthalocyanine crystals disclosed in JP-A Nos. 5-263,007 and 5-279,591 and the crystals of hydrated oxytitanium phthalocyanine disclosed in JP-A Nos. 4-189,873 and 5-43,813. The use of suchphthalocyanine crystals leads to an electrophotographic photoreceptor having a particularly high sensitivity and superior stability over repeated use.

An example of the halogenated phthalocyanine crystals to be used in the present invention is chlorogallium phthalocyanine crystals. The chlorogallium phthalocyanine crystals for use in the present invention can be produced by pulverizing the chlorogallium phthalocyanine crystals, which may be obtained by any known process, by means of a dry grinding method comprising mechanically treating the crystals in a machine such as automatic mortar, a planetary mill, a vibration mill, a CF mill, a roller mill, a sand mill or a kneader or by further wet-grinding the dry-ground crystals by means of a solvent in such a machine as a ball mill, a mortar, a sand mill or a kneader, as disclosed in JP-A No. 5-98,181. Examples of the solvent to be used in the above-mentioned wet grinding method include aromatic hydrocarbons, such as toluene and chlorobenzene, amides, such as dimethylformamide and N-methylpyrrolidone, aliphatic alcohols, such as methanol, ethanol and butanol, aliphatic polyhydric alcohols, such as ethylene glycol, glycerin and polyethylene glycol, aromatic alcohols, such as benzyl alcohol and phenetyl alcohol, esters, such as ethyl acetate and butyl acetate, ketones, such as acetone and methyl ethyl ketone, ethers, such as dimethyl sulfoxide, diethyl ether and tetrahydrofuran, mixtures of the foregoing, and a mixture of any of these organic solvents and water. The amount of the solvent to be used is 1–200 parts by weight, preferably 10–100 parts by weight, per one part by weight of chlorogallium phthalocyanine crystals. The treating temperature is in the range of 0° C. to the boiling point of the solvent to be used, preferably 10 to 60° C. Further, a grinding aid, such as sodium chloride or Glauber's salt, can be used in the pulverizing process. The amount of the grinding aid may be 0.5–20 parts by weight, preferably 1–10 parts by weight, per one part by weight of chlorogallium phthalocyanine crystals.

Examples of the halogenated tin phthalocyanine crystals to be used in the present invention include dichlorotin phthalocyanine crystals. The dichlorotin phthalocyanine crystals for use in the present invention can be produced by pulverizing the dichlorotin phthalocyanine crystals, which have been obtained by any known process as disclosed in JP-A Nos. 5-140,472 and 5-140,473, to be followed by the treatment with a solvent as in the case of chlorogallium phthalocyanine crystals described above.

The hydroxygallium phthalocyanine crystals for use in the present invention can be produced by a process comprising hydrolyzing or acid-pasting the chlorogallium phthalocyanine crystals, which have been obtained by any known process as disclosed in JP-A Nos. 5-263,007 and 5-279,591, in an acidic or alkaline solution to obtain hydroxygallium phthalocyanine crystals and treating the obtained hydroxygallium phthalocyanine crystals immediately with a solvent or otherwise wet-grinding the obtained hydroxygallium phthalocyanine crystals by means of a solvent in such a machine as a ball mill, a mortar, a sand mill or a kneader or dry-grinding the obtained hydroxygallium phthalocyanine crystals by a dry-grinding means without utilizing any solvent and thereafter wet-treating the hydroxygallium phthalocyanine crystals with a solvent. The solvent to be used in the above-mentioned wet grinding may be the same as the solvent in the case of the wet-grinding of the chlorogallium phthalocyanine crystals stated previously. The amount of the solvent to be used is 1–200 parts by weight, preferably 10–100 parts by weight, per one part by weight of hydroxygallium phthalocyanine crystals. The treating temperature is in the range of from 0 to 150° C., preferably from room temperature to 100° C. Further, a grinding aid, such as sodium chloride or Glauber's salt, can be used in the pulverizing process. The amount of the grinding aid may be 0.5–20 parts by weight, preferably 1–10 parts by weight, per one part by weight of hydroxygallium phthalocyanine crystals.

The oxytitanium phthalocyanine crystals for use in the present invention can be produced by acid-pasting or salt-milling, together with an inorganic salt by means of such a machine as a ball mill, a mortar, a sand mill or a kneader, the oxytitanium phthalocyanine crystals, which may be obtained by any known process as disclosed in JP-A Nos. 4-189,873 and 5-43,813, to obtain oxytitanium phthalocyanine crystals having a relatively low crystallinity that exhibits a peak at 27.2° in X-ray diffraction spectrum and treating the obtained oxytitanium phthalocyanine crystals immediately with a solvent or otherwise wet-grinding the obtained oxytitanium phthalocyanine crystals by means of a solvent in such machine as a ball mill, a mortar, a sand mill or a kneader. For the acid-pasting step, the acid is preferably sulfuric acid; the concentration of the acid is 70 to 100%, preferably 95 to 100%; the dissolution temperature is −20 to 100° C., preferably 0 to 60° C.; and the amount of the concentrated sulfuric acid is 1–100 parts by weight, preferably 3–100 parts by weight, per one part by weight of oxytitanium phthalocyanine crystals. As a solvent to be used at the acid-pasting step, water or a mixture of water and an organic solvent may be used in any amount. A mixture of water and an alcohol, such as methanol or ethanol, or a mixture of water and an aromatic solvent, such as benzene or toluene, is particularly preferable. Although the deposition temperature is not particularly limited, it is preferable that the temperature is lowered by means of ice in order to remove the heat of exotherm. The ratio of oxytitanium phthalocyanine crystals to inorganic salt (by weight) is in the range of 1/0.1 to 1/20, preferably 1/0.5 to 1/5. Examples of the solvent to be used in the above-mentioned treatment with a solvent include aromatic hydrocarbons, such as toluene and chlorobenzene, aliphatic alcohols, such as methanol, ethanol and butanol, halogenated hydrocarbons, such as dichloromethane, chloroform and trichloroethane, a mixture of the foregoing, and a mixture of any of these organic solvents and water. The amount of the solvent to be used is 1–100 parts by weight, preferably 5–50 parts by weight, per one part by weight of oxytitanium phthalocyanine crystals. The treating temperature is from room temperature to 100° C., preferably 50 to 100° C. Further, a grinding aid, such as sodium chloride or Glauber's salt, can be used in the pulverizing process. The amount of the grinding aid may be 0.5–20 parts by weight, preferably 1–10 parts by weight, per one part by weight of oxytitanium phthalocyanine crystals.

The binder polymer to be used in the charge-generation layer can be selected from a wide variety of insulating resins. Also, it can be selected from organic photoconductive polymers such as poly-N-vinylcarbazole, polyvinylanthracene, polyvinylpyrene and polysilane. Preferred non-limiting examples of the binder polymer are insulating resins including polyvinylbutyral resins, polyarylate resins (e.g., a polycondensation product from bisphenol A and phthalic acid), polycarbonate resins, polyester resins, phenoxy resins, vinylchloride/vinylacetate copolymers, polyamide resins, acrylic resins, polyacrylamide resins, polyvinylpyridine resins, cellulose resins, urethane resins, epoxy resins, casein, polyvinyl alcohol resins and polyvinyl pyrrolidone resins. These binder polymers may be used alone or in a combination of two or more of them.

The blending ratio of the charge-generation material to the binder polymer is preferably from 10:1 to 1:10 by weight. The charge-generation material can be dispersed into the binder polymer by conventional means such as a ball mill, an attritor or a sand mill.

It is advantageous to reduce the particle size to about 0.5 μm or less, preferably 0.3 μm or less, and most preferably 0.15 μm or less, by the dispersing operation. Examples of solvents to be used in the dispersing operation include conventional organic solvents such as methanol, ethanol, n-propanol, n-butanol, benzylalcohol, methylcellosolve, ethylcellosolve, acetone, methyl ethyl ketone, cyclohexanone, methyl acetate, n-butyl acetate, dioxane, tetrahydrofuran, methylene chloride, chloroform, chlorobenzene and toluene. These solvents may used alone or in a combination of two or more of them.

The charge-generation layer may be formed on the charge-transport layer, or it may be formed between the underlayer and the charge-transport layer.

As for the charge-transport material, the silane compound represented by general formula I may be used alone or in combination thereof with a fluorine-containing compound. The combination of the silane compound and the fluorine-containing compound may be further combined with a material compatible therewith. Therefore, silane compound and the fluorine-containing compound may be dispersed in a known polymer. Furthermore, the resulting blend may be hardened. It is also possible to produce a blend from the silane compound represented by general formula I (optionally in combination with a fluorine-containing compound), a hydrazone-based charge-transport material, a triarylamine-based charge-transport material, a stilbene-based charge-transport material and a charge-transport polymer. Furthermore, the resulting blend may be hardened.

The above-mentioned hydrazone-based charge-transport material, triarylamine-base charge-transport material, stilbene-based charge-transport material or charge-transport polymer may be used singly or in a combination thereof in place of the compound represented by general formula I, if a surface protective layer containing the compound represented by general formula I is formed on the charge-transport layer as described later.

Examples of the binder polymer to be used in the charge-transport layer may be a known resin and include insulating resins, such as a polycarbonate resin, a polyester resin, a methacrylic resin, an acrylic resin, a polyvinyl chloride resin, a polyvinylidene chloride resin, a polystyrene resin, a polyvinyl acetate resin, a styrene/butadiene copolymer, a vinylidene chloride/acrylonitrile copolymer, a vinylchloride/vinylacetate copolymer, a vinylchloride/vinylacetate/maleic anhydride copolymer, a silicone resin, a silicone/alkyd resin, a commercialized hard coat material, a phenol/formaldehyde resin and a styrene/alkyd resin, electroconductive resins, such as a poly-N-vinylcarbazole resin and a polysilane resin, polycondensation products of coupling agents, such as an aluminum-based coupling agent, a silane-based coupling agent and a titanium-based coupling agent, and charge-transport polymers, such as polyester and polycarbonate, disclosed in JP-A Nos. 64-13,061, 64-19,049, 8-196,293, 8-208,820 and 8-211,640. However, the binder polymer to be used in the charge-transport layer is not limited to these polymers. Among these polymers, the polycarbonate resins represented by general formulas II–VI below or the polycarbonate resins obtained by the copolymerization thereof are preferable from such viewpoints as compatibility and film formability.

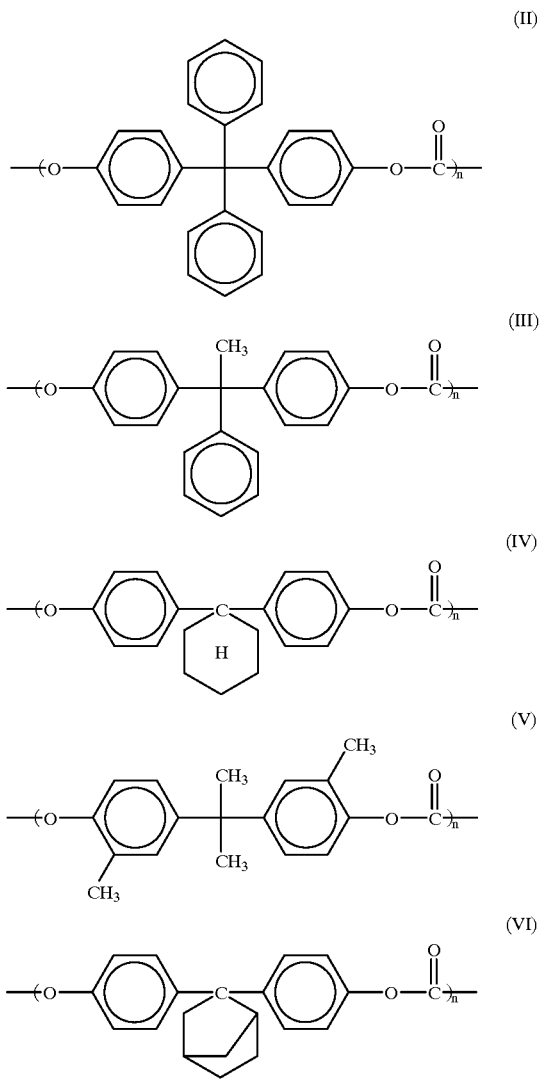

In the above structural formulas, n stands for the degree of polymerization, which is an integer of 50 to 3,000.

These binder polymers may be used alone or in a combination of two or more. The blending ratio of the silane compound as a charge-generation material to the binder polymer is preferably from 10:1 to 1:5 by weight.

A commercialized hardcoat material or a silane coupling agent can form a chemical bond indicated by —O—Si—O— with the compound represented by general formula I and therefore provides a tough film.

If the silane compound represented by general formula I is used in combination with other charge-transport material, the weight ratio of the silane compound to the other charge-transport material is in the range of 100/1 to 1/100, preferably 90/10 to 10/90, and more preferably 60/40 to 40/60. If the silane compound and the other charge-transport material are further blended with a binder polymer, the weight ratio of the sum of the silane compound and the other charge-transport material to the binder polymer is in the range of 100/1 to 1/100, preferably 80/20 to 50/50.

Besides these charge-transport materials and the binder polymer, an additive, which is compatible with the silane compound and the fluorine-containing compound, may be added.

The curing reaction to obtain a hard film may be effected in the absence of a catalyst or in the presence of a suitable catalyst. Examples of the catalyst, which can be used in the hardening reaction, include acid catalysts, such as hydrochloric acid, sulfuric acid, formic acid, acetic acid and trifluoroacetic acid, bases such as ammonia and triethylamine, organotin compounds, such as tibutyltin diacetate, dibutyltin dioctoate and tinI octoate, organotitanium compounds, such as tetra-n-butyl titanate and tetra-isopropyl titanate, organic carboxylic acid salts of metals such as iron, manganese, cobalt, zinc and zirconium.

In a reaction to harden the substances used in the present invention, having a carbon/carbon double bond in the skeleton of the compound, a known hydrosilylation catalyst, such as $H_2PtCl_6 \cdot 6H_2O$, $RhCl(PPh_3)_3$, $IrCl(CO)(PPh_3)_3$, $Co_2(CO)_8$, $Pt(C_2H_4)(PPh_3)_2$ or $[Pt(C_2H_4)Cl_2]_2$, may be used singly or in combination with any of the above-mentioned catalysts. Although the temperature and the humidity at the time of the hardening reaction are not particularly specified, the temperature and the humidity are preferably from room temperature to 150° C. and 40 to 100%, respectively.

Examples of the coating method for forming the charge-transport layer are commonly used methods such as blade coating, wire bar coating, spraying, immersion coating, bead coating, air knife coating and curtain coating.

The thickness of the charge-transport layer is in the range of 5 to 50 μm, preferably 10 to 30 μm.

If a protective layer is formed on the charge-transport layer, the protective layer may be formed by hardening the silane compound represented by general formula I and the fluorine-containing compound which is used if desired. In this case, the weight ratio of a charge-transport material to a binder is in the range of 10/90 to 70/30, preferably 20/80 to 60/40 in the charge-transport layer. If necessary, the protective layer may be incorporated with a coupling agent, such as an aluminum-based coupling agent, a silane-based coupling agent or a titanate-based coupling agent, fine particles such as colloidal silica, a conventional binder resin, such as the resin employed in the charge-transport layer or charge-generation layer, or a commercialized hardcoat material. If the combination of the compound represented by general formula I and the fluorine-containing compound, which is optionally used, is further blended with other material, the weight ratio of the foregoing combination to the other material is in the range of 100/1 to 1/100, preferably 90/10 to 10/90, and more preferably 70/30 to 20/80.

Examples of the coupling agents, which can be used in the surface protective layer and the charge-transport layer, include aluminum-based coupling agents, such as acetoxyaluminum diisopropylate, acetoethoxyaluminum diisopropylate and acetopropoxyaluminum diisopropylate, titanate-based coupling agents, such as titanium n-butoxide and titanium ethoxide, and silane-based coupling agents, such as vinyltrichlorosilane, vinyltrimethoxysilane, vinyltriethoxysilane, γ-glycidoxypropylmethyldiethoxysilane, γ-glycidoxypropyltrimethoxysilane, γ-glycidoxypropyltriethoxysilane, γ-aminopropyltriethoxysilane, γ-aminopropyltrimethoxysilane, γ-aminopropylmethyldimethoxysilane, N-β(aminoethyl)-γ-aminopropyltriethoxysilane, tetramethoxysilane, methyltrimethoxysilane and dimethyldimethoxysilane. Examples of the commercialized hardcoat material include KP-85 (manufactured by Shin-Etsu Silicone Co., Ltd.), CR-39 (manufactured by Shin-Etsu Silicone Co., Ltd.), X-12-2208 (manufactured by Shin-Etsu Silicone Co., Ltd.), X-40-9740 (manufactured by Shin-Etsu Silicone Co., Ltd.), X-41-1007 (manufactured by Shin-Etsu Silicone Co., Ltd.), KNS-5300 (manufactured by Shin-Etsu Silicone Co., Ltd.), X-40-2239 (manufactured by Shin-Etsu Silicone Co., Ltd.), AY42-440 (manufactured by Toray Dow Corning Silicone Co., Ltd.), AY42-441 (manufactured by Toray Dow Corning Silicone Co., Ltd.), and AY49-208 (Toray Dow Corning Silicone Co., Ltd.).

A preferred solvent to be used in forming the protective layer is the solvent which dissolves the materials for forming the protective layer but does not attack the underlying charge-transport layer. Examples of the solvent include alcohols, such as ethanol, butanol and cyclohexanol, ethers, such as diethyl ether and dibutyl ethers, aromatic solvents, such as xylene and p-cymene, and cellosolves such as methylcellosolve and ethylcellosolve. Among these solvents, dibutyl ether is particularly preferable, because the use of dibutyl ether leads to the formation of a tough film.

The reaction to harden the protective layer can be effected in the same way as in the case of the charge-transport layer.

The thickness of the protective layer is in the range of 0.1–10 μm, preferably 0.5–7 μm, and more preferably 1–5 μm. The coating methods for producing the protective layer include conventional methods such as blade coating, Meyer bar coating, spraying, immersion coating, bead coating, air knife coating and curtain coating.

In the case where the electrophotographic photoreceptor has a single-layer structure, the compound represented by general formula I, the fluorine-containing compound and the charge-generation material are blended toghether according to a desired proportion. If necessary, the blend may be further added with other known material such as a charge-transport material, a binder, a coupling agent, an antioxidant or a hardening catalyst. Preferably, such an adding material is capable of chemically bonding with the compound represented by general formula I and with the fluorine-containing compound. In this case, the material, which can form a chemical bond indicated by —O—Si—O— after the addition, is particularly preferable, because a tough film can be obtained.

The weight ratio of the compound represented by general formula I to the fluorine-containing compound is in the range of 99:1 to 40:60, preferably 95:5 to 50:50, and more preferably 90:10 to 40:60. If other material is to be blended in, the weight ratio of the sum of the compound represented by general formula I, the fluorine-containing compound and the charge-generation material to the other material is in the range of 99:1 to 40:60, preferably 95:5 to 45:55, and more preferably 90:10 to 50:50.

The thickness of the layer is from 5 to 50 μm, preferably 10 to 40 μm. The coating methods for producing the single-layer electrophotographic photoreceptor include conventional methods such as blade coating, Meyer bar coating, spraying, immersion coating, bead coating, air knife coating and curtain coating. Examples of the solvent to be used in the coating include tetrahydrofuran, chlorobenzene, toluene, methylene chloride, chloroform and cyclohexanone. These solvents may be used alone or in a combination of two or more of them.

Further, the above-described layer can be hardened by such means as heat or moisture. In this case, the preferred examples of the fluorine-containing compound include a fluorine-containing silane compound, a fluorine-containing alcohol and a fluorine-containing olefin. The fluorine-containing silane compound is particularly preferable. A particularly preferred binder is a substance which can react to produce a chemical bond indicated by —O—Si—O—.

EXAMPLES

The details of the present invention are explained below by way of examples.

Synthesis 1

Synthesis of Silane Compound 1

A two-neck flask purged with nitrogen was charged with 25 g of 3-iodopropyltrimethoxysilane and 200 mL of toluene, and a solution was produced. Then, 27 g of triphenylphosphine was added to the solution. The reaction mixture was stirred and heated at reflux for 7 hours. The deposited crystals were washed well with toluene, and thereafter the solvent was removed at reduced pressure to obtain 36.5 g of phosphonium salt as white crystals. The melting point of the obtained phosphonium salt was 102.0 to 102.5° C. The IR absorption spectrum of this phosphonium salt is shown in FIG. 1.

Figure 2:
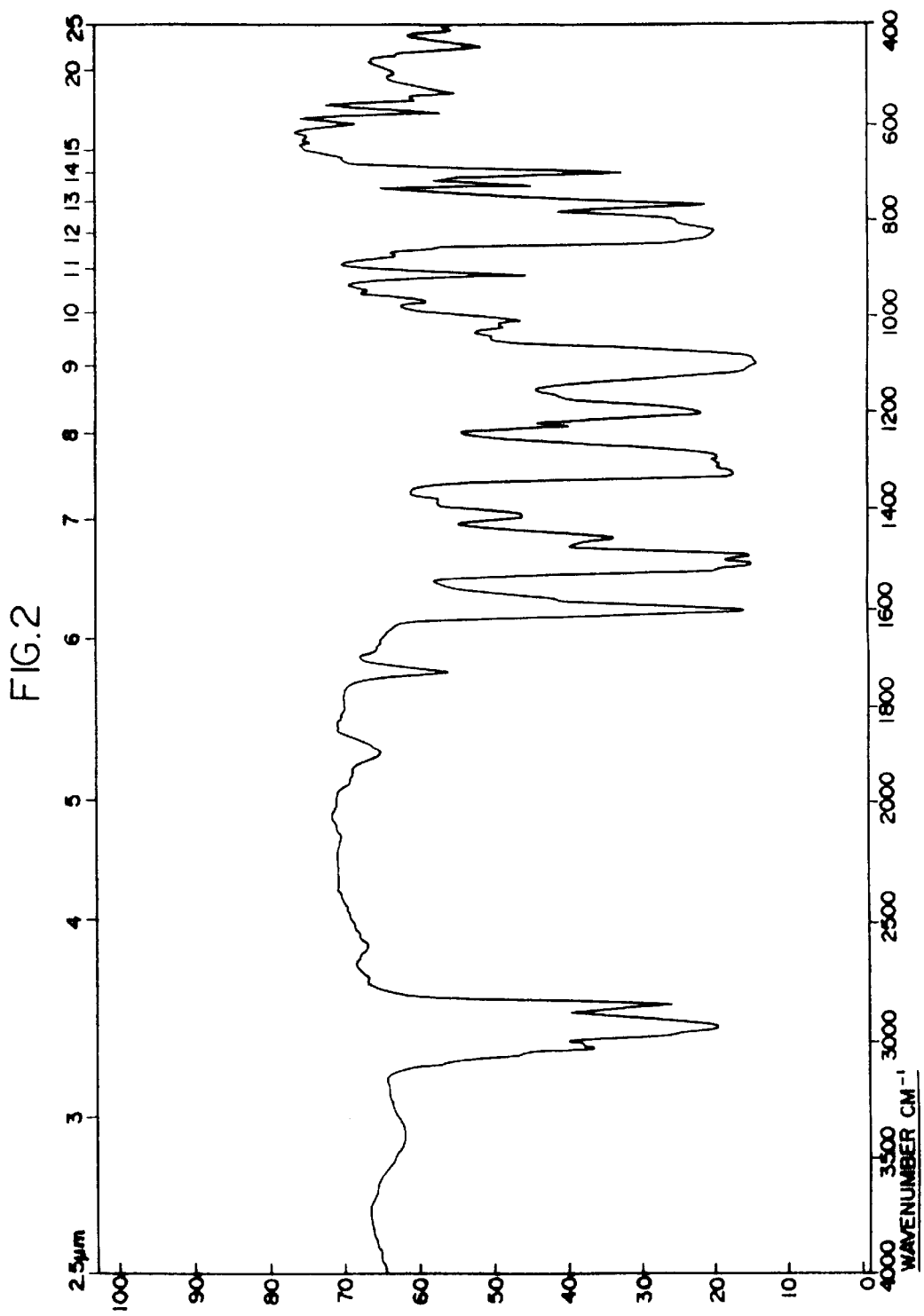
FIG. 2 shows the IR absorption spectrum of the silane compound prepared in Synthesis 1.

A two-neck flask purged with nitrogen was charged with 15 g of the phosphonium salt and 300 mL of anhydrous dimethylformamide, and a solution was produced. The solution was cooled down to −5° C. and 1.05 g of sodium hydride was added to the solution, which was stirred for 15 minutes. Then, while the solution was being stirred, 5.1 g of N-(4-formyl)-N-(3,4-dimethylphenyl)biphenyl-4-amine was added to the solution, which was gradually heated up to room temperature and stirred for 2 hours. After completion of the reaction, 10 mL of methanol was added to the reaction mixture, and the reaction mixture was mixed with 3 L of ice water. Then, the mixture was extracted with toluene. After removal of the solvent from the solution at reduced pressure, the residue was purified by means of silica gel in a column (eluent: toluene) to give 6 g of silane compound 1 as a pale yellow oily product. The IR absorption spectrum of the obtained silane compound 1 is shown in FIG. 2.

Synthesis 2

Synthesis of Silane Compound 21

Figure 3:
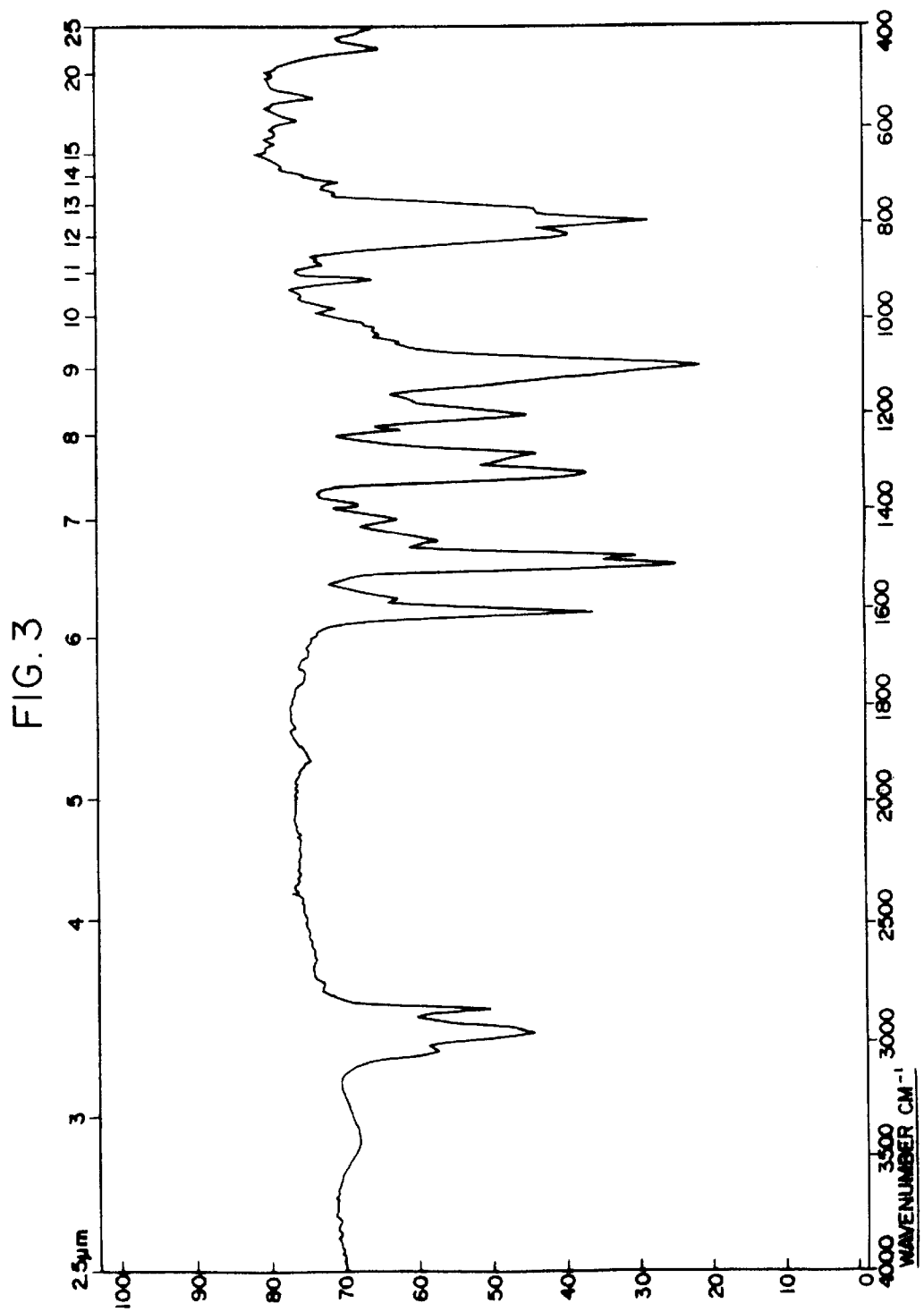
FIG. 3 shows the IR absorption spectrum of the silane compound prepared in Synthesis 2.

A two-neck flask purged with nitrogen was charged with 15.9 g of the phosphonium salt prepared in Synthesis 1 and 300 mL of anhydrous dimethylformamide, and thus a solution was produced. The solution was cooled down to −5° C. and 1.5 g of sodium hydride was added to the solution, which was stirred for 15 minutes. Then, while the solution was stirred, 6.0 g of 3,3'-dimethyl-N,N'-bis(4-formylphenyl)-N,N'-bis(3,4-dimethylphenyl)-1,1'-biphenyl-4,4'-diamine was added to the solution, which was gradually heated up to room temperature and was stirred for 2 hours. After completion of the reaction, 30 mL of methanol was added to the reaction mixture, and thereafter the reaction mixture was poured into 3 L of ice water. Then, the mixture was extracted with toluene. After removal of the solvent from the solution at reduced pressure, the residue was purified by means of silica gel in a column (eluent: toluene) to give 6.9 g of silane compound 21 as a pale yellow oily product. The IR absorption spectrum of the obtained silance compound 21 is shown in FIG. 3.

Examples 1 and 2

Utilizing the silane compounds prepared in Synthesis 1 and in Synthesis 2, respectively, photoreceptors for use in electrostatic photography were prepared in the following way.

Formation of an underlayer:

To a 30-mm-diameter drum-shaped aluminum substrate, which had undergone a honing treatment, there was applied a solution, comprising 10 parts by weight of a zirconium compound (Orgatics ZC540, manufactured by Matsumoto Pharmaceuticals Manufacturing Co., Ltd.), 1 part by weight of a silane compound (A1110, manufactured by Nippon Yuncar Co., Ltd.), 40 parts by weight of isopropanol and 20 parts by weight of butanol, by means of immersion coating, and then the film was dried for 10 minutes at 150° C. to form an underlayer having a thickness of 0.5 µm.

Formation of a charge-generation layer:

A mixture, which comprised 1 part by weight of x-type, metal-free phthalocyanine, 1 part of a polyvinyl butyral resin (Eslec BM-S, manufactured by Sekisui Chemical Co., Ltd.) and 100 parts by weight of n-butyl acetate, was treated together with glass beads to prepare a dispersion by means of a paint shaker for 1 hour. The coating liquid thus obtained was applied onto the above-described underlayer by means of immersion coating, and then the film was dried for 10 minutes at 100° C. to form a charge-generation layer.

Formation of a charge-transport layer:

Next, 32 parts by weight of N-(4-methylphenyl)-N-(3,4-dimethylphenyl)biphenyl-4-amine and 3 parts by weight of the polycarbonate resin represented by structural formula (IV) were dissolved in 20 parts by weight of monochlorobenzene. The coating liquid thus obtained was applied onto the above-described charge-generation layer by means of immersion coating, and then the film was dried for 1 hour at 120° C. to form a charge-transport layer having a thickness of 20 µm.

Formation of a surface protective layer:

Further, 3 parts by weight of the silane compound prepared in Synthesis 1, 1 part by weight of phenyltriethoxysilane and 6 parts by weight of a silicone hardcoat material (X-40-2239, manufactured by Shin-Etsu Silicone Co., Ltd.) were dissolved in 5 parts by weight of ethyl acetate. The coating liquid thus obtained was applied onto the above-described charge-transport layer by means of immersion coating, and then the film was dried at room temperature to form a surface protective layer having a thickness of 3 µm.

The above-described procedure was repeated except that the silane compound prepared in Synthesis 2 was used in place of the silane compound prepared in Synthesis 1, and, in this way, another electrophotographic photoreceptor was prepared.

The electrophotographic photoreceptors obtained in the above-described manner were mounted, respectively, on a real copying machine (XP-11, manufactured by Fuji Xerox Co., Ltd.) After a durability test of making 10,000 copies of B4 size PPC recording paper, a distinct image was obtained and the surface of the photoreceptor was free from wear, scratches, peeling, cracks, and the like.

Synthesis 3

Synthesis of Silane Compound 34

Figure 4:
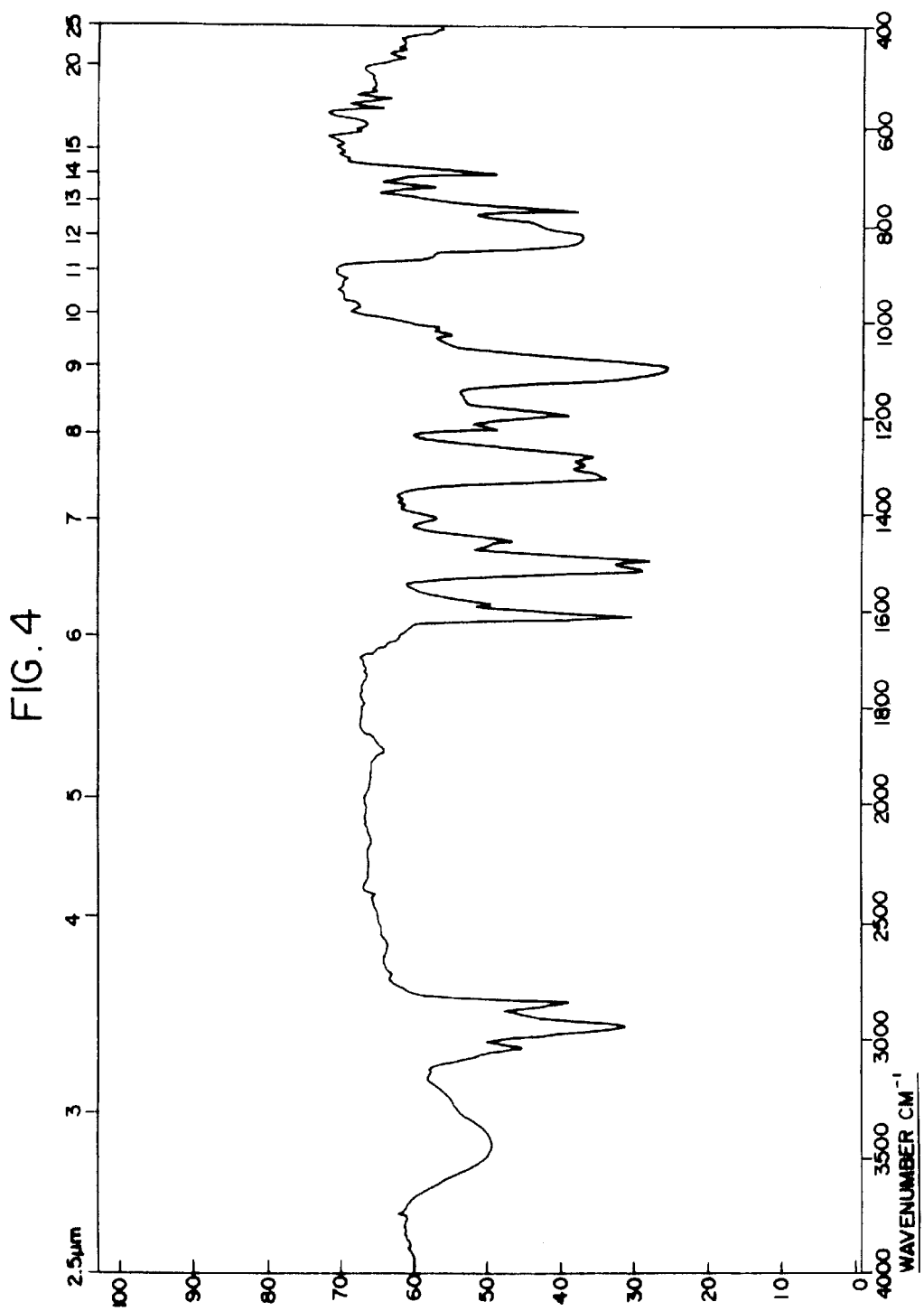
FIG. 4 shows the IR absorption spectrum of the silane compound prepared in Synthesis 3.

A pear-shaped flask was charged with 6 g of silane compound 1 prepared in Synthesis 1, 20 mL of tetrahydrofuran and 20 mL of ethanol, and a solution was produced. Then, 0.1 g of 5% Pd-C was added to the solution, and thereafter the flask atmosphere was replaced with dry hydrogen gas. The reaction mixture was left to react for 15 hours at room temperature, while the gas inlet of the flask was connected to the dry hydrogen gas supply. After completion of the reaction, the Pd-C was filtered off and the solvent was removed from the solution at reduced pressure. The residue was purified by means of silica gel in a column (eluent: toluene) and thereafter purified by means of recrystallization (solvent: toluene/hexane=1/5) to yield 4.2 g of silane compound 34 as a product in the form of colorless transparent crystals. The IR absorption spectrum of the silane compound 34 is shown in FIG. 4. The melting point was 71.5 to 72° C.

Synthesis 4

Synthesis of Silane Compound 51

Figure 5:
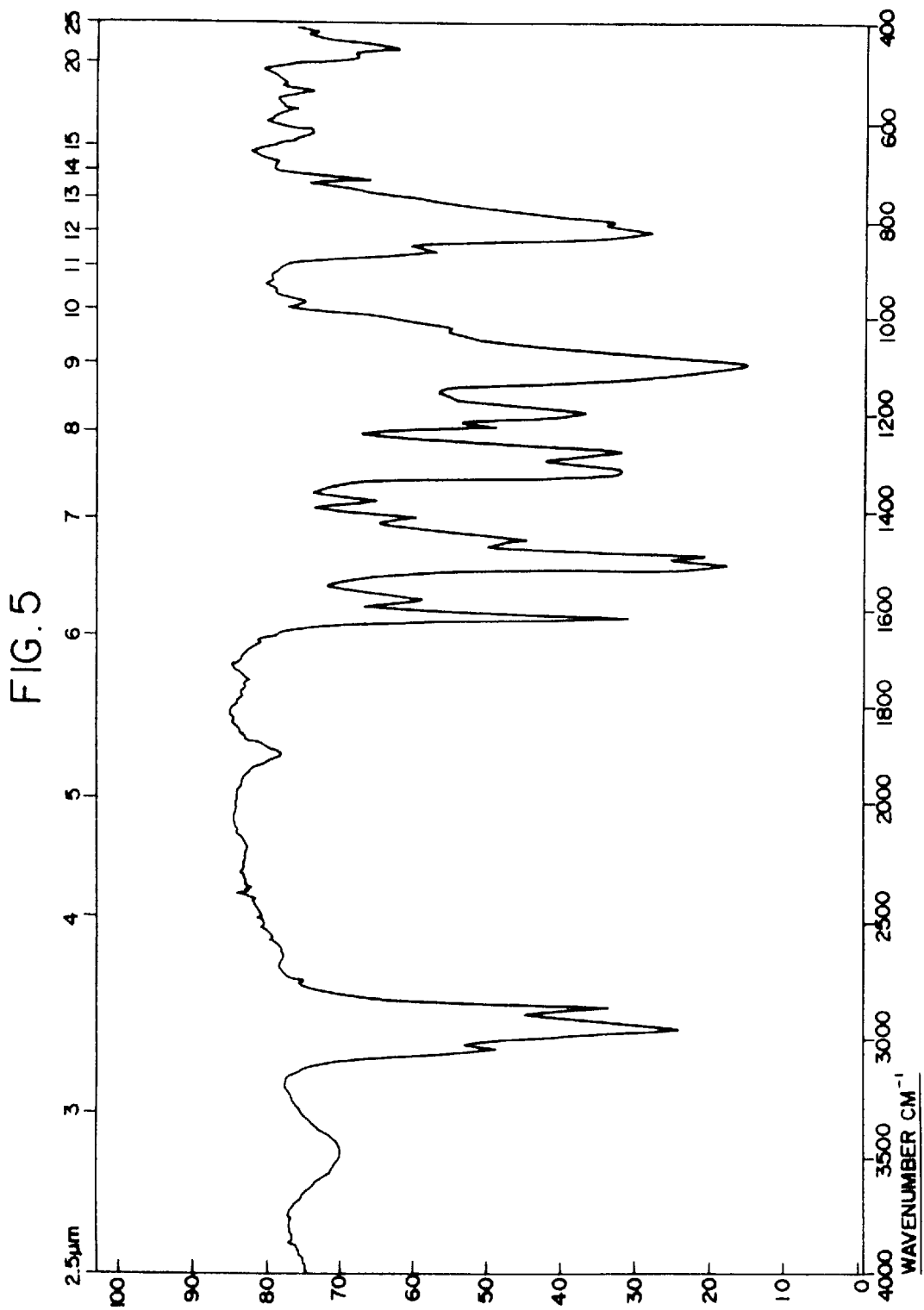
FIG. 5 shows the IR absorption spectrum of the silane compound prepared in Synthesis 4.

A pear-shaped flask was charged with 6.3 g of silane compound 21 prepared in Synthesis 2, 20 mL of tetrahydrofuran and 20 mL of ethanol, and a solution was produced. Then, 0.2 g of 5% Pd-C was added to the solution, and thereafter the flask atmosphere was replaced with dry hydrogen gas. The reaction mixture was left to react for 15 hours at room temperature, while the gas inlet of the flask was connected to the dry hydrogen gas supply. After completion of the reaction, the Pd-C was filtered off and the solvent was removed from the solution at reduced pressure. The residue was purified by means of silica gel in a column (eluent: hexane/ethyl acetate=1/1) to yield 5.9 g of silane compound 51 as a pale yellow oily product with an IR absorption spectrum as shown in FIG. 5.

Example 3

The procedure of Example 1 was repeated to prepare an electrophotographic photoreceptor except that the following surface protective layer was used.
Formation of a surface protective layer:

Six parts by weight of the silane compound prepared in Synthesis 3, and 12 parts by weight of a silicone hardcoat material (X-40-2239, manufactured by Shin-Etsu Silicone Co., Ltd.) were dissolved in 10 parts by weight of cyclohexanone and 2 parts by weight of acetic acid. The coating liquid thus obtained was applied onto the above-described charge-transport layer by means of immersion coating, and then the film was dried at room temperature to obtain a surface protective layer having a thickness of 3 $\mu$m.

The electrophotographic photoreceptor obtained in the above-described manner was mounted on a real copying machine (XP-11, manufactured by Fuji Xerox Co., Ltd.) and given a durability test of making 10,000 copies of B4 size PPC recording paper. The results are shown in Table 6.

Examples 4–18

The procedure of Example 3 was repeated to prepare electrophotographic photoreceptors except that the substances shown in Table 5 were used in place of the silane compound and the silicone hardcoat material (X-40-2239) which were used in Example 3. Utilizing the thus obtained photoreceptors, a durability test was conducted. The results are shown in Table 6. DMS-S15 in Table 5 was obtained from Chisso Corporation.

Comparative Example 1

The procedure of Example 3 was repeated to prepare an electrophotographic photoreceptor except that the surface protective layer was not formed. Utilizing the thus obtained photoreceptor, a durability test was conducted. The results are shown in Table 6.

The results indicate that the silane compounds in Examples have higher solubility and superior film formability and that the film obtained is tough and stable over repeated use.

TABLE 5

| Example | Compound No. | Binder | PhSi(OEt)$_3$ | C$_8$F$_{17}$C$_2$H$_4$Si(OMe)$_3$ |
|---|---|---|---|---|
| 3 | 34 | X-40-2239 (12) | — | — |
| 4 | 34 | X-40-2239 (12) | 2 | — |
| 5 | 34 | X-40-2239 (12) | 1 | 1 |
| 6 | 34 | X-40-2239 (12) | — | 2 |
| 7 | 34 | DMS-S15 (12) | — | — |
| 8 | 34 | DMS-S15 (12) | 2 | — |
| 9 | 34 | DMS-S15 (12) | 1 | 1 |
| 10 | 34 | DMS-S15 (12) | — | 2 |
| 11 | 51 | X-40-2239 (12) | — | — |
| 12 | 51 | X-40-2239 (12) | 2 | — |
| 13 | 51 | X-40-2239 (12) | 1 | 1 |
| 14 | 51 | X-40-2239 (12) | — | 2 |
| 15 | 51 | DMS-S15 (12) | — | — |
| 16 | 51 | DMS-S15 (12) | 2 | — |
| 17 | 51 | DMS-S15 (12) | 1 | 1 |
| 18 | 51 | DMS-S15 (12) | — | 2 |

TABLE 6

| | | State after 10,000 copies | | |
|---|---|---|---|---|
| Example | Pencil hardness | Photoreceptor wear (nm) | Copy image quality | Photoreceptor surface state |
| 3 | 8 H | 148 | Good | Good |
| 4 | 8 H | 116 | Good | Good |
| 5 | 8 H | 96 | Good | Good |
| 6 | 7 H | 151 | Good | Good |
| 7 | 6 H | 195 | Good | Good |
| 8 | 6 H | 179 | Good | Good |
| 9 | 6 H | 171 | Good | Good |
| 10 | 6 H | 206 | Good | Good |
| 11 | 9 H | 55 | Good | Good |
| 12 | 9 H | 27.5 | Good | Good |
| 13 | 9 H | 22 | Good | Good |
| 14 | 8 H | 63 | Good | Good |
| 15 | 8 H | 69 | Good | Good |
| 16 | 8 H | 55 | Good | Good |

TABLE 6-continued

| | | State after 10,000 copies | | |
|---|---|---|---|---|
| Example | Pencil hardness | Photoreceptor wear (nm) | Copy image quality | Photoreceptor surface state |
| 17 | 8 H | 50 | Good | Good |
| 18 | 7 H | 72 | Good | Good |
| CE 1 | 1 H | 880 | Image defect due to photoreceptor scratch | Some scratches |

CE: Comparative Example

Synthesis 5

Synthesis of Silane Compound (7)

Figure 6:
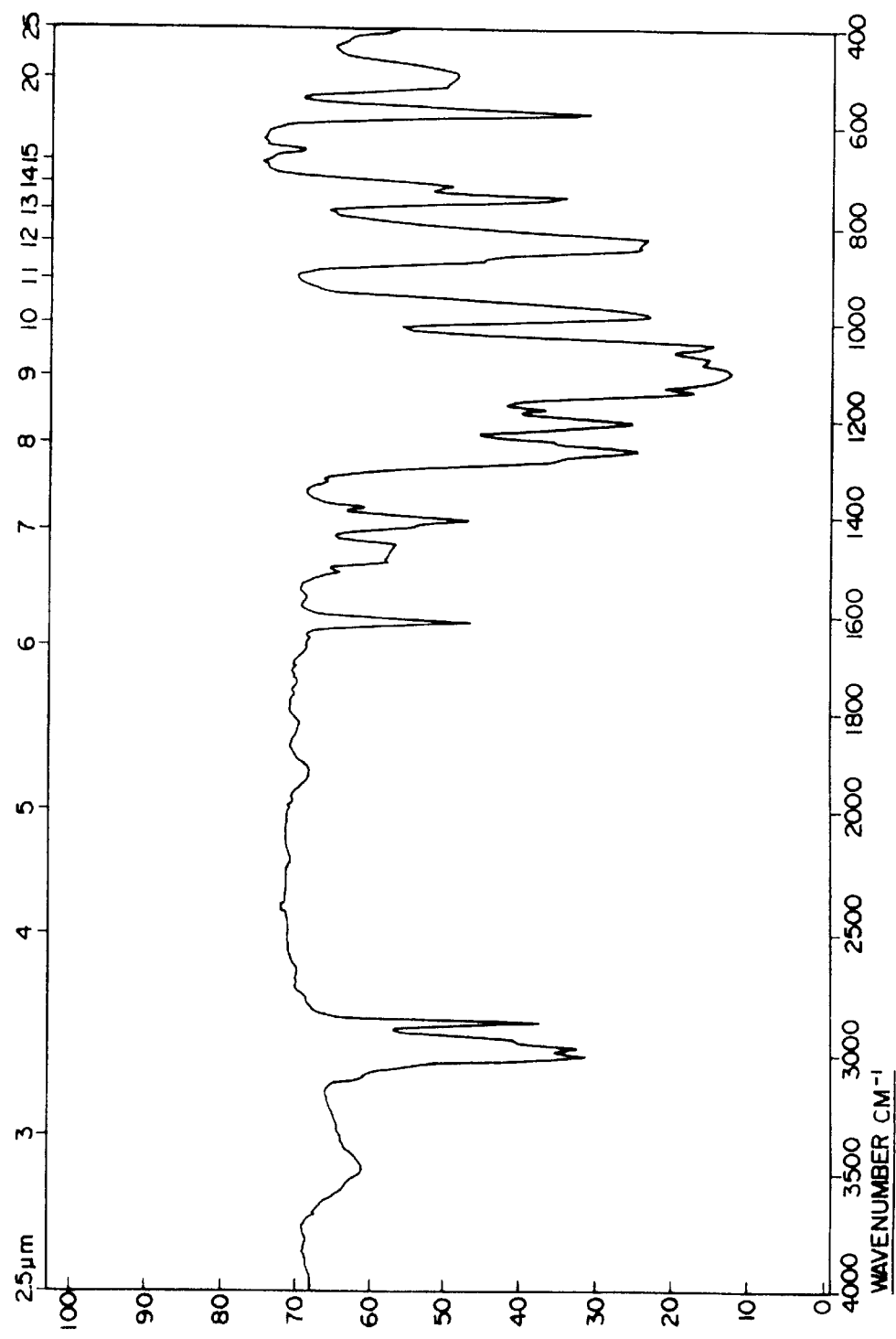
FIG. 6 shows the IR absorption spectrum of the phosphorus compound prepared in Synthesis 5.

A two-neck flask purged with nitrogen was charged with 50 g of triethyl phosphite and 40 g of (chloromethyl)phenyl trimethoxysilane and the mixture was refluxed at 180° C. for 5 hours. Then, the excess triethyl phosphite was removed at high temperature (185° C.) and at low pressure (10 mm Hg). The remaining liquid was filtered to give 50.4 g of a phosphorus compound as a colorless oily product. The IR absorption spectrum of this phosphorus compound is shown in FIG. 6.

Figure 7:
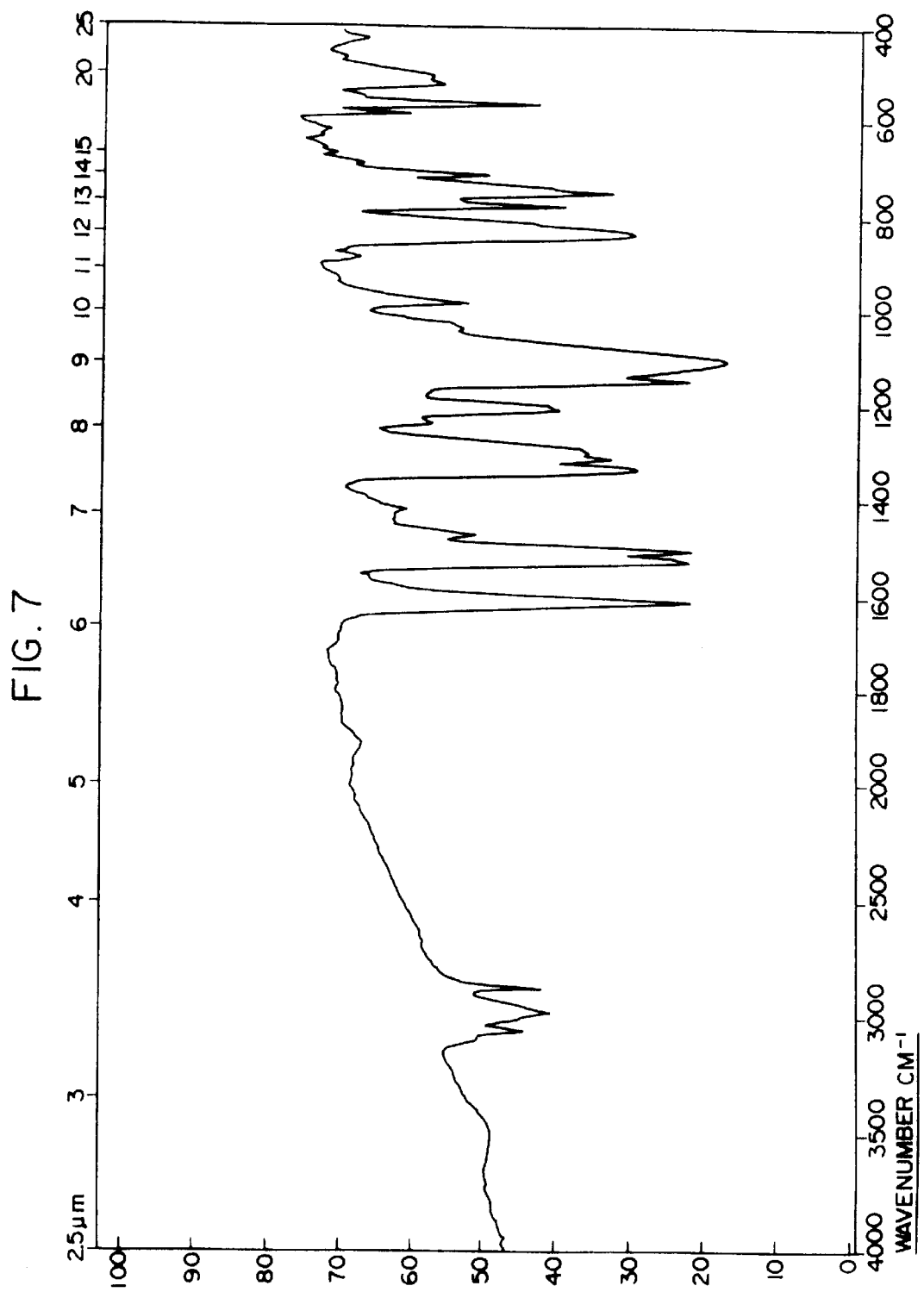
FIG. 7 shows the IR absorption spectrum of the silane compound prepared in Synthesis 5.

A two-neck flask purged with nitrogen was charged with 30 g of the obtained phosphorus compound and 300 mL of anhydrous dimethylformamide, and thus a solution was produced. The solution was cooled down to −5° C. and 3.3 g of sodium hydride was added to the solution, which was stirred for 15 minutes. Then, while the solution was being stirred, 27.9 g of N-(4-formyl)-N-(3,4-dimethylphenyl)biphenyl-4-amine was added to the solution, which was gradually heated up to room temperature and stirred for 2 hours. After completion of the reaction, a product was precipitated twice from the reaction solution by the two-step use of 500 mL of methanol to give 19.8 g of silane compound 7 as a pale yellow oily product. The IR absorption spectrum of the obtained silane compound 7 is shown in FIG. 7.

Synthesis 6

Synthesis of Silane Compound 38

Figure 8:
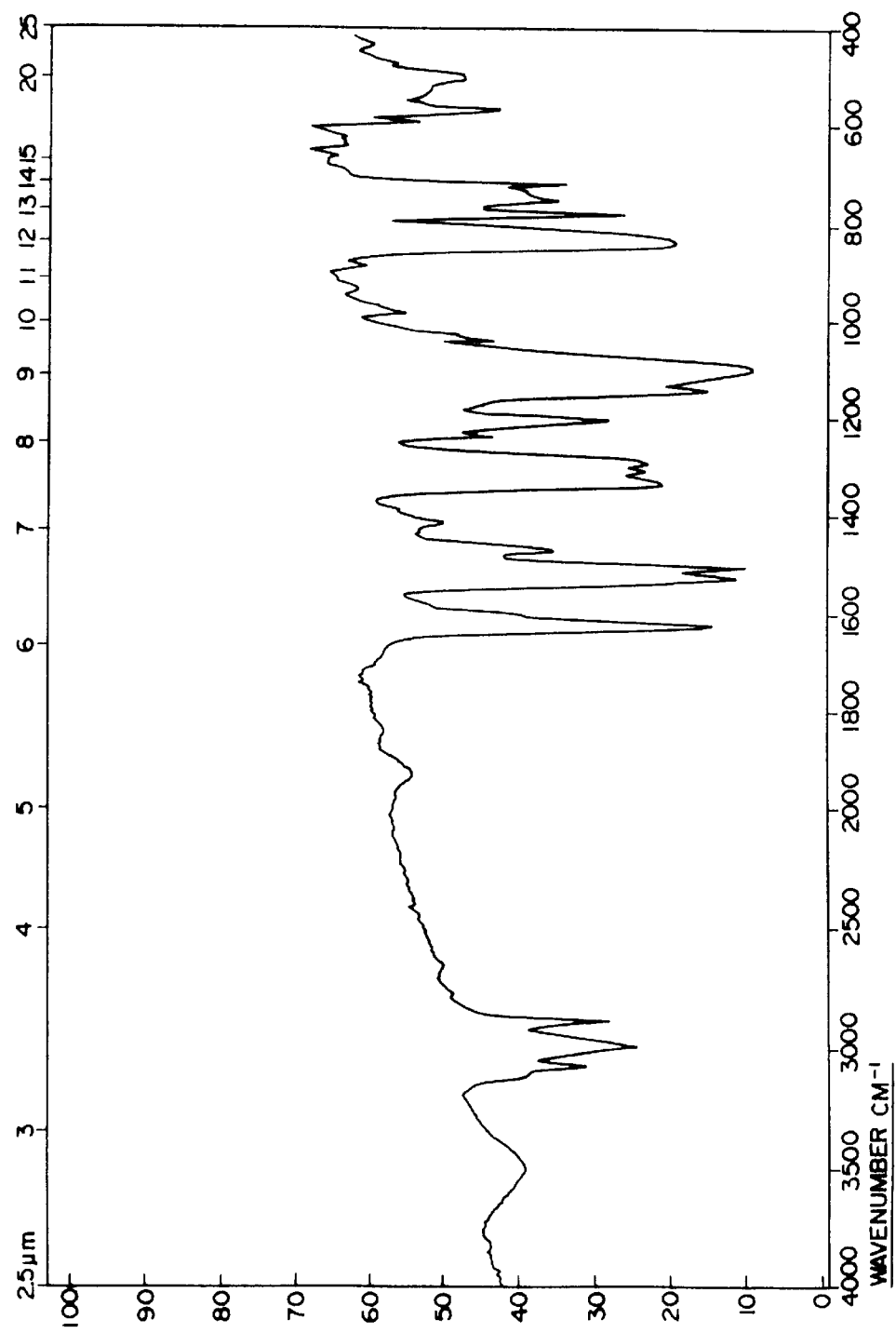
FIG. 8 shows the IR absorption spectrum of the silane compound prepared in Synthesis 6.

A pear-shaped flask was charged with 10 g of the silane compound 7 prepared in Synthesis 5, 100 mL of tetrahydrofuran and 100 mL of ethanol, and thus a solution was produced. Then, 0.5 g of 5% Pd-C was added to the solution, and thereafter the flask atmosphere was replaced with dry hydrogen gas. The reaction mixture was allowed to react for 15 hours at room temperature, while the gas inlet of the flask was connected to the dry hydrogen gas supply. After completion of the reaction, the Pd-C was filtered off and the solvent was removed from the solution at reduced pressure. The residue was purified by means of silica gel in a column (eluent: hexane/ethyl acetate=2/1) to give 9.5 g of silane compound 38 as a pale yellow oily product. The IR absorption spectrum of the obtained silane compound 38 is shown in FIG. 8.

Synthesis 7

Synthesis of Silane Compound 5

Figure 9:
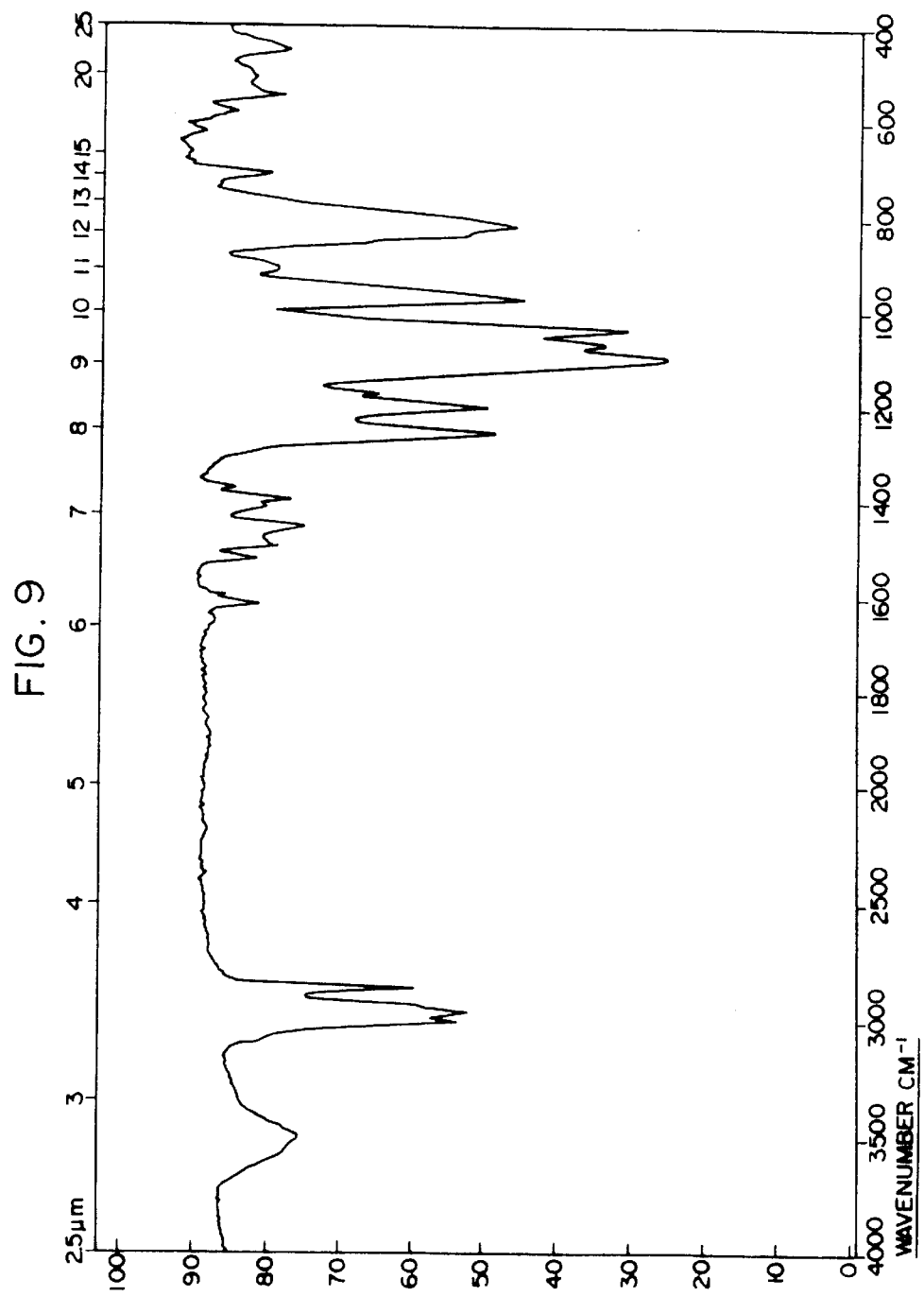
FIG. 9 shows the IR absorption spectrum of the phosphorus compound prepared in Synthesis 7.

A two-neck flask purged with nitrogen was charged with 20 g of triethyl phosphite and 22 g of (chloromethyl) phenylethyltrimethoxysilane and the mixture was refluxed at 180° C. for 6 hours. Then, the excess triethyl phosphite was removed at high temperature (185° C.) and at reduced pressure (10 mm Hg). The remaining liquid was filtered to yield 26.2 g of a phosphorus compound as a pale yellow oily product. The IR absorption spectrum of this phosphorus compound is shown in FIG. 9.

Figure 10:
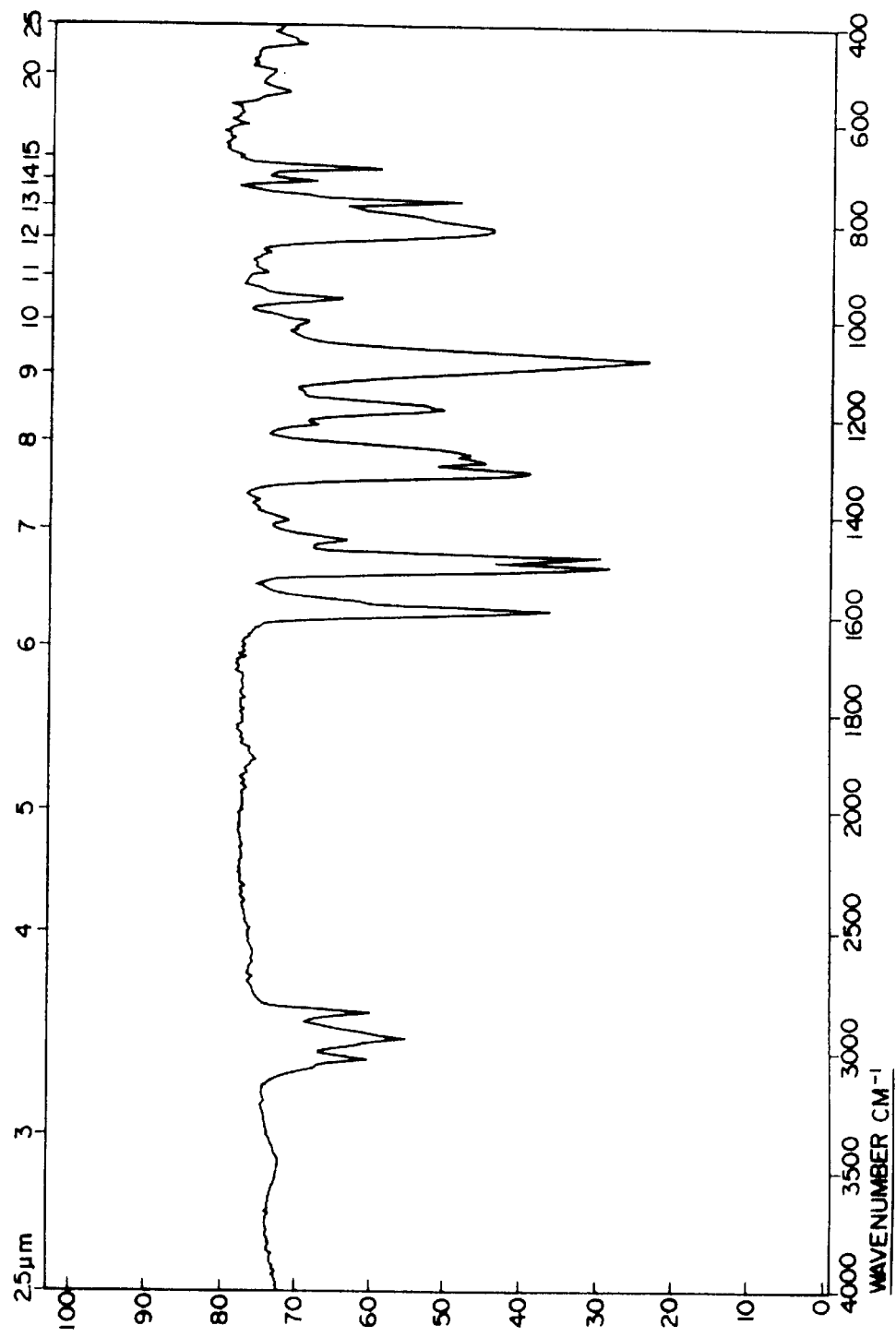
FIG. 10 shows the IR absorption spectrum of the silane compound prepared in Synthesis 7.

A two-neck flask purged with nitrogen was charged with 9.55 g of the phosphorus compound obtained and 300 mL of anhydrous dimethylformamide, and thus a solution was produced. The solution was cooled down to −5° C. and 1 g of sodium hydride was added to the solution, which was stirred for 15 minutes. Then, while the solution was stirred, 8 g of N-(4-formyl)-N-(3,4-dimethylphenyl)biphenyl-4-amine was added to the solution, which was gradually heated to room temperature and was stirred for 2 hours. After completion of the reaction, a product was precipitated twice from the reaction solution by the two-step use of 1,500 mL of methanol to give 9.2 g of silane compound 5 as a yellow solid product. The IR absorption spectrum of the obtained silane compound 5 is shown in FIG. 10.

Synthesis 8

Synthesis of Silane Compound 39

Figure 11:
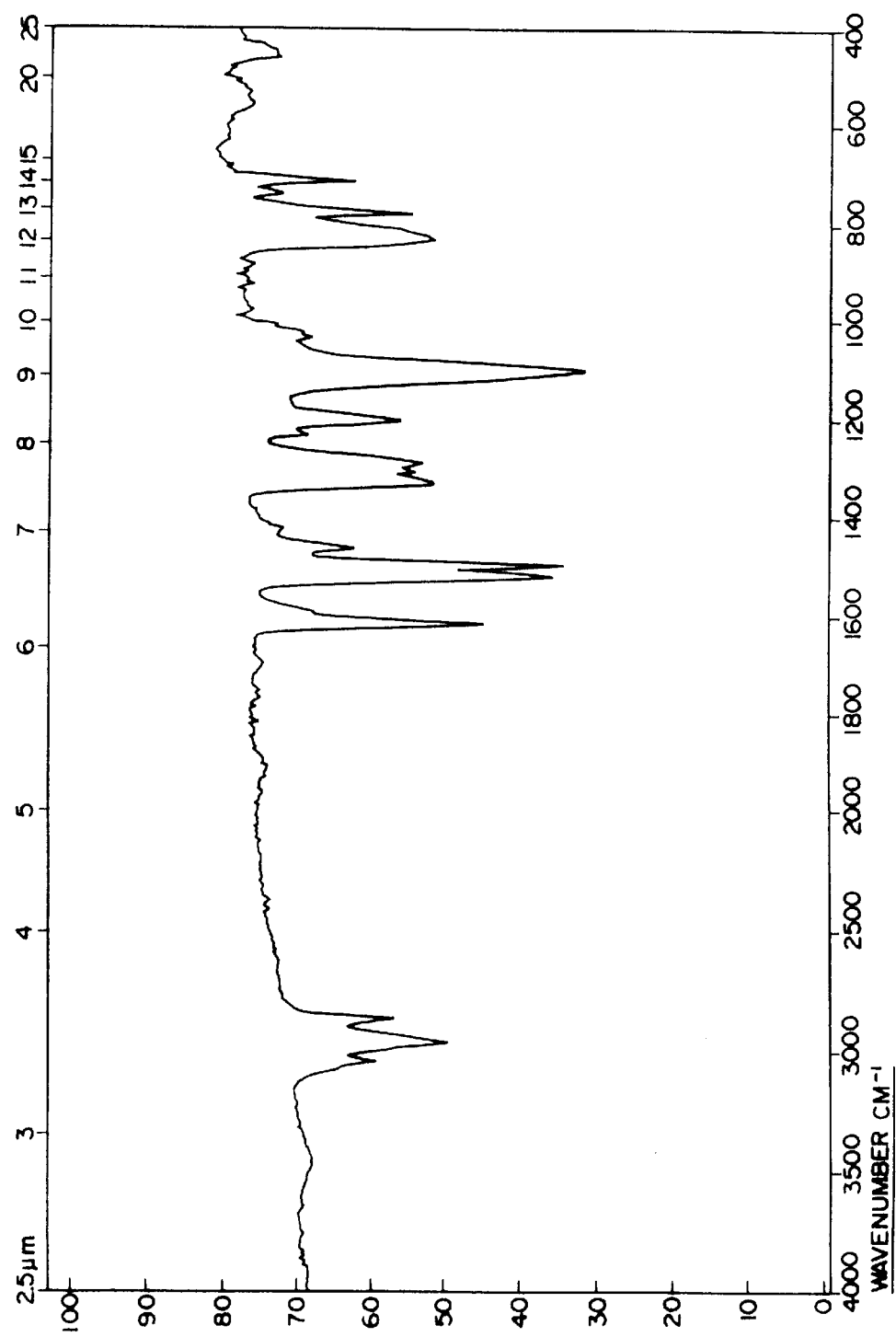
FIG. 11 shows the IR absorption spectrum of the silane compound prepared in Synthesis 8.

A pear-shaped flask was charged with 5 g of the silane compound 5 prepared in Synthesis 7, 100 mL of tetrahydrofuran and 100 mL of ethanol, and thus a solution was produced. Then, 0.2 g of 5% Pd-C was added to the solution, and thereafter the flask atmosphere was replaced with dry hydrogen gas. The reaction mixture was left to react for 15 hours at room temperature, while the gas inlet of the flask was connected to the dry hydrogen gas supply. After completion of the reaction, the Pd-C was filtered off and the solvent was removed from the solution at reduced pressure. The residue was purified by means of silica gel in a column (eluent: hexane/ethyl acetate=2/1) to give 4.5 g of silane compound 39 as a pale yellow oily product. The IR absorption spectrum of the obtained silane compound 39 is shown in FIG. 11.

Synthesis 9

Synthesis of Silane Compound 27

Figure 12:
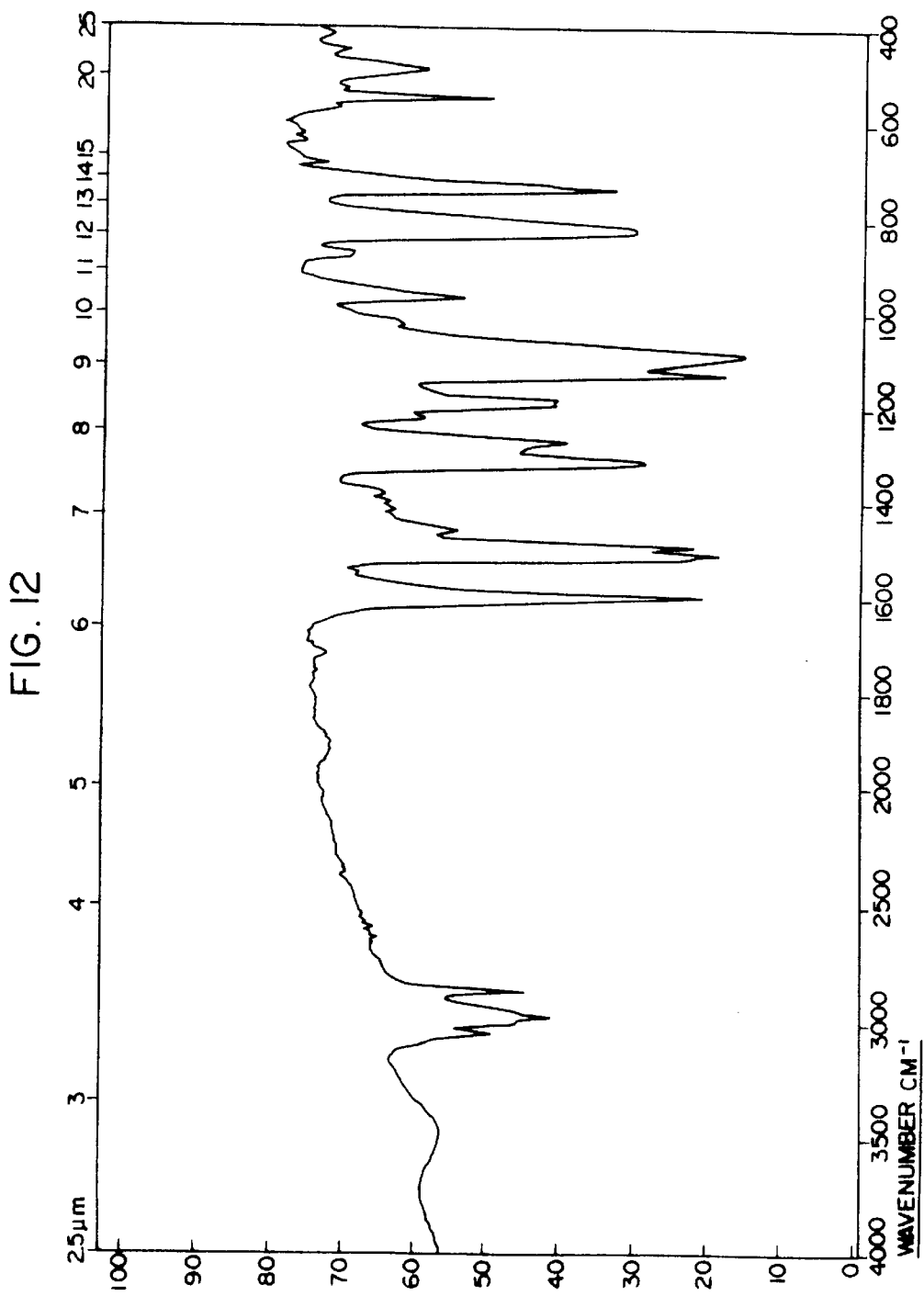
FIG. 12 shows the IR absorption spectrum of the silane compound prepared in Synthesis 9.

A two-neck flask purged with nitrogen was charged with 25 g of the phosphorus compound prepared in Synthesis 5 and 150 mL of anhydrous dimethylformamide, and thus a solution was produced. The solution was cooled down to −5° C. and 2.75 g of sodium hydride was added to the solution, which was stirred for 15 minutes. Then, while the solution was being stirred, 19.6 g of 3,3'-dimethyl-N,N'-(4-formylphenyl)-N,N'-bis(3,4-dimethylphenyl)-1,1'-biphenyl-4,4'-diamine was added to the solution, which was gradually heated up to room temperature and stirred for 2 hours. After completion of the reaction, a product was precipitated twice from the reaction solution by the two-step use of 1 L of methanol to give 21.1 g of silane compound 27 as a yellow solid product. The IR absorption spectrum of the silane compound 27 obtained is shown in FIG. 12.

Synthesis 10

Synthesis of Silane Compound 55

Figure 13:
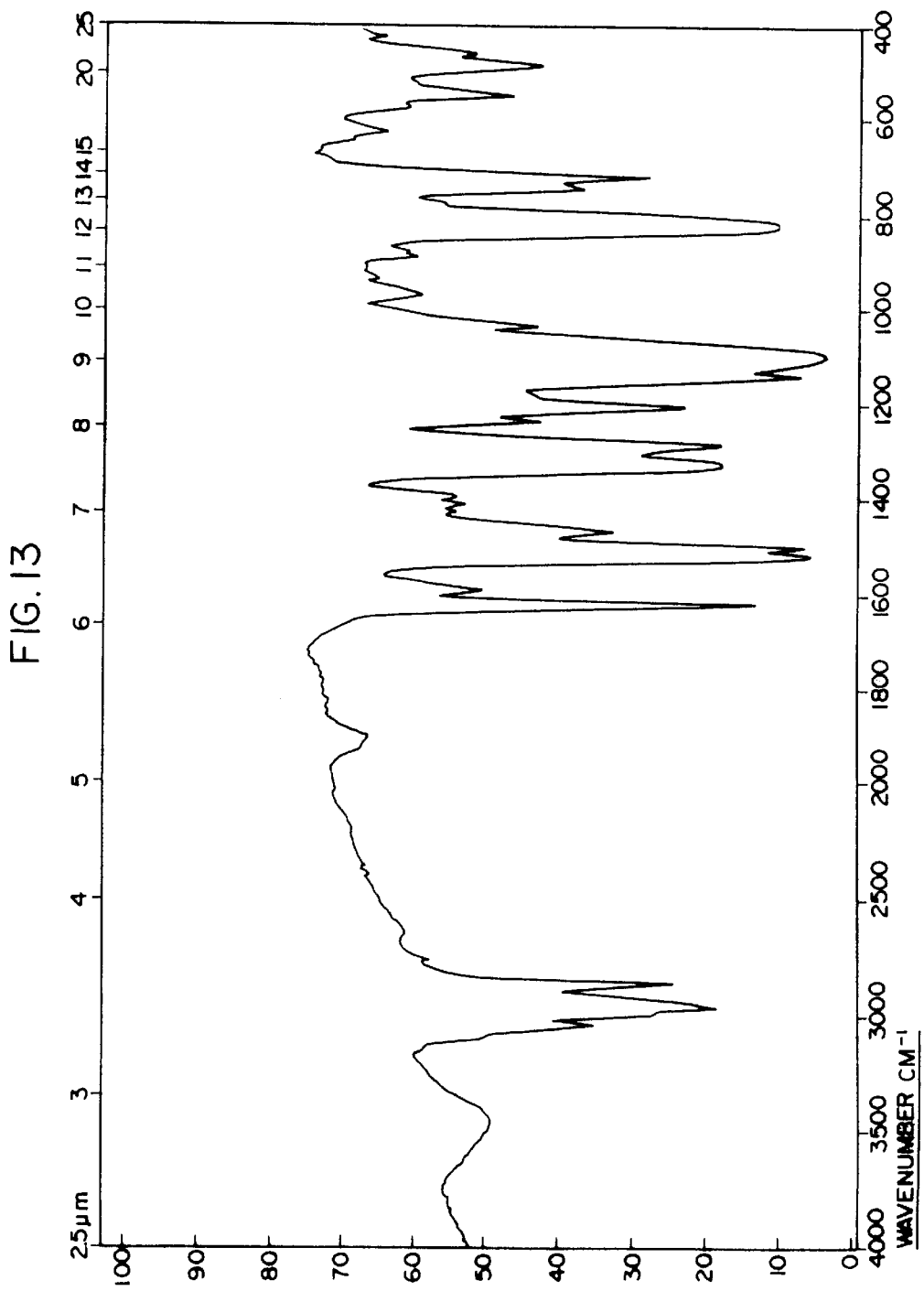
FIG. 13 shows the IR absorption spectrum of the silane compound prepared in Synthesis 10.

A pear-shaped flask was charged with 10 g of the silane compound 27 prepared in Synthesis 9, 100 mL of tetrahydrofuran and 100 mL of ethanol, and thus a solution was produced. Then, 0.4 g of 5% Pd-C was added to the solution, and thereafter the flask atmosphere was replaced with dry hydrogen gas. The reaction mixture was left to react for 16 hours at room temperature, while the gas inlet of the flask was connected to the dry hydrogen gas supply. After completion of the reaction, the Pd-C was filtered off and the solvent was removed from the solution at reduced pressure. The residue was purified by means of silica gel in a column (eluent: hexane/ethyl acetate=2/1) to give 9.2 g of silane compound 55 as a pale yellow oily product. The IR absorption spectrum of the obtained silane compound 55 is shown in FIG. 13.

Synthesis 11

Synthesis of Silane Compound 25

Figure 14:
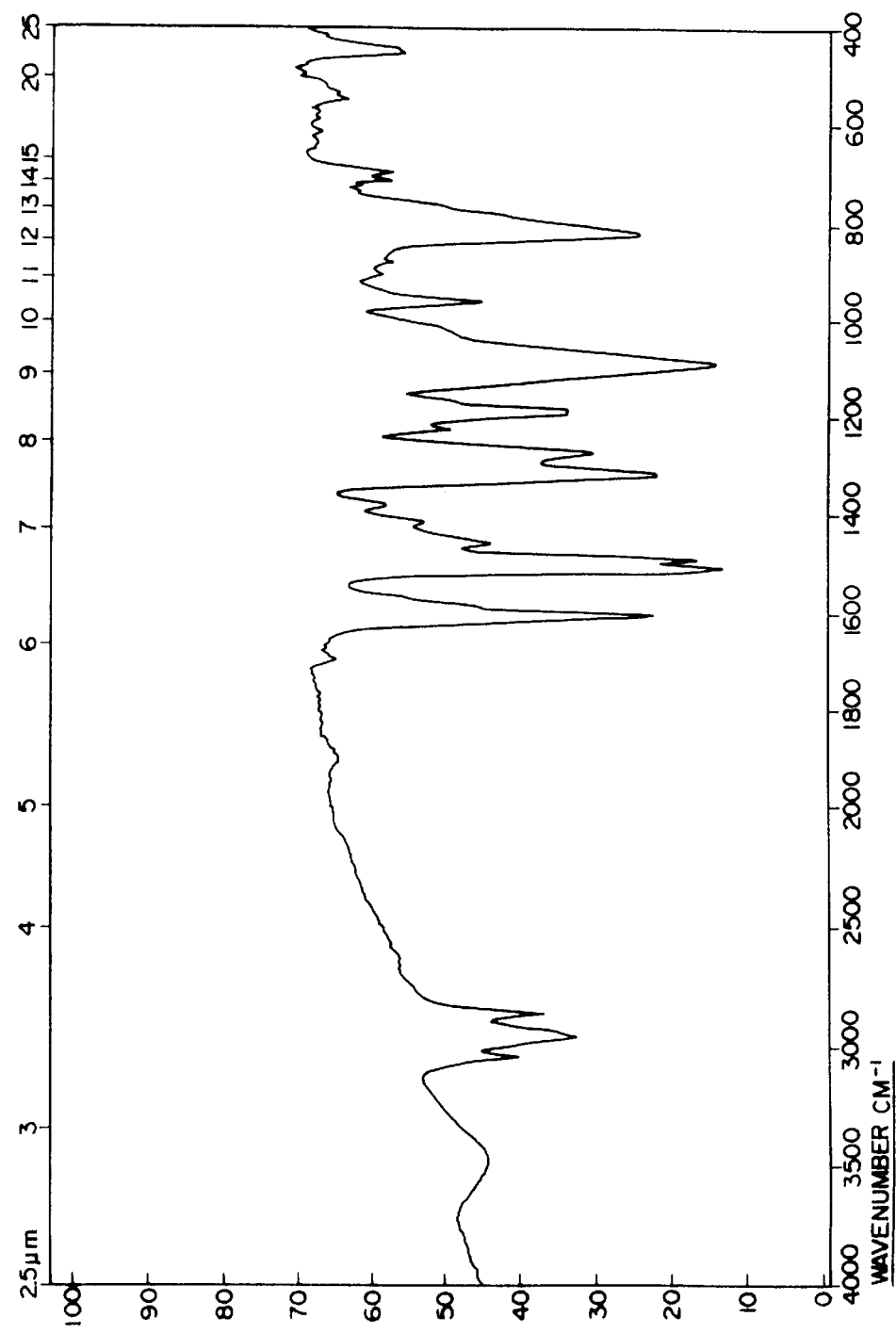
FIG. 14 shows the IR absorption spectrum of the silane compound prepared in Synthesis 11.

A two-neck flask purged with nitrogen was charged with 15 g of the phosphorus compound prepared in Synthesis 7 and 100 mL of anhydrous dimethylformamide, and thus a solution was produced. The solution was cooled down to −5° C. and 1.5 g of sodium hydride was added to the solution, which was stirred for 15 minutes. Then, while the solution was being stirred, 10.9 g of 3,3'-dimethyl-N,N'-(4-formylphenyl)-N,N'-bis(3,4-dimethylphenyl)-1,1'-biphenyl-4,4'-diamine was added to the solution, which was gradually heated up to room temperature and stirred for 2 hours. After completion of the reaction, a product was precipitated twice from the reaction solution by the two-step use of 1 L of methanol to give 13.1 g of silane compound 25 as a yellow solid product. The IR absorption spectrum of the obtained silane compound 25 is shown in FIG. 14.

Synthesis 12

Synthesis of Silane Compound 57

Figure 15:
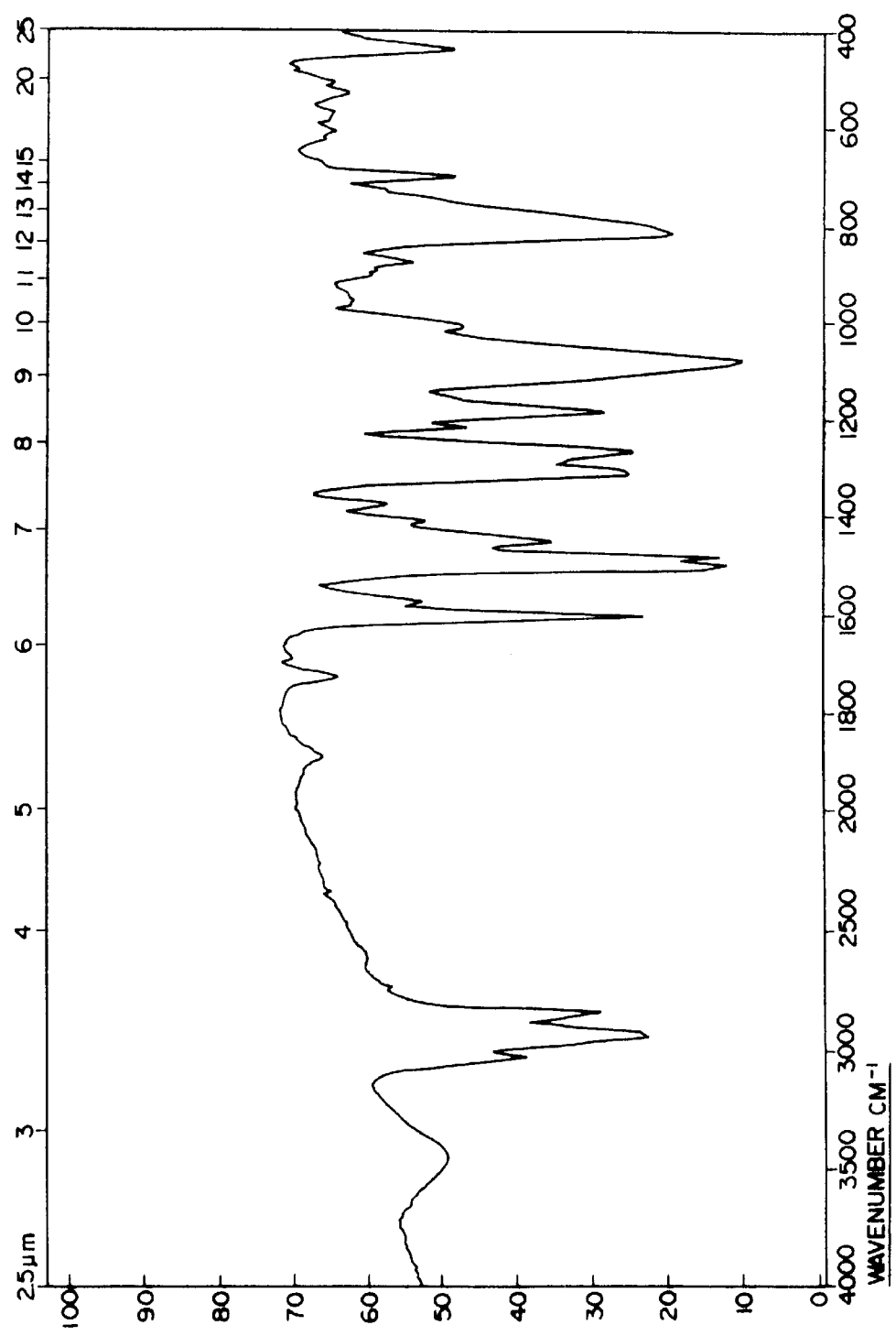
FIG. 15 shows the IR absorption spectrum of the silane compound prepared in Synthesis 12.

A pear-shaped flask was charged with 10 g of the silane compound 25 prepared in Synthesis 11, 100 mL of tetrahydrofuran and 100 mL of ethanol, and thus a solution was produced. Then, 0.5 g of 5% Pd-C was added to the solution, and thereafter the flask atmosphere was replaced with dry hydrogen gas. The reaction mixture was left to react for 16 hours at room temperature, while the gas inlet of the flask was connected to the dry hydrogen gas supply. After completion of the reaction, the Pd-C was filtered off and the solvent was removed from the solution at reduced pressure. The residue was purified by means of silica gel in a column (eluent: hexane/ethyl acetate=2/1) to give 9.1 g of silane compound 57 as a pale yellow oily product. The IR absorption spectrum of the obtained silane compound 57 is shown in FIG. 15.

Synthesis 13

Synthesis of Silane Compound 71

Figure 16:
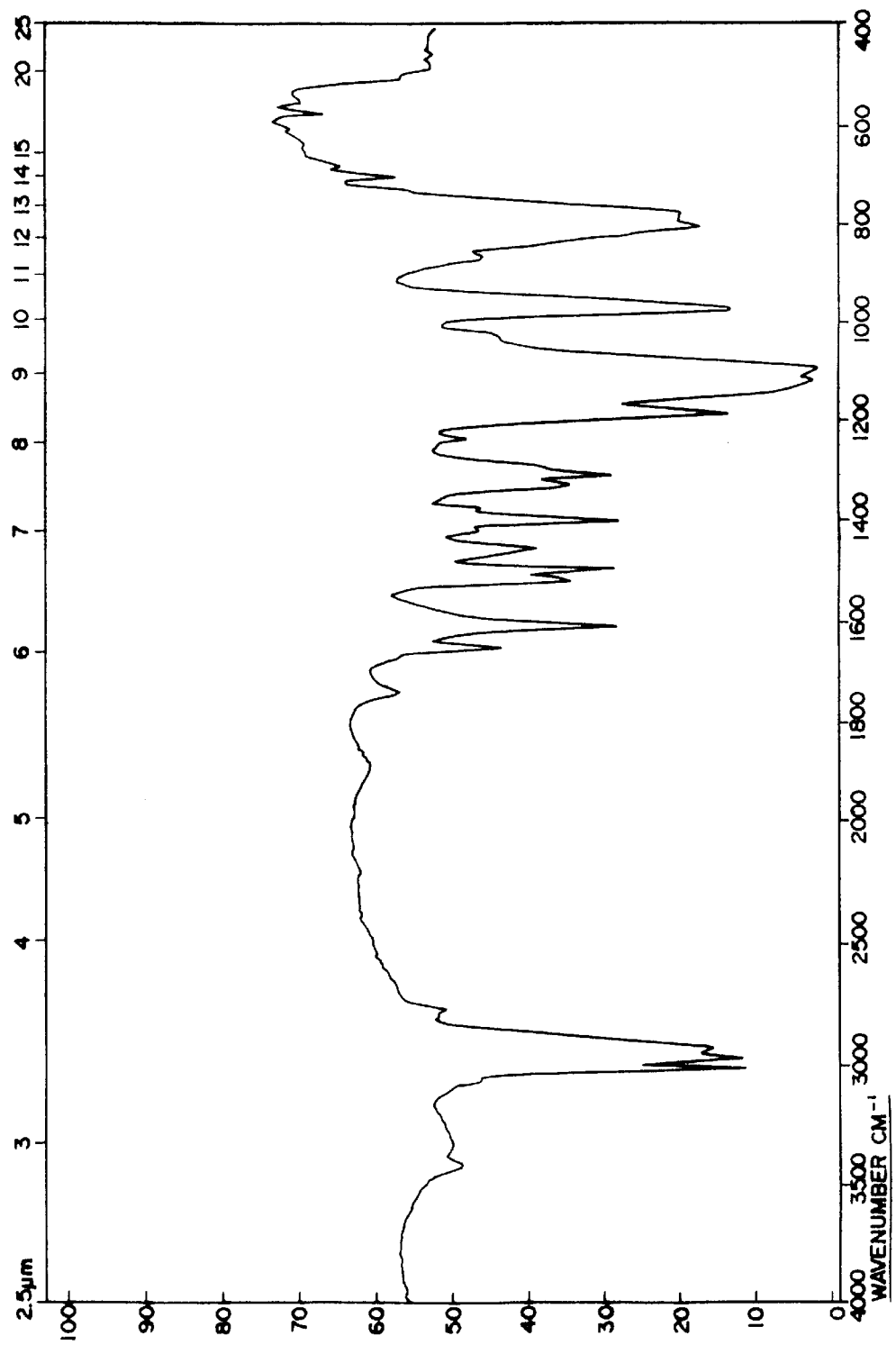
FIG. 16 shows the IR absorption spectrum of the silane compound prepared in Example 1.

A two-neck flask purged with nitrogen was charged with 10 g of N-(4-formyl)-N-(3,4-dimethylphenyl)biphenyl-4-amine and 100 mL of toluene, and thus a solution was produced. Then, 1 g of molecular sieve 4A and 0.5 g of p-toluenesulfonic acid were added to the solution. Then, 13 g of 3-aminopropyltrimethoxysilane was added dropwise to the solution over a period of 10 minutes, while the solution was stirred. The solution was then stirred for 5 hours at room temperature. After completion of the reaction, the reaction mixture was poured into 200 mL of water. Then, the mixture was extracted with toluene. The extract as an organic layer was dried with anhydrous magnesium sulfate. After removal of the solvent from the solution at reduced pressure, 13.2 g of silane compound 71 was obtained as a pale yellow oily product. The IR absorption spectrum of the obtained silane compound 71 is shown in FIG. 16.

Synthesis 14

Synthesis of Silane Compound 72

Figure 17:
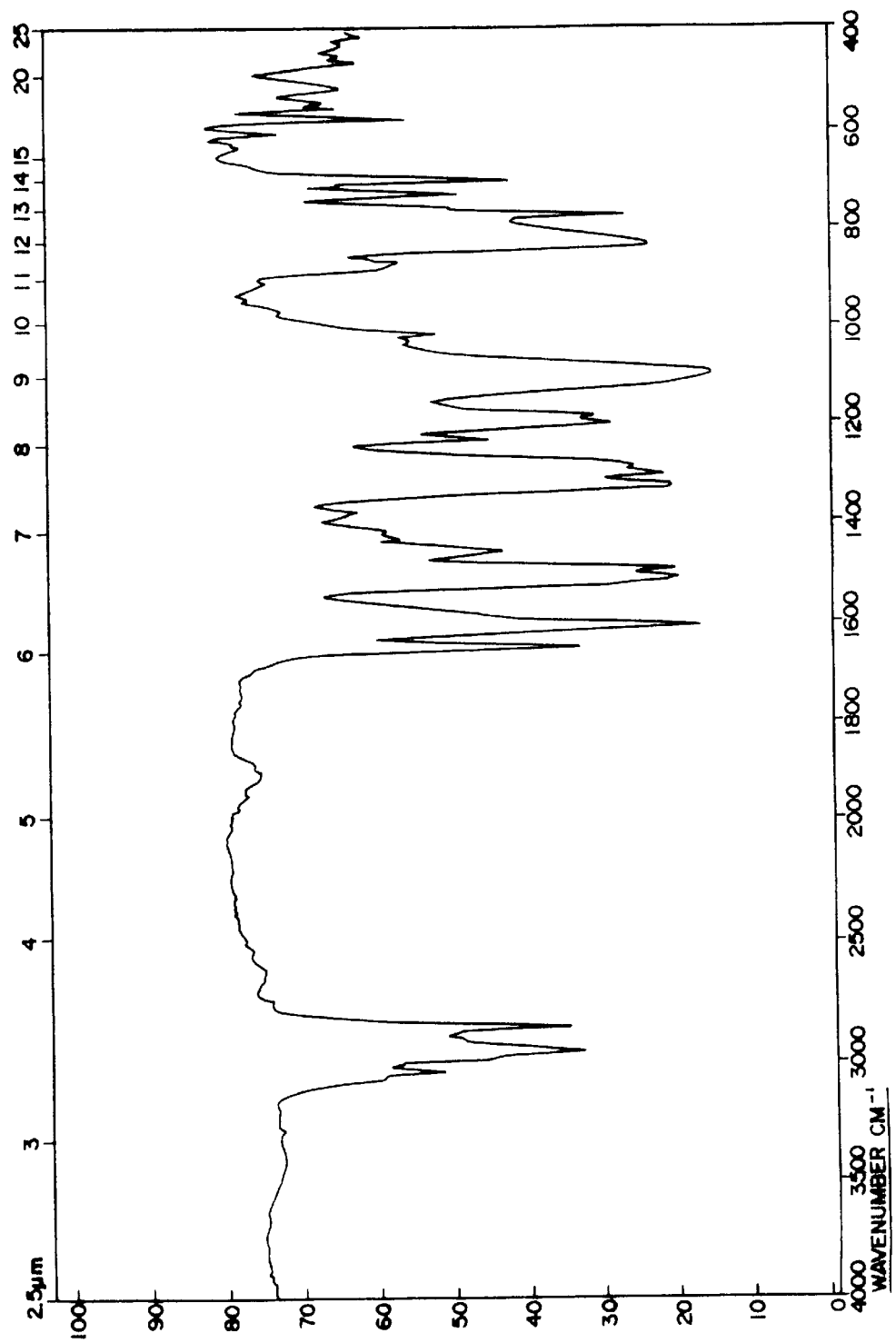
FIG. 17 shows the IR absorption spectrum of the silane compound prepared in Example 2.

A two-neck flask purged with nitrogen was charged with 10 g of N-(4-formyl)-N-(3,4-dimethylphenyl)biphenyl-4-amine and 100 mL of toluene, and thus a solution was produced. Then, 1 g of molecular sieve 4A and 0.5 g of p-toluenesulfonic acid were added to the solution. Then, 13 g of 3-aminopropyltriethoxysilane was added dropwise to the solution over a period of 10 minutes, while the solution was stirred. The solution was then stirred for 5 hours at room temperature. After completion of the reaction, the reaction mixture was poured into 200 mL of water. Then, the mixture was extracted with toluene. The extract as an organic layer was dried with anhydrous magnesium sulfate. After removal of the solvent from the solution at reduced pressure, 13 g of silane compound 72 as a pale yellow oily product was obtained. The IR absorption spectrum of the obtained silane compound 72 is shown in FIG. 17.

Synthesis 15

Synthesis of Silane Compound 85

Figure 18:
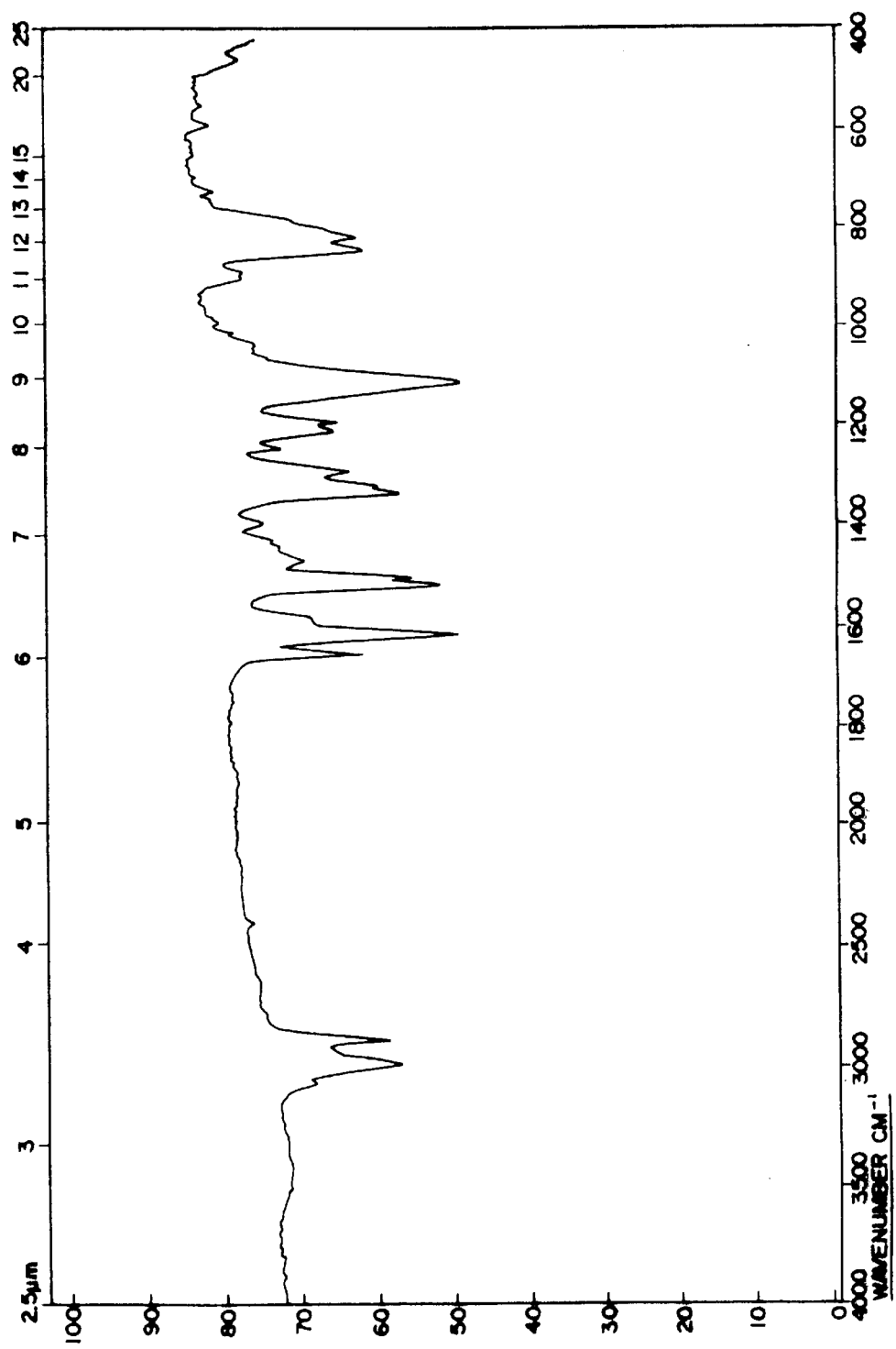
FIG. 18 shows the IR absorption spectrum of the silane compound prepared in Example 3.

A two-neck flask purged with nitrogen was charged with 10 g of 3,3'-dimethyl-N,N'-(4-formylphenyl)-N,N'-bis(3,4-dimethylphenyl)-1,1'-biphenyl-4,4'-diamine and 100 mL of toluene, and thus a solution was produced. Then, 1 g of molecular sieve 4A and 1 g of p-toluenesulfonic acid were added to the solution. Then, 12 g of 3-aminopropyltrimethoxysilane was added dropwise to the solution over a period of 10 minutes, while the solution was stirred. The solution was then stirred for 5 hours at room temperature. After completion of the reaction, the reaction mixture was poured into 200 mL of water. Then, the mixture was extracted with toluene. The extract as an organic layer was dried with anhydrous magnesium sulfate. After removal of the solvent from the solution at reduced pressure, 11 g of silane compound 85 as a pale yellow oily product was obtained. The IR absorption spectrum of the obtained silane compound 85 is shown in FIG. 18.

Synthesis 16

Synthesis of Silane Compound 86

Figure 19:
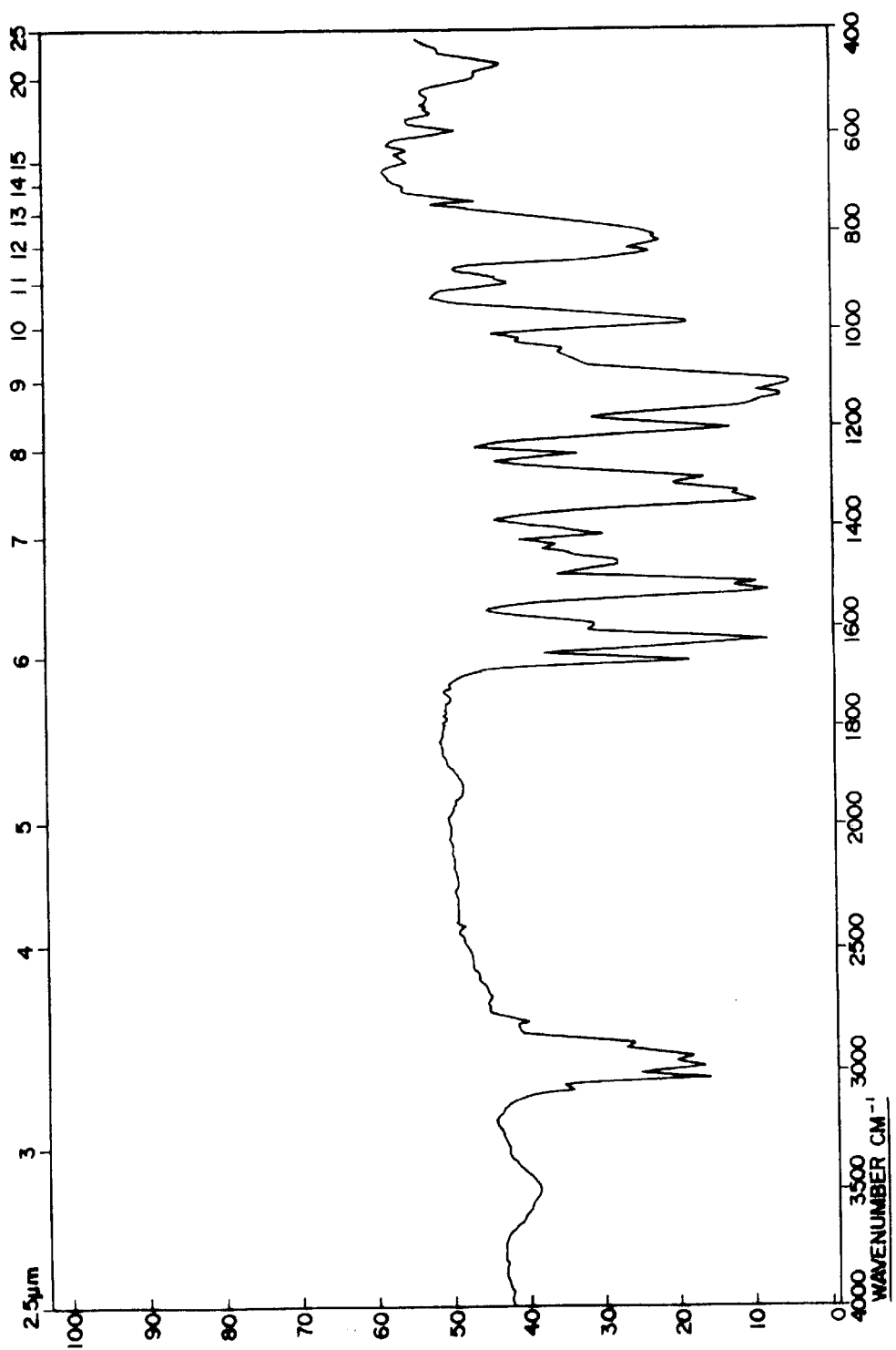
FIG. 19 shows the IR absorption spectrum of the silane compound prepared in Example 4.

A two-neck flask purged with nitrogen was charged with 10 g of 3,3'-dimethyl-N,N'-(4-formylphenyl)-N,N'-bis(3,4-dimethylphenyl)-1,1'-biphenyl-4,4'-diamine and 100 mL of toluene, and thus a solution was produced. Then, 1 g of molecular sieve 4A and 1 g of p-toluenesulfonic acid were added to the solution. Then, 15 g of 3-aminopropyltriethoxysilane was added dropwise to the solution over a period of 10 minutes, while the solution was stirred. The solution was then stirred for 5 hours at room temperature. After completion of the reaction, the reaction mixture was poured into 200 mL of water. Then, the mixture was extracted with toluene. The extract as an organic layer was dried with anhydrous magnesium sulfate. After removal of the solvent from the solution at reduced pressure, 12 g of silane compound 86 as a pale yellow oily product was obtained. The IR absorption spectrum of the obtained silane compound 86 is shown in FIG. 19.

Examples 19–22

Utilizing the silane compounds prepared in Synthesis 13 to Synthesis 16, respectively, electrophotographic photoreceptors (corresponding respectively to Examples 19–22) were prepared in the following way:

Formation of an underlayer:

To a 30-mm-diameter drum-shaped aluminum substrate, which had undergone a honing treatment, there was applied a solution, comprising 10 parts by weight of a zirconium compound (Orgatics ZC540, manufactured by Matsumoto Pharmaceuticals Manufacturing Co., Ltd.), 1 part by weight of a silane compound (A1110, manufactured by Nippon Yuncar Co., Ltd.), 40 parts by weight of isopropanol and 20 parts by weight of butanol, by means of immersion coating, and then the film was dried for 10 minutes at 150° C. to obtain an underlayer having a thickness of 0.5 µm.

Formation of a charge-generation layer:

A mixture, which comprised 1 part by weight of x-type, metal-free phthalocyanine, 1 part of a polyvinyl butyral resin (Eslec BM-S, manufactured by Sekisui Chemical Co., Ltd.) and 100 parts by weight of n-butyl acetate, was treated together with glass beads to prepare a dispersion by means of a paint shaker for 1 hour. The coating liquid thus obtained was applied onto the above-described underlayer by means of immersion coating, and then the film was dried for 10 minutes at 100° C. to form a charge-generation layer.

Formation of a charge-transport layer:

Next, 32 parts by weight of N-(4-methylphenyl)-N-(3,4-dimethylphenyl)biphenyl-4-amine and 3 parts by weight of the polycarbonate resin represented by structural formula (IV) were dissolved in 20 parts by weight of monochlorobenzene. The coating liquid thus obtained was applied onto the above-described charge-generation layer by means of immersion coating, and then the film was dried for 1 hour at 120° C. to form a charge-transport layer having a thickness of 20 µm.

Formation of a surface protective layer:

Further, 3 parts by weight of the silane compound prepared in Synthesis 13, 1 part by weight of phenyltriethoxysilane and 6 parts by weight of a silicone hardcoat material (X-40-2239, manufactured by Shin-Etsu Silicone Co., Ltd.) were dissolved in 5 parts by weight of ethyl acetate. The coating liquid thus obtained was applied onto the above-described charge-transport layer by means of immersion coating, and then the film was dried at room temperature to form a surface protective layer having a thickness of 3 µm (Example 19).

Examples 20–22

The above-described procedure was repeated except that the silane compound prepared in Synthesis 14 was used in place of the silane compound prepared in Synthesis 13, and, in this way, an electrophotographic photoreceptor (Example 20).

The above-described procedure was repeated except that the silane compound prepared in Synthesis 15 was used in place of the silane compound prepared in Synthesis 13, and, in this way, an electrophotographic photoreceptor was prepared (Example 21).

The above-described procedure was repeated except that the silane compound prepared in Synthesis 16 was used in place of the silane compound prepared in Synthesis 13, and, in this way, an electrophotographic photoreceptor was prepared (Example 22).

The electrophotographic photoreceptors (Examples 19–22) obtained in the above-described manner were mounted, respectively, on a real copying machine (XP-11, manufactured by Fuji Xerox Co., Ltd.) After a durability test by making 10,000 copies of B4 size PPC recording paper, a distinct image was obtained and the surface of the photoreceptor was free from wear, scratches, peeling, cracks, and the like.

The results indicate that the silane compounds in Examples have a superior solubility and film formability and that the obtained film is tough and stable over repeated use and resistant to variable environmental conditions.

Synthesis 17

Synthesis of Chlorogallium Phthalocyanine Crystals

Thirty parts by weight of 1,3-diiminoisoindoline and 9.1 parts by weight of gallium trichloride were placed in 230 parts by weight of quinoline, and the resulting mixture was reacted at 200° C. for 3 hours. The product was collected by filtration as a wet cake, which was washed with acetone and methanol and thereafter dried to give 28 parts by weight of crystals of chlorogallium phthalocyanine. Three parts by weight of the thus obtained chlorogallium phthalocyanine crystals was dry-ground by means of an automatic mortar (Lab-Mill UT-21, manufactured by Yamato Science Co., Ltd.) for 3 hours. Then, 0.5 parts by weight of the dry-ground crystals was milled by means of 60 parts by weight of glass beads (1 mm diameter) together with 20 parts by weight of benzyl alcohol for 24 hours at room temperature. After separating the glass beads by filtration, the wet product was washed with 10 parts by weight of methanol, and thereafter dried to give crystals of chlorogallium phthalocyanine (CG-1), whose powder X-ray diffraction spectrum ($2\theta \pm 0.2°$) exhibited strong peaks at 7.4°, 16.6°, 25.5°, and 28.3°.

Synthesis 18

Synthesis of Dichlorotin Phthalocyanine Crystals

Fifty parts by weight of phthalonitrile and 27 g of anhydrous tin II chloride were placed in 350 mL of 1-chloronaphthalene, and the resulting mixture was reacted at 195° C. for 5 hours. The product was collected by filtration as a wet cake, which was washed with 1-chloronaphthalene, acetone, methanol and water in that order and thereafter dried at reduced pressure to give 18.3 g of crystals of dichlorotin phthalocyanine. Five g of the thus obtained crystals of dichlorotin phthalocyanine, 10 g of sodium chloride and 500 g of agate balls (20 mm diameter) were placed in an agate pot, which was set to grinding by means of a planetary ball mill apparatus (P-5 type, manufactured by Fritz Co., Ltd.) at 400 rpm for 10 hours. After separating the agate balls, the wet product was sufficiently washed with water, and thereafter dried. Then, 0.5 parts by weight of the ground product was milled by means of 30 parts by weight of glass beads (1 mm diameter) together with 15 parts by weight of tetrahydrofuran for 24 hours at room temperature. After separating the glass beads by filtration, the wet product was washed with methanol, and thereafter dried to give crystals of dichlorotin phthalocyanine (CG-2), whose powder X-ray diffraction spectrum ($2\theta \pm 0.2°$) exhibited strong peaks at 8.5°, 11.2°, 14.5°, and 27.2°.

Synthesis 19

Synthesis of Hydroxygallium Phthalocyanine Crystals

Three parts by weight of the chlorogallium phthalocyanine crystals prepared in Synthesis 17 was dissolved in 60 parts by weight of concentrated sulfuric acid at 0° C. The resulting solution was added drop-wise to 450 parts by weight of distilled water at 5° C. so that the crystals would deposit again. After washing the deposited product with distilled water and dilute ammonia water, the product was dried to give 2.5 parts by weight of hydroxygallium phthalocyanine crystals, which were dry-ground by means of an automatic mortar (Lab-Mill UT-21, manufactured by Yamato Science Co., Ltd.) for 5.5 hours. Then, 0.5 parts by weight of the dry-ground crystals was milled by means of 30 parts by weight of glass beads (1 mm diameter) together with 20 parts by 15 parts by weight of dimethylformamide for 24 hours at room temperature. After separating the glass beads by filtration, the wet product was washed with methanol, and thereafter dried to give crystals of hydroxygallium phthalocyanine (CG-3), whose powder X-ray diffraction spectrum (2θ±0.2°) exhibited strong peaks at 7.5°, 9.9°, 12.5°, 16.3°, 18.6°, 25.1°, and 28.3°.

Synthesis 20

Synthesis of Oxytitanium Phthalocyanine Crystals

Thirty parts by weight of 1,3-diiminoisoindoline and 17 parts by weight of titanium tetrabutoxide were placed in 200 parts by weight of 1-chloronaphthalene, and the resulting mixture was reacted under a nitrogen gas stream at 190° C. for 5 hours. The product was collected by filtration as a wet cake, which was washed with ammonia water, water, and acetone and thereafter dried to give 40 parts by weight of crystals of oxytitanium phthalocyanine. Five parts by weight of the thus obtained oxytitanium phthalocyanine and 10 parts by weight of sodium chloride were dry-ground by means of an automatic mortar (Lab-Mill UT-21, manufactured by Yamato Science Co., Ltd.) for 3 hours. The ground crystals were sufficiently washed with distilled water and thereafter dried to give 4.8 parts by weight of oxytitanium phthalocyanine cyrstals, whose powder X-ray diffraction spectrum (2θ±0.2°) exhibited a distinct peak at 27.3°. Then, 2 parts by weight of the foregoing oxytitanium phthalocyanine crystals was stirred in a solvent mixture comprising 20 parts by weight of distilled water and 2 parts by weight of monochlorobenzene at 50° C. for 1 hour. After collecting the product by filtration, the wet product was sufficiently washed with methanol, and thereafter dried to give crystals of oxytitanium phthalocyanine (CG-4), whose powder X-ray diffraction spectrum (2θ±0.2°) exhibited a strong peak at 27.3°.

Example 23

Formation of an underlayer:

To a 30-mm-diameter drum-shaped aluminum substrate, which had undergone a honing treatment, there was applied a solution, comprising 10 parts by weight of a zirconium compound (Orgatics ZC540, manufactured by Matsumoto Pharmaceuticals Manufacturing Co., Ltd.), 1 part by weight of a silane compound (A1110, manufactured by Nippon Yuncar Co., Ltd.), 400 parts by weight of isopropanol and 200 parts by weight of butanol, by means of immersion coating, and then the film was dried for 10 minutes at 150° C. to obtain an underlayer having a thickness of 0.5 μm.

Formation of a charge-generation layer:

A mixture, which comprised 10 parts by weight of the chlorogallium phthalocyanine prepared in synthesis 18, 10 parts by weight of a polyvinyl butyral resin (Eslec BM-S, manufactured by Sekisui Chemical Co., Ltd.) and 500 parts by weight of n-butyl acetate, was treated together with glass beads to prepare a dispersion by means of a paint shaker for 1 hour. The coating liquid thus obtained was applied to the above-described underlayer by means of immersion coating, and then the film was dried for 10 minutes at 100° C. to form a charge-generation layer having a thickness of 0.18 μm.

Formation of a charge-transport layer:

Next, 2 parts by weight of N-(4-methylphenyl)-N-(3,4-dimethylphenyl)biphenyl-4-amine (CT-1) and 3 parts by weight of 1,1'-di-(p-phynylene)cyclohexane carbonate were dissolved in 20 parts by weight of monochlorobenzene. The coating liquid thus obtained was applied onto the above-described charge-generation layer by means of immersion coating, and then the film was dried for 1 hour at 120° C. to form a charge-transport layer having a thickness of 15 μm.

Formation of a surface protective layer:

Further, 10 parts by weight of the silane compound (1) prepared in Synthesis 1, 20 parts by weight of a silicone hardcoat material (X-40-2239, manufactured by Shin-Etsu Silicone Co., Ltd.), 3 parts by weight of phenyltriethoxysilane and 1 part by weight of acetic acid were mixed together. The coating liquid thus obtained was applied onto the above-described charge-transport layer by means of immersion coating, and then the film was cured at 100° C. for 1 hour to form a surface protective layer having a thickness of 3 μm.

The electrophotographic photoreceptor obtained in the above-described manner was mounted on a laser beam printer (XP-11, manufactured by Fuji Xerox Co., Ltd.) After a printing test in a condition of high temperature and high humidity (35° C. and 80% RH), the 1st copy and 2,000th copy were evaluated for image quality. The results are shown in Table 7.

Examples 24–31

The procedure of Example 23 was repeated except that the combinations of charge-generation material and silane compound of Table 7 were employed. The prepared electrophotographic photoreceptors were evaluated and the results are shown in Table 7.

Examples 32–37

The procedure of Examples 23–31 was repeated except that N,N-diphenyl-N,N'-bis-(m-tolyl)benzidine (CT-2) was used as the charge-transport material. The prepared electrophotographic photoreceptors were evaluated and the results are shown in Table 7.

Example 38

As in Examples 23–37, an underlayer having a thickness of 0.5 μm was formed on a drum-shaped aluminum substrate and a charge-generation layer, which used the chlorogallium phthalocyanine crystals prepared in Synthesis 17 and had a thickness of 0.17 μm, was formed on the underlayer.

Then, 1 part by weight of the silane compound 1 prepared in Synthesis 1 as a charge-transport material and 1 part by weight polycarbonate resin represented by structural formula II as a binder polymer were dissolved in 8 parts by weight of monochlorobenzene and 1 part by weight of acetic acid. The coating liquid thus obtained was applied to the above-described charge-generation layer by means of immersion coating, and then the film was dried for 1 hour at 100° C. to form a charge-transport layer having a thickness of 15 μm.

The electrophotographic photoreceptors were evaluated as in Examples 23–37 and the results are shown in Table 7.

Examples 39–49

The procedure of Example 38 was repeated except that the binder polymers and the silane compounds were changed as shown in Table 7. The prepared electrophotographic photoreceptors were evaluated and the results are shown in Table 7.

Comparative Example 2

As in Examples 23–49, an underlayer having a thickness of 0.5 μm was formed on a drum-shaped aluminum substrate and a charge-generation layer, which used the chlorogallium phthalocyanine crystals prepared in Synthesis 17 and had a thickness of 0.15 μm, was formed on the underlayer.

Then, 2 parts by weight of triphenylamine as a charge-transport material and 1 part by weight polycarbonate resin represented by structural formula II as a binder polymer were dissolved in 8 parts by weight of monochlorobenzene. The coating liquid thus obtained was applied to the above-described charge-generation layer by means of immersion coating, and then the film was dried for 1 hour at 100° C. to form a charge-transport layer having a thickness of 16 μm.

The electrophotographic photoreceptors were evaluated as in Examples 23–49 and the results are shown in Table 7.

TABLE 7

| Example | Compound No. | Charge-generation material | Charge-transport material | Image quality (copy) 1st | 2,000th |
|---|---|---|---|---|---|
| 23 | 1 | CG-1 | CT-1 | Good | Good |
| 24 | 1 | CG-2 | CT-1 | Good | Good |
| 25 | 1 | CG-3 | CT-1 | Good | Good |
| 26 | 1 | CG-4 | CT-1 | Good | Good |
| 27 | 71 | CG-1 | CT-1 | Good | Good |
| 28 | 72 | CG-1 | CT-1 | Good | Good |
| 29 | 23 | CG-1 | CT-1 | Good | Good |
| 30 | 86 | CG-1 | CT-1 | Good | Good |
| 31 | 51 | CG-1 | CT-1 | Good | Good |
| 32 | 1 | CG-1 | CT-2 | Good | Good |
| 33 | 71 | CG-1 | CT-2 | Good | Good |
| 34 | 72 | CG-1 | CT-2 | Good | Good |
| 35 | 23 | CG-1 | CT-2 | Good | Good |

TABLE 7-continued

| 36 | 86 | CG-1 | CT-2 | Good | Good |
| 37 | 51 | CG-1 | CT-2 | Good | Good |

| Example | Compound No. | CTL binder | Image quality (copy) 1st | 2,000th |
|---|---|---|---|---|
| 38 | 1 | II | Good | Good |
| 39 | 1 | III | Good | Good |
| 40 | 1 | IV | Good | Good |
| 41 | 1 | V | Good | Good |
| 42 | 1 | VI | Good | Good |
| 43 | 1 | VII | Good | Good |
| 44 | 34 | III | Good | Good |
| 45 | 34 | IV | Good | Good |

TABLE 7-continued

| 46 | 23 | III | Good | Good |
| 47 | 23 | IV | Good | Good |
| 48 | 104 | III | Good | Good |
| 49 | 104 | IV | Good | Good |
| CE 2 | NPh₃ | II | Good | Partial fogging observed |

CE: Comparative Example

Examples 50–68

The procedure of Examples 24–31 was repeated except that the combinations of charge-generation material and silane compound of Table 8 were employed. The prepared electrophotographic photoreceptors were evaluated and the results are shown in Table 8.

Comparative Example 3

As in Examples, an underlayer having a thickness of 0.5 μm was formed on a drum-shaped aluminum substrate. Then, a charge-generation layer, which used the chlorogallium phthalocyanine crystals prepared in Synthesis 17 and had a thickness of 0.15 μm, was formed on the underlayer. Further, a charge-transport layer, which used N,N-bis(3,4-dimethylphenyl)biphenyl-4-amine (CT-1) and had a thickness of 15 μm, was formed on the charge-generation layer.

Furthermore, 10 parts by weight of silane compound CT-3 represented by the following structural formula, 20 parts by weight of a silicone hardcoat material (X-40-2239, manufactured by Shin-Etsu Silicone Co., Ltd.), 3 parts by weight of phenyltriethoxysilane and 1 part by weight of acetic acid were mixed together. The coating liquid thus obtained was applied onto the above-described charge-transport layer by means of immersion coating, and then the film was thermally cured at 100° C. to form a surface protective layer having a thickness of 2.5 μm. In this way, an electrophotographic photoreceptor was prepared. Structural formula

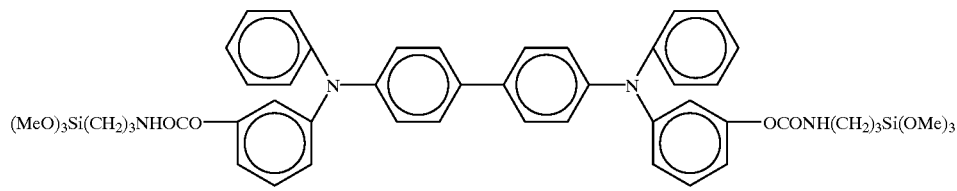

The thus obtained electrophotographic photoreceptor was evaluated as in Examples and the results are shown in Table 8.

Examples 69–88

The procedure of Examples 38–51 was repeated except that the combinations of charge-generation material and silane compound of Table 9 were employed. The prepared electrophotographic photoreceptors were evaluated and the results are shown in Table 9.

Comparative Example 4

The procedure of Comparative Examples 3 was repeated except that silane compound CT-3, which was used in Comparative Example 3, was used as the charge-transport material. The prepared electrophotographic photoreceptor was evaluated and the results are shown in Table 9.

As is apparent from the table, because of the use of the silane compound, which is superior in properties, namely, solubility, film formability and compatibility, the photoreceptors of Examples have a tough film and therefore exhibit a superior mechanical strength and stability in repeated use and further exhibit a high sensitivity.

TABLE 8

| Example | Compound No. | Charge-generation material | Charge-transport material | Image quality (copy) 1st | Image quality (copy) 2,000th |
| --- | --- | --- | --- | --- | --- |
| 50 | 7 | CG-1 | CT-1 | Good | Good |
| 51 | 38 | CG-1 | CT-1 | Good | Good |
| 52 | 38 | CG-2 | CT-1 | Good | Good |
| 53 | 38 | CG-3 | CT-1 | Good | Good |
| 54 | 38 | CG-4 | CT-1 | Good | Good |
| 55 | 5 | CG-1 | CT-1 | Good | Good |
| 56 | 39 | CG-1 | CT-1 | Good | Good |
| 57 | 27 | CG-1 | CT-1 | Good | Good |
| 58 | 55 | CG-1 | CT-1 | Good | Good |
| 59 | 25 | CG-1 | CT-1 | Good | Good |
| 60 | 57 | CG-1 | CT-1 | Good | Good |
| 61 | 7 | CG-1 | CT-2 | Good | Good |
| 62 | 38 | CG-1 | CT-2 | Good | Good |
| 63 | 5 | CG-1 | CT-2 | Good | Good |
| 64 | 39 | CG-1 | CT-2 | Good | Good |
| 65 | 27 | CG-1 | CT-2 | Good | Good |
| 66 | 55 | CG-1 | CT-2 | Good | Good |
| 67 | 25 | CG-1 | CT-2 | Good | Good |
| 68 | 57 | CG-1 | CT-2 | Good | Good |
| CE 3 | CT-3 | CG-1 | CT-1 | Some image drift | Some image drift |

CE: Comparative Example

TABLE 9

| Example | Compound No. | CTL binder | Image quality (copy) 1st | Image quality (copy) 2,000th |
| --- | --- | --- | --- | --- |
| 69 | 7 | VI | Good | Good |
| 70 | 7 | VII | Good | Good |
| 71 | 38 | II | Good | Good |
| 72 | 38 | III | Good | Good |
| 73 | 38 | IV | Good | Good |
| 74 | 38 | V | Good | Good |
| 75 | 38 | VI | Good | Good |
| 76 | 38 | VII | Good | Good |
| 77 | 5 | III | Good | Good |
| 78 | 5 | IV | Good | Good |
| 79 | 39 | III | Good | Good |
| 80 | 39 | IV | Good | Good |
| 81 | 27 | III | Good | Good |
| 82 | 27 | IV | Good | Good |
| 83 | 55 | III | Good | Good |
| 84 | 55 | IV | Good | Good |
| 85 | 25 | III | Good | Good |
| 86 | 25 | IV | Good | Good |
| 87 | 57 | III | Good | Good |
| 88 | 57 | IV | Good | Good |
| CE 4 | CT-3 | II | Some image drift | Some image drift |

CE: Comparative Example

As is apparent from the table, because of the use of the silane compound, which is superior in properties, namely, solubility, film formability and compatibility, the photoreceptors of Examples have a tough film and therefore exhibit a superior mechanical strength and stability in repeated use and further exhibit a high sensitivity.

Example 67

Formation of an underlayer:

To a 30-mm-diameter drum-shaped aluminum substrate, which had undergone a honing treatment, there was applied a solution, comprising 100 parts by weight of a zirconium compound (Orgatics ZC540, manufactured by Matsumoto Pharmaceuticals Manufacturing Co., Ltd.), 10 part by weight of a silane compound (A1110, manufactured by Nippon Yuncar Co., Ltd.), 400 parts by weight of isopropanol and 200 parts by weight of butanol, by means of immersion coating, and then the film was dried for 10 minutes at 150° C. to obtain an underlayer having a thickness of 0.5 μm.

Formation of a charge-generation layer:

A mixture, which comprised 10 parts by weight of chlorogallium phthalocyanine crystals prepared in Synthesis 17, 10 parts by weight of a polyvinyl butyral resin (Eslec BM-S, manufactured by Sekisui Chemical Co., Ltd.) and 500 parts by weight of n-butyl acetate, was treated together with glass beads to prepare a dispersion by means of a paint shaker for 1 hour. The coating liquid thus obtained was applied onto the above-described underlayer by means of immersion coating, and then the film was dried for 10 minutes at 100° C. to form a charge-generation layer having a thickness of 0.18 μm.

Formation of a charge-transport layer:

Next, 2 parts by weight of N,N-bis(3,4-dimethylphenyl) biphenyl-4-amine (CTM-1) and 3 parts by weight of 1,1'-di-(p-phenylene)cyclohexane carbonate were dissolved in 20 parts by weight of monochlorobenzene. The coating liquid thus obtained was applied onto the above-described charge-generation layer by means of immersion coating, and then the film was dried for 1 hour at 120° C. to form a charge-transport layer having a thickness of 15 μm.

Formation of a surface protective layer:

Further, 10 parts by weight of silane compound 1, 20 parts by weight of a silicone hardcoat material (X-40-2239, manufactured by Shin-Etsu Silicone Co., Ltd.), 3 parts by weight of PTFE as a fluorine-containing compound, 1 part by weight of 1N hydrochloric acid and 30 parts by weight of dibutyl ether were mixed together for 15 minutes. The coating liquid thus obtained was applied onto the above-described charge-transport layer by means of immersion coating, and then the film was dried at 120° C. for 1 hour, followed by hardening treatment of 1.5 hours at 80° C. (80%RH), to form a surface protective layer having a thickness of 3 μm. In this way, an electrophotographic photoreceptor was prepared.

The electrophotographic photoreceptor obtained in the above-described manner was mounted on a real copying machine (XP-11, manufactured by Fuji Xerox Co., Ltd.) A durability test by making 10,000 copies of B4 size PPC recording paper was conducted and the results are shown in Table 11.

Examples 90–138

The procedure of Example 23 was repeated except that the combinations of the compound represented by general formula I, the fluorine-containing compound and the catalyst of Table 10 were employed, and, in this way, electrophotographic photoreceptors were prepared and evaluated. The results are shown in Table 11.

Comparative Example 5

The procedures of preceding Examples were repeated except that no surface protective layer was formed. In this way, electrophotographic photoreceptors were prepared. Similar evaluation was conducted and the results are shown in Table 11.

Comparative Examples 6–14

The procedure of Examples of 90–138 was repeated except that N,N-bis(3,4-dimethylphenyl)biphenyl-4-amine (CTM-1) was used as a charge-transport material in place of the compound represented by general formula I and the combinations of the fluorine-containing compound and the catalyst of Table 10 were employed to form protective layers. However, none of the protective layers was of acceptable quality because of defects such as whitening.

Comparative Example 15

The procedure of Examples of 90–138 was repeated except that N,N-bis(3,4-dimethylphenyl)biphenyl-4-amine (CTM-1) was used as a charge-transport material in place of the compound represented by general formula I and the polycarbonate represented by structural formula IV was used as a binder and $F(CF_2)_8CH_2CH_2Si(OMe)_3$ was used as a fluorine-containing compound to form a protective layer. However, the protective layer was not of acceptable quality, because defects such as whitening occurred due to insufficient compatibility.

As is apparent from Tables 15–17, the electrophotographic photoreceptors of Examples, which contain the compound represented by general formula I and the fluorine-containing compound, have a tough film and are superior in durability and stability to environmental conditions and exhibit a high sensitivity. Meanwhile, no suitable protective surface is formed in the case where an electrophotographic photoreceptor does not contain the compound represented by general formula I, even if it contains the fluorine-containing compound.

TABLE 10

| Example | Compound No. | Fluorine-containing compound | Catalyst | Others |
|---|---|---|---|---|
| 89 | 1 | PTFE | | |
| 90 | 71 | PTFE | 1N-HCl | |
| 91 | 34 | PTFE | 1N-HCl | |
| 92 | 23 | PTFE | 1N-HCl | |
| 93 | 85 | PTFE | 1N-HCl | |
| 94 | 51 | PTFE | 1N-HCl | |
| 95 | 1 | $CF_3CF_3CH_2OMe$ | 1N-HCl | |
| 96 | 71 | $CF_3CF_3CH_2OMe$ | 1N-HCl | |
| 97 | 34 | $CF_3CF_3CH_2OMe$ | 1N-HCl | |
| 98 | 23 | $CF_3CF_3CH_2OMe$ | 1N-HCl | |
| 99 | 85 | $CF_3CF_3CH_2OMe$ | 1N-HCl | |
| 100 | 51 | $CF_3CF_3CH_2OMe$ | 1N-HCl | |
| 101 | 1 | $F(CF_2)_7COOMe$ | 1N-HCl | |
| 102 | 71 | $F(CF_2)_7COOMe$ | 1N-HCl | |
| 103 | 34 | $F(CF_2)_7COOMe$ | 1N-HCl | |
| 104 | 23 | $F(CF_2)_7COOMe$ | 1N-HCl | |
| 105 | 85 | $F(CF_2)_7COOMe$ | 1N-HCl | |
| 106 | 51 | $F(CF_2)_7COOMe$ | 1N-HCl | |
| 107 | 1 | $F(CF_2)_7COOH$ | 1N-HCl | |
| 108 | 71 | $F(CF_2)_7COOH$ | 1N-HCl | |
| 109 | 34 | $F(CF_2)_7COOH$ | 1N-HCl | |
| 110 | 23 | $F(CF_2)_7COOH$ | 1N-HCl | |
| 111 | 85 | $F(CF_2)_7COOH$ | 1N-HCl | |
| 112 | 51 | $F(CF_2)_7COOH$ | 1N-HCl | |
| 113 | 1 | $F(CF_2)_7CH_2NH_2$ | 1N-HCl | |
| 114 | 71 | $F(CF_2)_7CH_2NH_2$ | 1N-HCl | |
| 115 | 34 | $F(CF_2)_7CH_2NH_2$ | 1N-HCl | |
| 116 | 23 | $F(CF_2)_7CH_2NH_2$ | 1N-HCl | |
| 117 | 85 | $F(CF_2)_7CH_2NH_2$ | 1N-HCl | |
| 118 | 51 | $F(CF_2)_7CH_2NH_2$ | 1N-HCl | |
| 119 | 1 | $F(CF_2)_8CH_2CCH_2OH$ | 1N-HCl | |
| 120 | 71 | $F(CF_2)_8CH_2CCH_2OH$ | 1N-HCl | |
| 121 | 34 | $F(CF_2)_8CH_2CCH_2OH$ | 1N-HCl | |
| 122 | 23 | $F(CF_2)_8CH_2CCH_2OH$ | 1N-HCl | |
| 123 | 85 | $F(CF_2)_8CH_2CCH_2OH$ | 1N-HCl | |
| 124 | 51 | $F(CF_2)_8CH_2CCH_2OH$ | 1N-HCl | |
| 125 | 1 | $F(CF_2)_8CH=CH_2$ | 1N-HCl | $H_2PtCl_6 6H_2O$/ 0.1 part $PhSi(OEt)_2H$/ 4 parts |
| 126 | 23 | $F(CF_2)_8CH=CH_2$ | 1N-HCl | $H_2PtCl_6 6H_2O$/ 0.1 part $PhSi(OEt)_2H$/ 4 parts |
| 127 | 1 | $F(CF_2)_8CH_2CH_2Si(OMe)_3$ | 1N-HCl | |
| 128 | 71 | $F(CF_2)_8CH_2CH_2Si(OMe)_3$ | 1N-HCl | |
| 129 | 34 | $F(CF_2)_8CH_2CH_2Si(OMe)_3$ | 1N-HCl | |
| 130 | 23 | $F(CF_2)_8CH_2CH_2SI(OMe)_3$ | 1N-HCl | |
| 131 | 85 | $F(CF_2)_8CH_2CH_2Si(OMe)_3$ | 1N-HCl | |
| 132 | 51 | $F(CF_2)_8CH_2CH_2Si(OMe)_3$ | 1N-HCl | |
| 133 | 1 | $CF_3CH_2CH_2Si(OMe)_3$ | 1N-HCl | |
| 134 | 71 | $CF_3CH_2CH_2Si(OMe)_3$ | 1N-HCl | |
| 135 | 34 | $CF_3CH_2CH_2Si(OMe)_3$ | 1N-HCl | |
| 136 | 23 | $CF_3CH_2CH_2Si(OMe)_3$ | 1N-HCl | |
| 137 | 85 | $CF_3CH_2CH_2SI(OMe)_3$ | 1N-HCl | |
| 138 | 51 | $CF_3CH_2CH_2Si(OMe)_3$ | 1N-HCl | |
| CE 6 | CTM-1 | PTFE | 1N-HCl | |
| CE 7 | CTM-1 | $CF_3CF_2CH_2OMe$ | 1N-HCl | |
| CE 8 | CTM-1 | $F(CF_2)_7COOMe$ | 1N-HCl | |
| CE 9 | CTM-1 | $F(CF_2)_7COOH$ | 1N-HCl | |
| CE 10 | CTM-1 | $F(CF_2)_7CH_2NH_2$ | 1N-HCl | |
| CE 11 | CTM-1 | $F(CF_2)_8CH_2CH_2OH$ | 1N-HCl | |
| CE 12 | CTM-1 | $F(CF_2)_8CH=CH_2$ | 1N-HCl | $H_2PtCl_6 6H_2O$/ 0.1 part $PhSi(OEt)_2H$/ 4 parts |
| CE 13 | CTM-1 | $F(CF_2)_8CH_2CH_2Si(OMe)_3$ | 1N-HCl | |
| CE 14 | CTM-1 | $CF_3CH_2CH_2Si(OMe)_3$ | 1N-HCl | |

TABLE 11

| | State after making 10,000 copies | | | |
|---|---|---|---|---|
| Example | Copy image quality | Photoreceptor wear (nm) | Photoreceptor surface state | Adherence to photoreceptor |
| 89 | Good | 410 | Good | None |
| 90 | Good | 436 | Good | None |
| 91 | Good | 414 | Good | None |
| 92 | Good | 403 | Good | None |
| 93 | Good | 409 | Good | None |
| 94 | Good | 405 | Good | None |
| 95 | Good | 650 | Good | None |
| 96 | Good | 679 | Good | None |
| 97 | Good | 652 | Good | None |
| 98 | Good | 613 | Good | None |
| 99 | Good | 608 | Good | None |
| 100 | Good | 604 | Good | None |
| 101 | Good | 483 | Good | None |
| 102 | Good | 503 | Good | None |
| 103 | Good | 472 | Good | None |
| 104 | Good | 426 | Good | None |
| 105 | Good | 411 | Good | None |
| 106 | Good | 416 | Good | None |
| 107 | Good | 497 | Good | None |
| 108 | Good | 489 | Good | None |
| 109 | Good | 494 | Good | None |
| 110 | Good | 478 | Good | None |
| 111 | Good | 481 | Good | None |
| 112 | Good | 475 | Good | None |
| 113 | Good | 375 | Good | None |
| 114 | Good | 369 | Good | None |
| 115 | Good | 381 | Good | None |
| 116 | Good | 359 | Good | None |
| 117 | Good | 367 | Good | None |
| 118 | Good | 344 | Good | None |

TABLE 11-continued

| | | State after making 10,000 copies | | |
|---|---|---|---|---|
| Example | Copy image quality | Photoreceptor wear (nm) | Photoreceptor surface state | Adherence to photoreceptor |
| 119 | Good | 216 | Good | None |
| 120 | Good | 228 | Good | None |
| 121 | Good | 203 | Good | None |
| 122 | Good | 197 | Good | None |
| 123 | Good | 190 | Good | None |
| 124 | Good | 176 | Good | None |
| 125 | Good | 283 | Good | None |
| 126 | Good | 259 | Good | None |
| 127 | Good | 75 | Good | None |
| 128 | Good | 87 | Good | None |
| 129 | Good | 79 | Good | None |
| 130 | Good | 43 | Good | None |
| 131 | Good | 40 | Good | None |
| 132 | Good | 29 | Good | None |
| 133 | Good | 206 | Good | None |
| 134 | Good | 219 | Good | None |
| 135 | Good | 201 | Good | None |
| 136 | Good | 185 | Good | None |
| 137 | Good | 194 | Good | None |
| 138 | Good | 182 | Good | None |
| CE 5 | Image defects due to scratch of photoreceptor | 880 | Some scratch | Slight adherence |

CE: Comparative Example

Synthesis 201

Synthesis of Silane Compound 212

A two-neck flask purged with nitrogen was charged with 10.1 g of carboxylic acid 1 represented by the following structural formula, 4.6 g of 1,8-diazabicyclo[5.4.0]-7-undecene and 50 mL of dimethylformamide to produce a solution, which was heated to 100° C. Then, 7.6 g of [(chloromethyl)phenylethyl]trimethoxysilane was added to

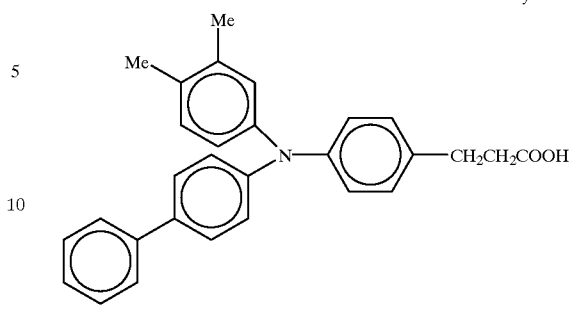

Carboxylic acid 1

Synthesis 202

Synthesis of Silane Compound 250

Figure 20:
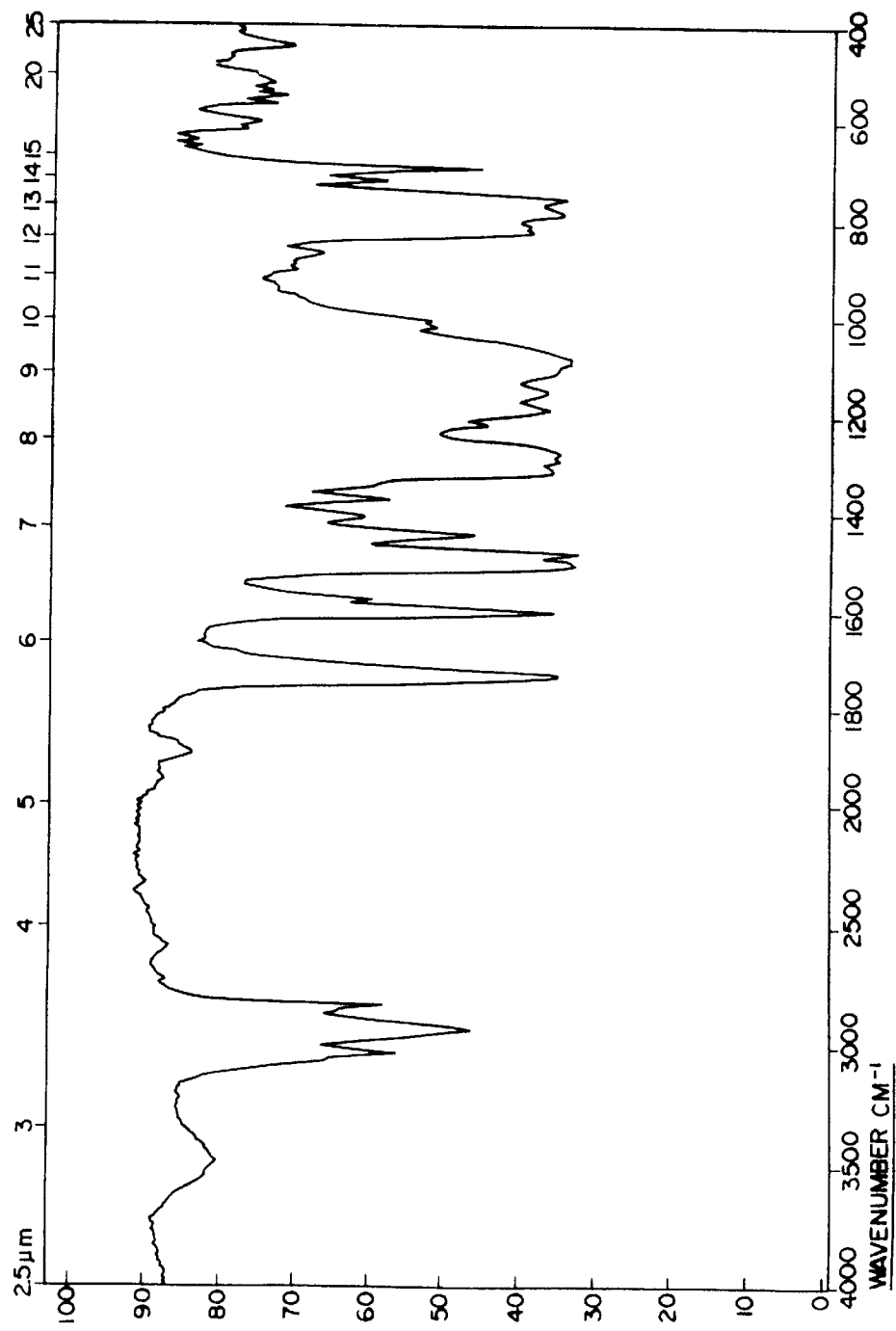
FIG. 20 shows the IR absorption spectrum of the silane compound prepared in Synthesis 201.
Figure 21:
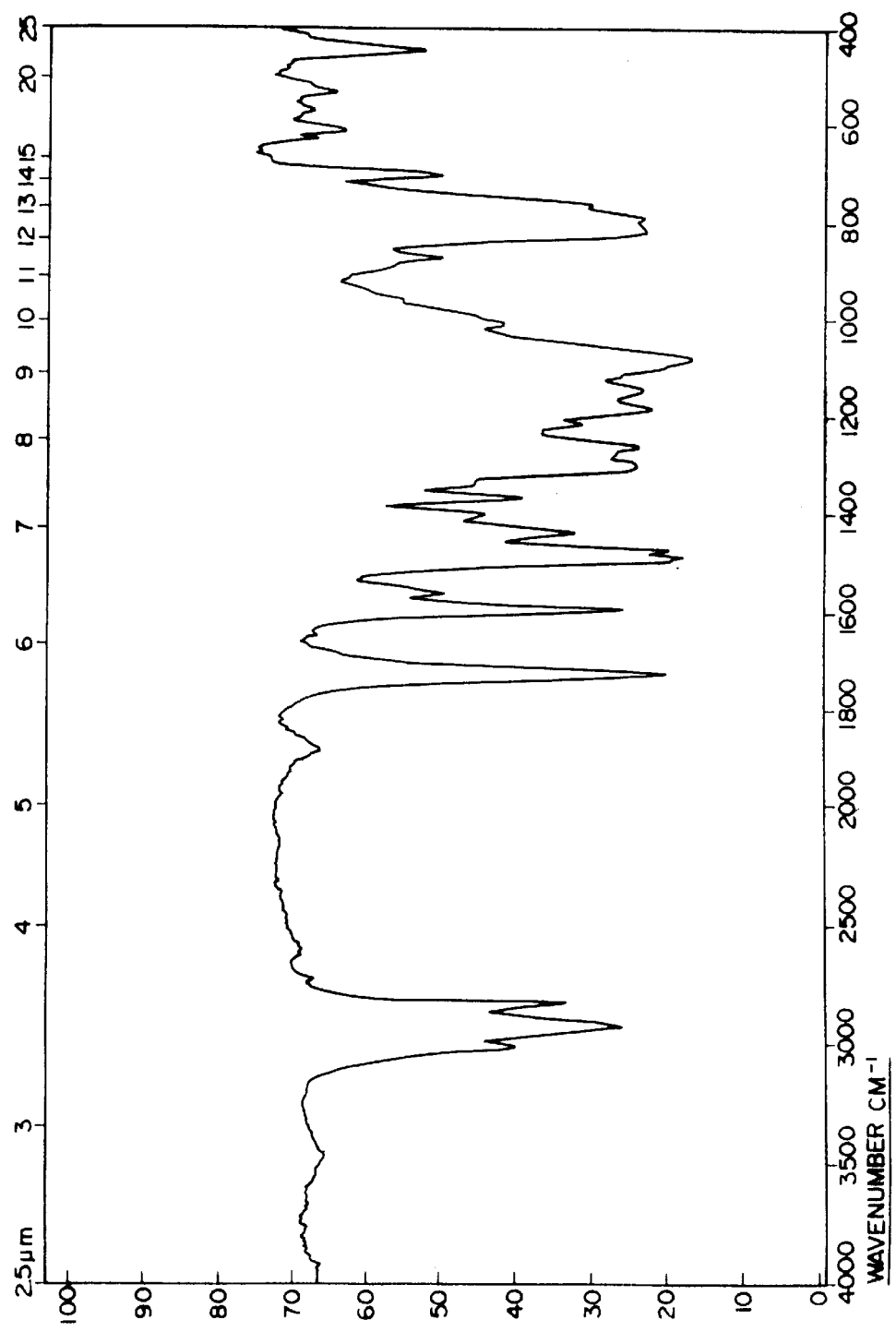
FIG. 21 shows the IR absorption spectrum of the silane compound prepared in Synthesis 202.

A pear-shaped flask purged with nitrogen was charged with 14.3 g of carboxylic acid 2 represented by the following structural formula: 7.3 g of 1,8-diazabicyclo[5.4.0]-7-undecene and 50 mL of dimethylformamide to produce a solution, which was heated to 100° C. Then, 12.4 g of [(chloromethyl)phenylethyl] trimethoxysilane was added to the solution and the solution was stirred for 6 hours at 100° C. Then, 500 mL of toluene and 300 mL of distilled water were added to the solution and the deposited insoluble product was filtered through celite. The extract as an organic layer was washed twice with 500 ml of distilled water and dried with anhydrous sodium sulfate. After removal of the solvent from the solution at reduced pressure, followed by purification by means of silica gel in a column (eluent: toluene/methylene chloride), 12.1 g of silane compound 250 as a pale yellow oily product was obtained. The IR absorption spectrum of the obtained silane compound 212 is shown in FIG. 21.

the solution and the solution was stirred for 4 hours at 100° C. Then, 500 mL of toluene was added to the solution and the resulting mixture was washed twice with 500 mL of distilled water. The extract as an organic layer was dried with anhydrous sodium sulfate. After removal of the solvent from the solution at reduced pressure, followed by purification by means of silica gel in a column (eluent: toluene/methylene chloride), 7.1 g of silane compound 212 as a pale yellow oily product was obtained. The IR absorption spectrum of the obtained silane compound 212 is shown in FIG. 20.

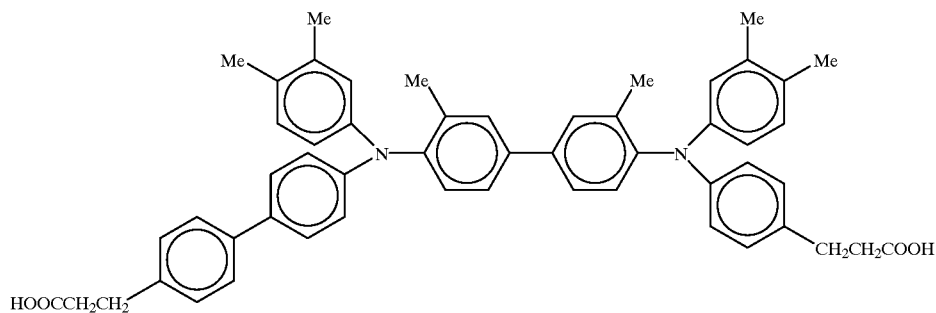

Carboxylic acid 2

Synthesis 203

Synthesis of Silane Compound 211

Figure 22:
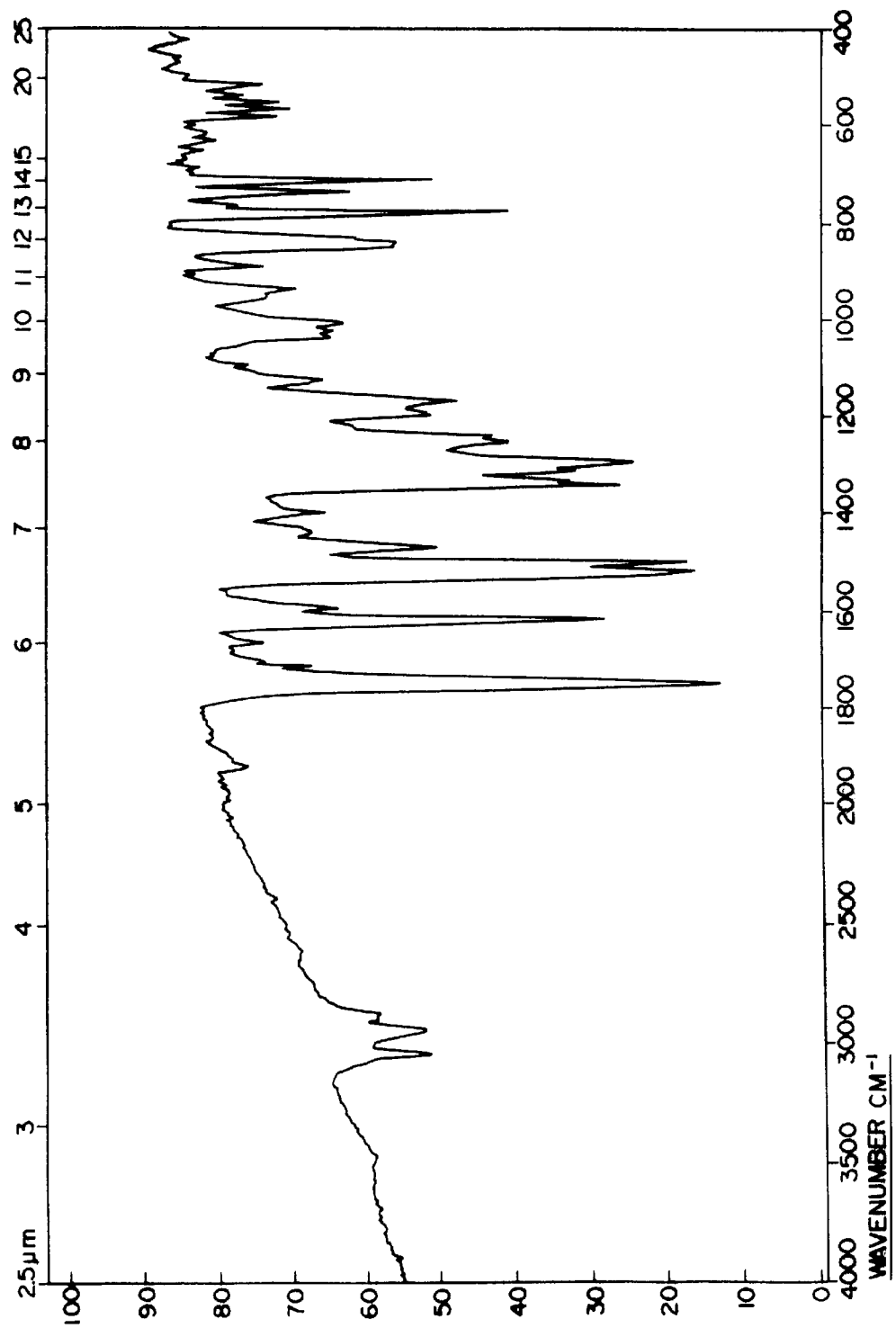
FIG. 22 shows the IR absorption spectrum of the silane compound prepared in Synthesis 203.

A two-neck flask purged with nitrogen was charged with 5.0 g of carboxylic acid (1) represented by the above-described structural formula, 5.0 g of allyl alcohol and 100 mL of toluene, and thus a solution was produced. Then, 1 mL of concentrated sulfuric acid was added dropwise to the solution over a period of 15 hours. After completion of the addition, the reaction mixture was washed twice with 200 mL of distilled water. The extract as an organic layer was dried by the addition of anhydrous sodium sulfate. After removal of the solvent from the solution at reduced pressure, followed by purification by means of silica gel in a column (eluent: toluene) and further by means of recrystallization, 5.2 g of vinyl-containing ester 1 represented by the following structural formula was obtained. The product had a melting point in the rang of 107 to 109° C., and was in a state of white crystals. The IR absorption spectrum of the obtained silane compound is shown in FIG. 22.

Figure 23:
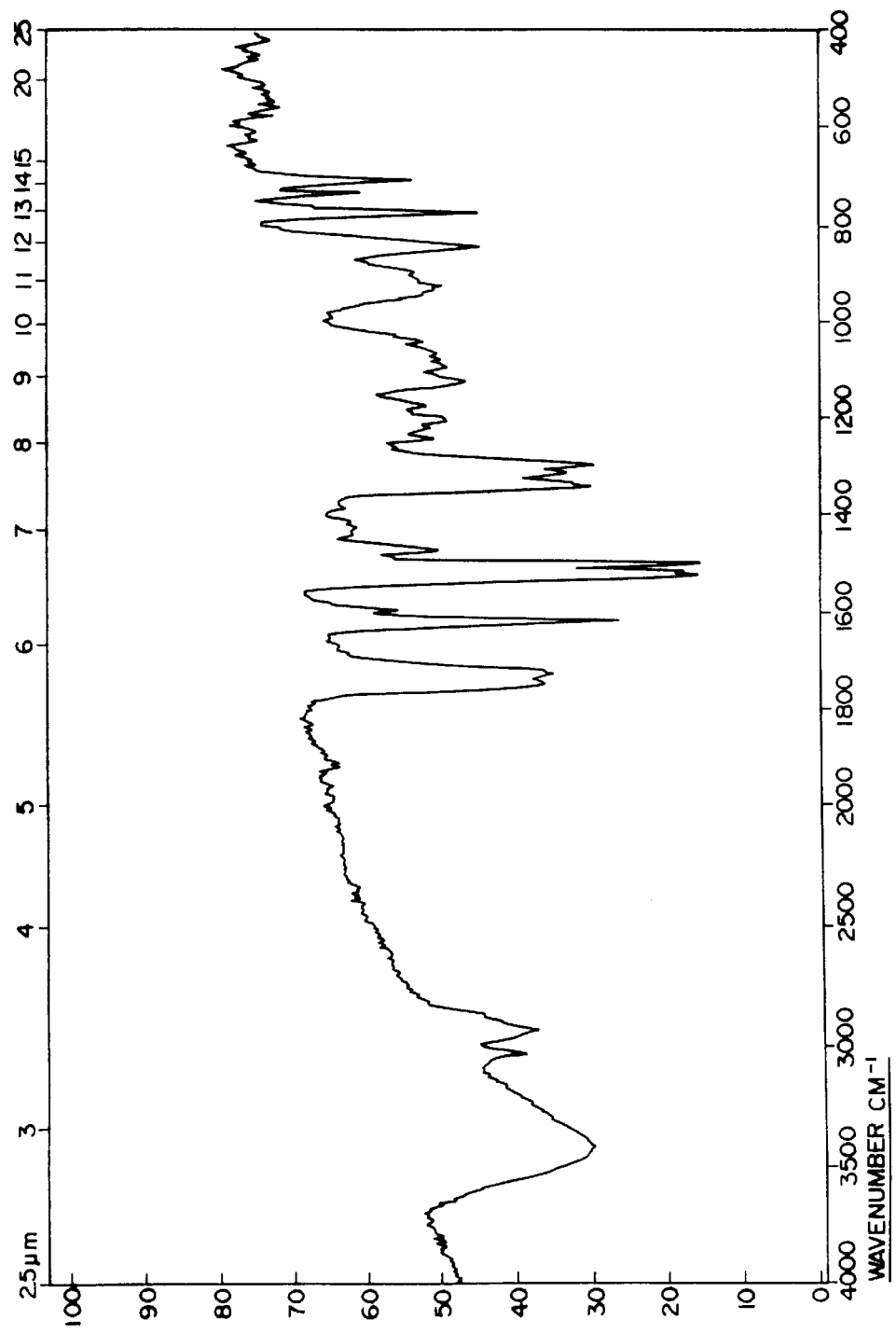
FIG. 23 shows the IR absorption spectrum of the silane compound prepared in Synthesis 203.

A two-neck flask purged with nitrogen was charged with 3 g of vinyl-containing ester 1 and 3 g of trimethoxysilane. To this mixture, which was kept agitated, there was added dropwise 0.1 mL of $H_2PtCl_6 \cdot 6H_2O$ (as 1% isopropanol solution), which addition converted the reaction mixture into a solution as the reaction proceeded. The reaction mixture was caused to react for 3 hours while being stirred. Then, 50 mL of toluene was added to the reaction mixture and the resulting mixture was poured into 100 mL of distilled water for washing. The extract as an organic layer was dried by the addition of anhydrous sodium sulfate. After removal of the solvent from the solution at reduced pressure, followed by purification by means of silica gel in a column (eluent: toluene/methylene chloride), 7.1 g of silane compound 211 as a pale yellow oily product was obtained. The IR absorption spectrum of the obtained silane compound 211 is shown in FIG. 23.

Vinyl - containing ester 1

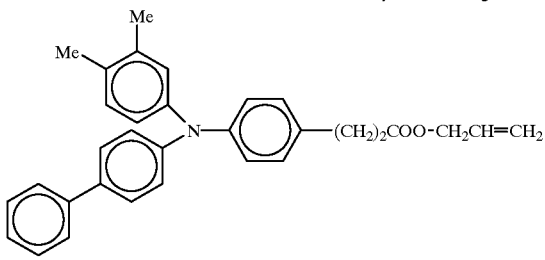

Examples 201–228

The procedure of Examples 24–31 was repeated to prepare electrophotographic photoreceptors each from the silane compound 211 and from the silane compound 250 except that the combinations of the charge-generation material and the charge-transport material of Table 201 were employed. The evaluation of the prepared electrophotographic photoreceptors was conducted and the results are shown in Table 201.

TABLE 201

| Example | Compound No. | Charge-generation material | Charge-transport material | Image quality (copy) 1st | 2,000th |
|---|---|---|---|---|---|
| 201 | 211 | CG-1 | CT-1 | Good | Good |
| 202 | 211 | CG-2 | CT-1 | Good | Good |
| 203 | 211 | CG-3 | CT-1 | Good | Good |
| 204 | 211 | CG-4 | CT-1 | Good | Good |
| 205 | 250 | CG-1 | CT-1 | Good | Good |
| 206 | 250 | CG-2 | CT-1 | Good | Good |
| 207 | 250 | CG-3 | CT-1 | Good | Good |
| 208 | 250 | CG-4 | CT-1 | Good | Good |

The procedure of Examples 24–31 was repeated to prepare electrophotographic photoreceptors each from the silane compounds 211 and 250 except that the combinations of the charge-generation material and the charge-transport material of Table 202 were employed. The evaluation of the prepared electrophotographic photoreceptors was conducted and the results are shown in Table 202.

TABLE 202

| Example | Compound No. | CTL binder | Image quality (copy) 1st | 2,000th |
|---|---|---|---|---|
| 209 | 211 | IV | Good | Good |
| 210 | 211 | V | Good | Good |
| 211 | 250 | IV | Good | Good |
| 212 | 250 | V | Good | Good |

| Example | Compound No. | Fluorine-containing compound | Catalyst |
|---|---|---|---|
| 213 | 211 | PTFE | 1N-HCl |
| 214 | 211 | $CF_3CF_2CH_2OMe$ | ↑ |
| 215 | 211 | $F(CF_2)_7COOMe$ | ↑ |
| 216 | 211 | $F(CF_2)_7COOH$ | — |
| 217 | 211 | $F(CF_2)_7CH_2NH_2$ | — |
| 218 | 211 | $F(CF_2)_8CH_2CH_2OH$ | 1N-HCl |
| 219 | 211 | $F(CF_2)_8CH_2CH_2Si(OMe)_3$ | ↑ |
| 220 | 211 | $CF_3CH_2CH_2Si(OMe)_3$ | ↑ |
| 221 | 250 | PTFE | ↑ |
| 222 | 250 | $CF_3CF_2CH_2OMe$ | ↑ |
| 223 | 250 | $F(CF_2)_7COOMe$ | ↑ |
| 224 | 250 | $F(CF_2)_7COOH$ | — |
| 225 | 250 | $F(CF_2)_7CH_2NH_2$ | — |
| 226 | 250 | $F(CF_2)_8CH_2CH_2OH$ | 1N-HCl |
| 227 | 250 | $F(CF_2)_8CH_2CH_2Si(OMe)_3$ | ↑ |
| 228 | 250 | $CF_3CH_2CH_2Si(OMe)_3$ | ↑ |

| | After 10,000 copies | | | |
|---|---|---|---|---|
| Example | Copy image quality | Photoreceptor wear (nm) | Photoreceptor surface state | Adherence to the photoreceptor |
| 213 | Good | 430 | Good | None |
| 214 | Good | 642 | Good | None |
| 215 | Good | 453 | Good | None |
| 216 | Good | 527 | Good | None |
| 217 | Good | 405 | Good | None |
| 218 | Good | 254 | Good | None |
| 219 | Good | 91 | Good | None |
| 220 | Good | 232 | Good | None |
| 221 | Good | 411 | Good | None |
| 222 | Good | 625 | Good | None |
| 223 | Good | 423 | Good | None |
| 224 | Good | 509 | Good | None |
| 225 | Good | 416 | Good | None |
| 226 | Good | 225 | Good | None |
| 227 | Good | 65 | Good | None |
| 228 | Good | 210 | Good | None |

What is claimed is:

1. A silane compound represented by general formula I:

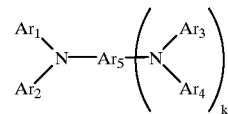

wherein

Ar$_1$–Ar$_4$ are independently substituted or unsubstituted aryl groups;

Ar$_5$ is a substituted or unsubstituted aryl or arylene group, provided that one to four of Ar$_1$–Ar$_5$ have a substituent represented by —Q—SiR$_{1(3-a)}$(OR$_2$)$_a$ where R$_1$ is selected from the group consisting of hydrogen, alkyl, and substituted and unsubstituted aryl groups;

R$_2$ is selected from the group consisting of hydrogen, alkyl, and trialkylsilyl groups;

a is an integer of 1–3, Q is a divalent group containing at least one group selected from the group consisting of —$C_{x'}H_{2x'-2}$— (where x' is an integer of 2–17), —$C_{x''}H_{2x''-4}$— (where x'' is an integer of 2–17), a substituted or unsubstituted arylene group, —CH=N—, —O—, and —COO—; and k is 0 or 1.

2. A silane compound according to claim 1, wherein Q is —CH=CH—$Y^1$— where $Y^1$ is a divalent group containing at least one group selected from the group consisting of —$C_xH_{2x}$— (where x is an integer of 1–15), —$C_{x'}H_{2x'-2}$— (where x' is an integer of 2–15), —$C_{x''}H_{2x''-4}$— (where x'' is an integer of 2–15), a substituted or unsubstituted arylene group, —CH=N— and —O—.

3. A silane compound according to claim 1, wherein Q is —CH=N—$Y^2$— where $Y^2$ is a divalent group containing at least one group selected from the group consisting of —$C_xH_{2x}$— (where x is an integer of 1–15), —$C_{x'}H_{2x'-2}$— (where x' is an integer of 2–15), —$C_{x''}H_{2x''-4}$— (where x'' is an integer of 2–15), a substituted or unsubstituted arylene group, —CH=N— and —O—.

4. A silane compound according to claim 1, wherein Q is —$CH_2CH_2$—$Y^3$— where $Y^3$ is a divalent group containing at least one group selected from the group consisting of —$C_xH_{2x}$— (where x is an integer of 1–15), —$C_{x'}H_{2x'-2}$— (where x' is an integer of 2–15), —$C_{x''}H_{2x''-4}$— (where x'' is an integer of 2–15), a substituted or unsubstituted arylene group, —CH=N— and —O—.

5. A method for making the silane compound of claim 2 by reacting a compound represented by general formula A with a compound represented by general formula B in the presence of a base:

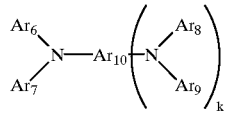

(A)

where

Ar$_6$–Ar$_9$ are independently substituted or unsubstituted aryl groups,

Ar$_{10}$ is a substituted or unsubstituted aryl or arylene group, provided that one to four of Ar$_6$–Ar$_{10}$ have a substituent represented by —CHO or —CH$_2$L where L stands for PM(R$_3$)$_2$ or Hal$^-$ P(R$_3$)$_3^+$ where Hal stands for a halogen atom, M stands for O or S and R$_3$ is selected from the group consisting of alkyl, phenyl, alkoxy and amino groups, and k is 0 or 1

(B)

where

R$_1$ is selected from the group consisting of hydrogen, alkyl, substituted and unsubstituted aryl groups, R$_2$ is selected from the group consisting of hydrogen, alkyl and trialkylsilyl groups, a is an integer of 1–3, $Y^1$ is a divalent group, T is —CH$_2$L in the case where general formula A has —CHO but —CHO in the case where general formula A has —CH$_2$L where L stands for PM(R$_3$)$_2$ or Hal$^-$ P(R$_3$)$_3^+$ where Hal stands for a halogen atom, M stands for O or S and R$_3$ is selected from the group consisting of alkyl, phenyl, alkoxy and amino groups.

6. A method for making the silane compound of claim 3 by reacting a compound represented by general formula A' with a compound represented by general formula B' in the presence of an acid:

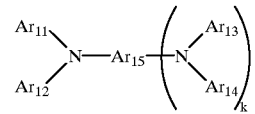

(A')

where Ar$_{11}$–Ar$_{15}$ are independently substituted or unsubstituted aryl groups, Ar$_{15}$ is a substituted or unsubstituted aryl or arylene group, provided that one to four of Ar$_{11}$–Ar$_{15}$ have a substituent represented by —CHO or —$Y^2$—NH$_2$ where $Y^2$ is a divalent group, and k is 0 or 1

(B')

where R$_1$ is selected from the group consisting of hydrogen, alkyl, substituted and unsubstituted aryl groups, R$_2$ is selected from the group consisting of hydrogen, alkyl and trialkylsilyl groups, a is an integer of 1–3, $Y^2$ is a divalent group, T is —$Y^2$—NH$_2$ in the case where general formula (A') has —CHO but —CHO in the case where general formula (A') has —$Y^2$—NH$_2$.

* * * * *